(12) United States Patent
Mrsny et al.

(10) Patent No.: US 11,027,020 B2
(45) Date of Patent: Jun. 8, 2021

(54) DELIVERY CONSTRUCTS FOR TRANSCYTOSIS AND RELATED METHODS

(71) Applicant: Applied Molecular Transport Inc., South San Francisco, CA (US)

(72) Inventors: Randall J. Mrsny, South San Francisco, CA (US); Tahir Mahmood, South San Francisco, CA (US); Charles Olson, South San Francisco, CA (US); Weijun Feng, South San Francisco, CA (US); Sally Postlethwaite, Redwood City, CA (US)

(73) Assignee: Applied Molecular Transport Inc., South San Francisco, CA (US)

( * ) Notice: Subject to any disclaimer, the term of this patent is extended or adjusted under 35 U.S.C. 154(b) by 0 days.

(21) Appl. No.: 16/902,256

(22) Filed: Jun. 15, 2020

(65) Prior Publication Data
US 2020/0306383 A1   Oct. 1, 2020

Related U.S. Application Data

(63) Continuation of application No. PCT/US2019/060356, filed on Nov. 7, 2019.

(60) Provisional application No. 62/756,889, filed on Nov. 7, 2018, provisional application No. 62/888,133, filed on Aug. 16, 2019, provisional application No. 62/888,238, filed on Aug. 16, 2019.

(51) Int. Cl.
*A61K 47/64*    (2017.01)
*A61K 38/20*    (2006.01)
*A61P 1/00*     (2006.01)
*C07K 1/18*     (2006.01)

(52) U.S. Cl.
CPC .......... *A61K 47/642* (2017.08); *A61K 38/20* (2013.01); *A61P 1/00* (2018.01); *C07K 1/18* (2013.01)

(58) Field of Classification Search
CPC .... A61K 47/642; A61K 38/162; A61K 38/20; A61K 47/6415; C07K 14/54; C07K 14/28; C07K 2319/00; C07K 2319/55
See application file for complete search history.

(56) References Cited

U.S. PATENT DOCUMENTS

| | | |
|---|---|---|
| 5,668,255 A | 9/1997 | Murphy |
| 5,696,237 A | 12/1997 | Fitzgerald et al. |
| 5,863,745 A | 1/1999 | Fitzgerald et al. |
| 6,022,950 A | 2/2000 | Murphy |
| 6,673,574 B2 | 1/2004 | Stern et al. |
| 7,713,737 B2 | 5/2010 | Mrsny |
| 9,090,691 B2 | 7/2015 | Mrsny et al. |
| 10,130,688 B2 | 11/2018 | Mrsny et al. |
| 10,143,726 B2 | 12/2018 | Oft |
| 10,617,741 B2 | 4/2020 | Mrsny et al. |
| 10,617,767 B2 | 4/2020 | Mrsny et al. |
| 10,624,955 B2 | 4/2020 | Mrsny et al. |
| 10,624,956 B2 | 4/2020 | Mrsny et al. |
| 10,624,957 B2 | 4/2020 | Mrsny et al. |
| 10,786,555 B2 | 9/2020 | Mrsny et al. |
| 10,786,556 B2 | 9/2020 | Mrsny et al. |
| 10,799,565 B2 | 10/2020 | Mrsny et al. |
| 2009/0092660 A1 | 4/2009 | Mrsny |
| 2009/0148401 A1 | 6/2009 | Mrsny |
| 2009/0155297 A1 | 6/2009 | Mrsny |
| 2010/0143481 A1 | 6/2010 | Shenoy et al. |
| 2011/0250199 A1 | 10/2011 | Fitzgerald et al. |
| 2012/0258104 A1 | 10/2012 | Echeverri et al. |
| 2012/0276190 A1 | 11/2012 | Fitzgerald |
| 2014/0065172 A1 | 3/2014 | Echeverri et al. |
| 2015/0164997 A1 | 6/2015 | Haack et al. |
| 2015/0216981 A1 | 8/2015 | Bley et al. |
| 2015/0265718 A1 | 9/2015 | Mrsny et al. |
| 2015/0265719 A1 | 9/2015 | Mrsny et al. |
| 2016/0263020 A1 | 9/2016 | Yan et al. |
| 2016/0287670 A1 | 10/2016 | Van Den Brink et al. |
| 2018/0028614 A1 | 2/2018 | Huang et al. |
| 2018/0353610 A1 | 12/2018 | Mrsny et al. |
| 2019/0177388 A1 | 6/2019 | Scheer et al. |
| 2020/0140511 A1 | 5/2020 | Porat et al. |

FOREIGN PATENT DOCUMENTS

| | | |
|---|---|---|
| CN | 101522214 A | 9/2009 |
| CN | 102227447 A | 10/2011 |
| EP | 0188256 A2 | 7/1986 |
| EP | 1522585 A1 | 4/2005 |
| EP | 1450855 B1 | 8/2009 |

(Continued)

OTHER PUBLICATIONS

Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138,1990 (Year: 1990).*
Lazar et al. Transforming Growth Factor alpha: Mutation of Aspartic Acid 47 and Leucine 48 Results in Different Biological Activities. Mol. Cell. Biol., 8:1247-1252,1988 (Year: 1988).*
Bork. Powers and Pitfalls in Sequence Analysis: The 70% Hurdle. Genome Research, 2000; 10:398-400 (Year: 2000).*

(Continued)

*Primary Examiner* — Vanessa L. Ford
*Assistant Examiner* — Sandra E Dillahunt
(74) *Attorney, Agent, or Firm* — Wilson Sonsini Goodrich & Rosati

(57) ABSTRACT

The present disclosure provides non-naturally occurring fusion molecules comprising therapeutic cargo moieties, such as IL-22 with a carrier. The disclosure also provides methods and compositions for the production, purification, refolding, formulation, and administration of fusion molecules. Methods and for using the purified molecules to treat and prevent diseases or disorders are also provided herein.

15 Claims, 29 Drawing Sheets

Specification includes a Sequence Listing.

(56) References Cited

FOREIGN PATENT DOCUMENTS

| | | | |
|---|---|---|---|
| EP | 1379273 | B1 | 9/2009 |
| EP | 3402810 | A1 | 11/2018 |
| EP | 3474884 | A2 | 5/2019 |
| EP | 3554346 | A1 | 10/2019 |
| EP | 3554541 | A1 | 10/2019 |
| WO | WO-2009149281 | A1 | 12/2009 |
| WO | WO-2012036746 | A1 | 3/2012 |
| WO | WO-2013003824 | A1 | 1/2013 |
| WO | WO-2015171965 | A2 * | 11/2015 ........... A61K 38/166 |
| WO | WO-2019173787 | A1 | 9/2019 |
| WO | WO-2020096695 | A1 | 5/2020 |
| WO | WO-2020097394 | A1 | 5/2020 |

OTHER PUBLICATIONS

Aman et al. A mutant cholera toxin B subunit that binds GM1-ganglioside but lacks immunomodulatory or toxic activity. PNAS 98(15):8536-8541 (Jul. 17, 2001).

Anselmo et al. Non-invasive delivery strategies for biologics. Nature Reviews Drug Discovery 18:19-40 (Jan. 2019). Published online Nov. 30, 2018.

Arango Duque et al. Macrophage cytokines: involvement in immunity and infectious diseases. Frontiers in Immunology, vol. 5, Article 491, 12 pages (Oct. 7, 2014).

Arhewoh et al. An overview of site-specific delivery of orally administered proteins/peptides and modelling considerations. JMBR: A Peer-review Journal of Biomedical Sciences 3(1):7-20 (Jun. 2004).

Awasthi et al. Development of a PCR-restriction fragment length polymorphism assay for detection and subtyping of cholix toxin variant genes of Vibrio cholerae. Journal of Medical Microbiology 63(5):667-673 (May 1, 2014). DOI: 10.1099/jmm.0.070797-0.

Awasthi et al. Novel Cholix Toxin Variants, ADP-Ribosylating Toxins in Vibriocholerae Non-O1/Non-O139 Strains, and Their Pathogenicity. Infection and Immunity 81(2):531-541 (Feb. 2013). Published ahead of print Dec. 10, 2012.

Backert et al. STAT3 Activation in Th17 and Th22 Cells Controls IL-22-Mediated Epithelial Host Defense during Infectious Colitis. J Immunol 193(7):3779-3791 (Oct. 1, 2014). Prepublished online Sep. 3, 2014. doi: 10.4049/jimmunol.1303076.

Basset et al. Cholera-Like Enterotoxins and Regulatory T cells. Toxins 2:1774-1795 (Jul. 6, 2010). doi:10.3390/toxins2071774.

Bishop-Lilly et al. Genome Sequencing of 15 Clinical Vibrio Isolates, Including 13 Non-O1/Non-O139 Serogroup Strains. Genome Announc 2(5):e00893-14 (Sep. 11, 2014). doi:10.1128/genomeA.00893-14.

Blumberg et al. Interleukin 20: Discovery, Receptor Identification, and Role in Epidermal Function. Cell 104:9-19 (Jan. 12, 2001).

Boirivant et al. Oral Administration of Recombinant Cholera Toxin Subunit B Inhibits IL-12-Mediated Murine Experimental (Trinitrobenzene Sulfonic Acid) Colitis. J Immunol 166:3522-3532 (2001). doi: 10.4049/jimmunol.166.5.3522.

Bonissone et al. N-terminal Protein Processing: A Comparative Proteogenomic Analysis. Molecular & Cellular Proteomics 12: 10.1074/mcp.M112.019075, 14-28 (2013).

Bowie et al. Deciphering the message in protein sequences: tolerance to amino acid substitutions. Science 247:1306-1310 (1990).

Bublin et al. Use of a genetic cholera toxin B subunit/allergen fusion molecule as mucosal delivery system with immunosuppressive activity against Th2 immune responses. Vaccine 25(50):8395-8404 (Dec. 5, 2007). DOI: https://doi.org/10.1016/j.vaccine.2007.10.003.

Cavalli et al. Treating rheumatological diseases and co-morbidities with interleukin-1 blocking therapies. Rheumatology 54:2134-2144 (2015). Advance Access publication Jul. 23, 2015. doi: 10.1093/rheumatology/kev269.

Chen et al. Cytokine Networks and T-Cell Subsets in Inflammatory Bowel Diseases. Inflammatory Bowel Diseases 22(5):1157-1167 (May 1, 2016).

Choonara et al. A review of advanced oral drug delivery technologies facilitating the protection and absorption of protein and peptide molecules. Biotechnology Advances 32:1269-282 (2014). Available online Aug. 3, 2014.

Co-pending U.S. Appl. No. 16/779,350, inventors Liu; Keyi et al., filed Jan. 31, 2020.

Co-pending U.S. Appl. No. 16/884,456, inventors Mrsny; Randall J. et al., filed May 27, 2020.

Co-pending U.S. Appl. No. 16/997,781, inventors Mrsny; Randall J. et al., filed Aug. 19, 2020.

Co-pending U.S. Appl. No. 17/004,686, inventors Mrsny; Randall J. et al., filed Aug. 27, 2020.

Co-pending U.S. Appl. No. 17/015,011, inventor Liu; Keyi, filed Sep. 8, 2020.

Dalmas et al. A role for interleukin-22 in the alleviation of metabolic syndrome. Nature Medicine 20(12):1379-1381 (Dec. 2014). Published online Nov. 2, 2014. doi: 10.1038/nm.3748.

Dionne et al. Colonic explant production of IL-1 and its receptor antagonist is imbalanced in inflammatory bowel disease (IBD). Clin Exp Immunol 112(3):435-442 (1998).

Dixon et al. IL-17a and IL-22 Induce Expression of Antimicrobials in Gastrointestinal Epithelial Cells and May Contribute to Epithelial Cell Defense against Helicobacter pylori. PLoS One 11(2):e0148514 (Feb. 11, 2016). 19 pages. doi:10.1371/journal.pone.0148514.

Dudakov et al. Interleukin-22: immunobiology and pathology. Annu Rev Immunol 33:747-785 (Mar. 21, 2015). doi:10.1146/annurev-immunol-032414-112123.

Dumoutier et al. IL-TIF/IL-22: genomic organization and mapping of the human and mouse genes. Genes and Immunity 1:488-494 (2000).

Feuerstein et al. Crohn Disease: Epidemiology, Diagnosis, and Management. Mayo Clinic Proceedings 92(7):1088-1103 (Jul. 2017).

Flood et al. Development of a Freeze-Dried, Heat-Stable Influenza Subunit Vaccine Formulation. PLoS One 11(11):e0164692 (2016). Published online Nov. 16, 2016. 18 pages.

Frankel et al. Characterization of diphtheria fusion proteins targeted to the human interleukin-3 receptor. Protein Engineering 13(8):575-581 (2000).

Frolkis et al. Risk of Surgery for Inflammatory Bowel Diseases Has Decreased Over Time: A Systematic Review and Meta-analysis of Population-Based Studies. Gastroenterology 145(5):996-1006 (2013).

Garlanda et al. The Interleukin-1 Family: Back to the Future. Immunity 39:1003-1018 (Dec. 12, 2013).

GenBank Accession No. ALH24940. Version No. ALH24940.1. cholix toxin [Vibrio cholerae]. Record created Oct. 11, 2015. 2 pages. Retrieved Sep. 6, 2019 at URL: https://www.ncbi.nlm.nih.gov/protein/ALH24940.1.

GenBank Accession No. ALI16365. Version No. ALI16365.1. truncated cholix toxin [*Vibrio cholerae*]. Record created Oct. 12, 2015. 2 pages. Retrieved Sep. 9, 2019 at URL: https://www.ncbi.nlm.nih.gov/protein/ALI16365.1.

GenBank Accession No. ALI16366. Version No. ALI16366.1. truncated cholix toxin [*Vibrio cholerae*]. Record created Oct. 12, 2015. 2 pages. Retrieved Sep. 9, 2019 at URL: https://www.ncbi.nlm.nih.gov/protein/ALI16366.1.

GenBank Accession No. ALI87044. Version No. ALI87044.1. cholix toxin [*Vibrio cholerae*]. Record created Oct. 14, 2015. 2 pages. Retrieved Aug. 30, 2019 at URL: https://www.ncbi.nlm.nih.gov/protein/ALI87044.1.

GenBank Accession No. ALJ02941. Version No. ALJ02941.1. cholix toxin [*Vibrio cholerae*]. Record created Oct. 18, 2015. 2 pages. Retrieved Sep. 6, 2019 at URL: https://www.ncbi.nlm.nih.gov/protein/ALJ02941.1.

GenBank Accession No. AUT32289. Version No. AUT32289.1. cholix toxin [*Vibrio cholerae*]. Record created Jan. 31, 2018. 2 pages. retrieved Sep. 6, 2019 at URL: https://www.ncbi.nlm.nih.gov/protein/AUT32289.1.

GenBank Accession No. AUT32291. Version No. AUT32291.1. cholix toxin [*Vibrio cholerae*]. Record created Jan. 31, 2018. 2 pages. Retrieved Sep. 6, 2019 at URL: https://www.ncbi.nlm.nih.gov/protein/AUT32291.1.

(56) References Cited

OTHER PUBLICATIONS

GenBank Accession No. AUT32293. Version No. AUT32293.1. cholix toxin [*Vibrio cholerae*]. Record created Jan. 31, 2018. 2 pages. Retrieved Sep. 6, 2019 at URL: https://www.ncbi.nlm.nih.gov/protein/AUT32293.1.
GenBank Accession No. AUT32294. Version No. AUT32294.1. cholix toxin [*Vibrio cholerae*]. Record created Jan. 31, 2018. 2 pages. Retrieved Sep. 6, 2019 at URL: https://www.ncbi.nlm.nih.gov/protein/AUT32294.1.
GenBank Accession No. BAM72568. Version No. BAM72568.1. cholix toxin, partial [*Vibrio cholerae*]. Record created Dec. 14, 2012. 2 pages. Retrieved Sep. 9, 2019 at URL: https://www.ncbi.nlm.nih.gov/protein/BAM72568.1.
GenBank Accession No. BAM72569. Version No. BAM72569.1. cholix toxin, partial [*Vibrio cholerae*]. Record created Dec. 14, 2012. 2 pages. Retrieved Sep. 9, 2019 at URL: https://www.ncbi.nlm.nih.gov/protein/BAM72569.1.
GenBank Accession No. BAM72570. Version No. BAM72570.1. cholix toxin, partial [*Vibrio cholerae*]. Record created Dec. 14, 2012. 2 pages. Retrieved Sep. 9, 2019 at URL: https://www.ncbi.nlm.nih.gov/protein/BAM72570.1.
GenBank Accession No. BAM72571. Version No. BAM72571.1. cholix toxin, partial [*Vibrio cholerae*]. Record created Dec. 14, 2012. 2 pages. Retrieved Sep. 9, 2019 at URL: https://www.ncbi.nlm.nih.gov/protein/BAM72571.1.
GenBank Accession No. BAM72573. Version No. BAM72573.1. cholix toxin, partial [*Vibrio cholerae*]. Record created Dec. 14, 2012. 2 pages. Retrieved Sep. 6, 2019 at URL: https://www.ncbi.nlm.nih.gov/protein/BAM72573.1.
GenBank Accession No. BAM72574. Version No. BAM72574.1. cholix toxin, partial [*Vibrio cholerae*]. Record created Dec. 14, 2012. 2 pages. Retrieved Sep. 9, 2019 at URL: https://www.ncbi.nlm.nih.gov/protein/BAM72574.1.
GenBank Accession No. BAM72575. Version No. BAM72575.1. cholix toxin, partial [*Vibrio cholerae*]. Record created Dec. 14, 2012. 2 pages. Retrieved Sep. 6, 2019 at URL: https://www.ncbi.nlm.nih.gov/protein/BAM72575.1.
GenBank Accession No. BAM72576. Version No. BAM72576.1. cholix toxin, partial [*Vibrio cholerae*]. Record created Dec. 14, 2012. 2 pages. Retrieved Sep. 9, 2019 at URL: https://www.ncbi.nlm.nih.gov/protein/BAM72576.1.
GenBank Accession No. BAM72582. Version No. BAM72582.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72582.1.
GenBank Accession No. BAM72585. Version No. BAM72585.1. cholix toxin, partial [*Vibrio cholerae*]. Record created Dec. 14, 2012. 2 pages. Retrieved Sep. 9, 2019 at URL: https://www.ncbi.nlm.nih.gov/protein/BAM72585.1.
GenBank Accession No. BAM72587. Version No. BAM72587.1. cholix toxin, partial [*Vibrio cholerae*]. Record created Dec. 14, 2012. 2 pages. Retrieved Sep. 9, 2019 at URL: https://www.ncbi.nlm.nih.gov/protein/BAM72587.1.
GenBank Accession No. BAM72590. Version No. BAM72590.1. cholix toxin, partial [*Vibrio cholerae*]. Record created Dec. 14, 2012. 2 pages. Retrieved Sep. 6, 2019 at URL: https://www.ncbi.nlm.nih.gov/protein/BAM72590.1.
GenBank Accession No. BAM72593. Version No. BAM72593.1. cholix toxin, partial [*Vibrio cholerae*]. Record created Dec. 14, 2012. 2 pages. Retrieved Sep. 6, 2019 at URL: https://www.ncbi.nlm.nih.gov/protein/BAM72593.1.
GenBank Accession No. BAM72594. Version No. BAM72594.1. cholix toxin, partial [*Vibrio cholerae*]. Record created Dec. 14, 2012. 2 pages. Retrieved Sep. 6, 2019 at URL: https://www.ncbi.nlm.nih.gov/protein/BAM72594.1.
GenBank Accession No. BAM72595. Version No. BAM72595.1. cholix toxin, partial [*Vibrio cholerae*]. Record created Dec. 14, 2012. 2 pages. Retrieved Sep. 6, 2019 at URL: https://www.ncbi.nlm.nih.gov/protein/BAM72595.1.
GenBank Accession No. BAM72596. Version No. BAM72596.1. cholix toxin, partial [*Vibrio cholerae*]. Record created Dec. 14, 2012. 2 pages. Retrieved Sep. 6, 2019 at URL: https://www.ncbi.nlm.nih.gov/protein/BAM72596.1.
GenBank Accession No. BAM72610. Version No. BAM72610.1. cholix toxin, partial [*Vibrio cholerae*]. Record created Dec. 14, 2012. 2 pages. Retrieved Sep. 9, 2019 at URL: https://www.ncbi.nlm.nih.gov/protein/BAM72610.1.
GenBank Accession No. BAM72611. Version No. BAM72611.1. cholix toxin, partial [*Vibrio cholerae*]. Record created Dec. 14, 2012. 2 pages. Retrieved Sep. 6, 2019 at URL: https://www.ncbi.nlm.nih.gov/protein/BAM72611.1.
GenBank Accession No. EFH75651. Version No. EFH75651.1. conserved hypothetical protein [*Vibrio cholerae* RC385]. Record created Jun. 4, 2010. 2 pages. Retrieved Sep. 6, 2019 at URL: https://www.ncbi.nlm.nih.gov/protein/EFH75651.1.
GenBank Accession No. KFD89501. Version No. KFD89501.1. exotoxin a binding family protein [*Vibrio cholerae*]. Record created Jul. 31, 2014. pages. Retrieved Sep. 6, 2019 at URL: https://www.ncbi.nlm.nih.gov/protein/KFD89501.1.
GenBank Accession No. KFD96741. Version No. KFD96741.1. exotoxin a binding family protein [*Vibrio cholerae*]. Record created Jul. 31, 2014. 2 pages. Retrieved Sep. 9, 2019 at URL: https://www.ncbi.nlm.nih.gov/protein/KFD96741.1.
GenBank Accession No. KFE28160. Version No. KFE28160.1. exotoxin A binding family protein [*Vibrio cholerae*]. Record created Jul. 31, 2014. 2 pages. Retrieved Sep. 6, 2019 at URL: https://www.ncbi.nlm.nih.gov/protein/KFE28160.1.
GenBank Accession No. KNH55243. Version No. KNH55243.1. hypothetical protein A59_2898 [*Vibrio cholerae* 623-39]. Record created Aug. 5, 2015. 2 pages. Retrieved Sep. 6, 2019 at URL: https://www.ncbi.nlm.nih.gov/protein/KNH55243.1.
GenBank Accession No. P01241. Somatotropin. Record created Jul. 21, 1986. 12 pages. Retrieved Aug. 29, 2019 at URL: https://www.ncbi.nlm.nih.gov/protein/P01241.
GenBank Accession No. Q5EK40. Version No. Q5EK40.1. Cholix toxin. Record created Feb. 9, 2005. 9 pages. Retrieved Aug. 30, 2019 at URL: https://www.ncbi.nlm.nih.gov/protein/Q5EK40.1.
GenBank Accession No. SYZ81493. Version No. SYZ81493.1. Cholix toxin precursor [Vibrio cholerae]. Record created Sep. 6, 2018. 1 page. Retrieved Sep. 9, 2019 at URL: https://www.ncbi.nlm.nih.gov/protein/SYZ81493.1.
GenBank Accession No. WP_000941100. Version No. WP_000941100.1. Multispecies: cholix toxin [*Vibrio*]. Record created Feb. 5, 2013. 1 page. Retrieved Sep. 9, 2019 at URL: https://www.ncbi.nlm.nih.gov/protein/WP_000941100.1.
GenBank Accession No. WP_002044040. Version No. WP_002044040.1. cholix toxin [*Vibrio cholerae*]. Record created May 4, 2013. 1 page. Retrieved Sep. 9, 2019 at URL: https://www.ncbi.nlm.nih.gov/protein/WP_002044040.1.
GenBank Accession No. WP_032467916. Version No. WP_032467916.1. cholix toxin [*Vibrio cholerae*]. Record created Oct. 4, 2014. 1 page. Retrieved Sep. 9, 2019 at URL: https://www.ncbi.nlm.nih.gov/protein/WP_032467916.1.
GenBank Accession No. WP_032482668. Version No. WP_032482668.1. cholix toxin [*Vibrio cholerae*]. Record created Oct. 4, 2014. 1 page. Retrieved Sep. 9, 2019 at URL: https://www.ncbi.nlm.nih.gov/protein/WP_032482668.1.
GenBank Accession No. WP_033932701. Version No. WP_033932701.1. cholix toxin [*Vibrio cholerae*]. Record created Dec. 5, 2014. 1 page. Retrieved Sep. 9, 2019 at URL: https://www.ncbi.nlm.nih.gov/protein/WP_033932701.1.
GenBank Accession No. WP_042988437. Version No. WP_042988437.1. cholix toxin [*Vibrio cholerae*]. Record created Feb. 17, 2015. 1 page. Retrieved Sep. 9, 2019 at URL: https://www.ncbi.nlm.nih.gov/protein/WP_042988437.1.
GenBank Accession No. WP_057552180. Version No. WP_057552180.1. cholix toxin [*Vibrio cholerae*]. Record created Nov. 10, 2015. 1 page. Retrieved Sep. 9, 2019 at URL: https://www.ncbi.nlm.nih.gov/protein/WP_057552180.1.

(56) References Cited

OTHER PUBLICATIONS

GenBank Accession No. WP_057557199. Version No. WP_057557199.1. cholix toxin [*Vibrio cholerae*]. Record created Nov. 10, 2015. 1 page. Retrieved Sep. 9, 2019 at URL: https://www.ncbi.nlm.nih.gov/protein/WP_057557199.1.
GenBank Accession No. WP_069648100. Version No. WP_069648100.1. cholix toxin [*Vibrio cholerae*]. Record created Sep. 20, 2016. 1 page. Retrieved Sep. 9, 2019 at URL: https://www.ncbi.nlm.nih.gov/protein/WP_069648100.1.
GenBank Accession No. WP_071178365. Version No. WP_071178365.1. cholix toxin [*Vibrio cholerae*]. Record created Nov. 2, 2016. 1 page. Retrieved Sep. 9, 2019 at URL: https://www.ncbi.nlm.nih.gov/protein/WP_071178365.1.
GenBank Accession No. WP_071186455. Version No. WP_071186455.1. cholix toxin [*Vibrio cholerae*]. Record created Nov. 2, 2016. 1 page. Retrieved Sep. 9, 2019 at URL: https://www.ncbi.nlm.nih.gov/protein/WP_071186455.1.
GenBank Accession No. WP_076008260. Version No. WP_076008260.1. cholix toxin [*Vibrio cholerae*]. Record created Jan. 19, 2017. 1 page. Retrieved Sep. 9, 2019 at URL: https://www.ncbi.nlm.nih.gov/protein/WP_076008260.1.
GenBank Accession No. WP_076025263. Version No. WP_076025263.1. cholix toxin [*Vibrio cholerae*]. Record created Jan. 19, 2017. 1 page. Retrieved Sep. 9, 2019 at URL: https://www.ncbi.nlm.nih.gov/protein/WP_076025263.1.
GenBank Accession No. WP_084980904. Version No. WP_084980904.1. cholix toxin [*Vibrio cholerae*]. Record created Apr. 21, 2017. 1 page. Retrieved Sep. 9, 2019 at URL: https://www.ncbi.nlm.nih.gov/protein/WP_084980904.1.
GenBank Accession No. WP_088131881. Version No. WP_088131881.1. cholix toxin [*Vibrio cholerae*]. Record created Jun. 19, 2017. 1 page. Retrieved Sep. 6, 2019 at URL: https://www.ncbi.nlm.nih.gov/protein/WP_088131881.1.
GenBank Accession No. WP_095461883. Version No. WP_095461883.1. cholix toxin [*Vibrio cholerae*]. Record created Sep. 2, 2017. 1 page. Retrieved Sep. 9, 2019 at URL: https://www.ncbi.nlm.nih.gov/protein/WP_095461883.1.
GenBank Accession No. WP_095463544. Version No. WP_095463544.1. cholix toxin [*Vibrio cholerae*]. Record created Sep. 2, 2017. 1 page. Retrieved Sep. 9, 2019 at URL: https://www.ncbi.nlm.nih.gov/protein/WP_095463544.1.
GenBank Accession No. WP_095466115. Version No. WP_095466115.1. cholix toxin [*Vibrio cholerae*]. Record created Sep. 2, 2017. 1 page. Retrieved Sep. 6, 2019 at URL: https://www.ncbi.nlm.nih.gov/protein/WP_095466115.1.
GenBank Accession No. WP_095473667. Version No. WP_095473667.1. cholix toxin [*Vibrio cholerae*]. Record created Sep. 2, 2017. 1 page. Retrieved Sep. 9, 2019 at URL: https://www.ncbi.nlm.nih.gov/protein/WP_095473667.1.
GenBank Accession No. WP_095477173. Version No. WP_095477173.1. cholix toxin [*Vibrio cholerae*]. Record created Sep. 2, 2017. 1 page. Retrieved Sep. 9, 2019 at URL: https://www.ncbi.nlm.nih.gov/protein/WP_095477173.1.
GenBank Accession No. WP_095490358. Version No. WP_095490358.1. cholix toxin [*Vibrio cholerae*]. Record created Sep. 2, 2017. 1 page. Retrieved Sep. 9, 2019 at URL: https://www.ncbi.nlm.nih.gov/protein/WP_095490358.1.
GenBank Accession No. WP_113605545. Version No. WP_113605545.1. cholix toxin [*Vibrio sp.* 2017V-1105]. Record created Jul. 15, 2018. 1 page. Retrieved Sep. 9, 2019 at URL: https://www.ncbi.nlm.nih.gov/protein/WP_113605545.1.
GenBank Accession No. WP_113620122. Version No. WP_113620122.1. cholix toxin [*Vibrio sp.* 2014V-1107]. Record created Jul. 15, 2018. 1 page. Retrieved Sep. 9, 2019 at URL: https://www.ncbi.nlm.nih.gov/protein/WP_113620122.1.
GenBank Accession No. WP_113628761. Version No. WP_113628761.1. cholix toxin [*Vibrio cholerae*]. Record created Jul. 15, 2018. 1 page. Retrieved Sep. 6, 2019 at URL: https://www.ncbi.nlm.nih.gov/protein/WP_113628761.1.
GenBank Accession No. WP_114707943. Version No. WP_114707943.1. cholix toxin [*Vibrio cholerae*]. Record created Aug. 2, 2018. 1 page. Retrieved Sep. 9, 2019 at URL: https://www.ncbi.nlm.nih.gov/protein/WP_114707943.1.
GenBank Accession No. WP_114708586. Version No. WP_114708586.1. cholix toxin [*Vibrio cholerae*]. Record created Aug. 2, 2018. 1 page. Retrieved Sep. 6, 2019 at URL: https://www.ncbi.nlm.nih.gov/protein/WP_114708586.1.
GenBank Accession No. WP_114711324. Version No. WP_114711324.1. cholix toxin [*Vibrio cholerae*]. Record created Aug. 2, 2018. 1 page. Retrieved Sep. 9, 2019 at URL: https://www.ncbi.nlm.nih.gov/protein/WP_114711324.1.
GenBank Accession No. WP_114718037. Version No. WP_114718037.1. cholix toxin [*Vibrio cholerae*]. Record created Aug. 2, 2018. 1 page. Retrieved Sep. 6, 2019 at URL: https://www.ncbi.nlm.nih.gov/protein/WP_114718037.1.
GenBank Accession No. WP_114728533. Version No. WP_114728533.1. cholix toxin [*Vibrio cholerae*]. Record created Aug. 2, 2018. 2 pages. Retrieved Sep. 6, 2019 at URL: https://www.ncbi.nlm.nih.gov/protein/WP_114728533.1.
GenBank Accession No. WP_114735885. Version No. WP_114735885.1. cholix toxin [*Vibrio cholerae*]. Record created Aug. 2, 2018. 1 page. Retrieved Sep. 6, 2019 at URL: https://www.ncbi.nlm.nih.gov/protein/WP_114735885.1.
GenBank Accession No. WP_114741531. Version No. WP_114741531.1. cholix toxin [*Vibrio cholerae*]. Record created Aug. 2, 2018. 1 page. Retrieved Sep. 6, 2019 at URL: https://www.ncbi.nlm.nih.gov/protein/WP_114741531.1.
GenBank Accession No. WP_114743333. Version No. WP_114743333.1. cholix toxin [*Vibrio cholerae*]. Record created Aug. 2, 2018. 1 page. Retrieved Sep. 9, 2019 at URL: https://www.ncbi.nlm.nih.gov/protein/WP_114743333.1.
GenBank Accession No. WP_114774300. Version No. WP_114774300.1. cholix toxin [Vibrio cholerae]. Record created Aug. 2, 2018. 1 page. Retrieved Sep. 6, 2019 at URL: https://www.ncbi.nlm.nih.gov/protein/WP_114774300.1.
GenBank Accession No. WP_114776277. Version No. WP_114776277.1. cholix toxin [Vibrio cholerae]. Record created Aug. 2, 2018. 1 page. Retrieved Sep. 6, 2019 at URL: https://www.ncbi.nlm.nih.gov/protein/WP_114776277.1.
GenBank Accession No. WP_114788528. Version No. WP_114788528.1. cholix toxin, partial [*Vibrio cholerae*]. Record created Aug. 2, 2018. 1 page. Retrieved Sep. 9, 2019 at URL: https://www.ncbi.nlm.nih.gov/protein/WP_114788528.1.
GenBank Accession No. WP_114794357. Version No. WP_114794357.1. cholix toxin [*Vibrio cholerae*]. Record created Aug. 2, 2018. 1 page. Retrieved Sep. 6, 2019 at URL: https://www.ncbi.nlm.nih.gov/protein/WP_114794357.1.
GenBank Accession No. WP_114808068. Version No. WP_114808068.1. cholix toxin [*Vibrio cholerae*]. Record created Aug. 2, 2018. 1 page. Retrieved Sep. 9, 2019 at URL: https://www.ncbi.nlm.nih.gov/protein/WP_114808068.1.
GenBank Accession No. WP_114967888. Version No. WP_114967888.1. cholix toxin [*Vibrio cholerae*]. Record created Aug. 3, 2018. 1 page. Retrieved Sep. 9, 2019 at URL: https://www.ncbi.nlm.nih.gov/protein/WP_114967888.1.
GenBank Accession No. WP_114974465. Version No. WP_114974465.1. cholix toxin [*Vibrio cholerae*]. Record created Aug. 3, 2018. 1 page. Retrieved Sep. 9, 2019 at URL: https://www.ncbi.nlm.nih.gov/protein/WP_114974465.1.
GenBank Accession No. WP_119788544. Version No. WP_119788544.1. cholix toxin [*Vibrio cholerae*]. Record created Sep. 26, 2018. 1 page. Retrieved Sep. 9, 2019 at URL: https://www.ncbi.nlm.nih.gov/protein/WP_119788544.1.
GenBank Accession No. WP_123013236. Version No. WP_123013236.1. cholix toxin [*Vibrio cholerae*]. Record created Nov. 10, 2018. 1 page. Retrieved Sep. 9, 2019 at URL: https://www.ncbi.nlm.nih.gov/protein/WP_123013236.1.
GenBank Accession No. WP_123162729. Version No. WP_123162729.1. cholix toxin [Vibrio cholerae]. Record created Nov. 14, 2018. 1 page. Retrieved Sep. 9, 2019 at URL: https://www.ncbi.nlm.nih.gov/protein/WP_123162729.1.

(56) References Cited

OTHER PUBLICATIONS

Ghasemi et al. mPEG-PLA and PLA-PEG-PLA nanoparticles as new carriers for delivery of recombinant human Growth Hormone (rhGH). Scientific Reports vol. 8, Article No. 9854 (Jun. 29, 2018). Author correction published Sep. 3, 2019. 13 pages.
Ghosh et al. Peptides as drug delivery vehicles across biological barriers. Journal of Pharmaceutical Investigation 48:89-111 (Jan. 2018). Published online Dec. 12, 2017.
Gikanga et al. Manufacturing of High-Concentration Monoclonal Antibody Formulations via Spray Drying—the Road to Manufacturing Scale. PDA J Pharm Sci Technol 69(1):59-73 (Jan.-Feb. 2015).
Hainzl et al. Intestinal Epithelial Cell Tyrosine Kinase 2 Transduces IL-22 Signals to Protect from Acute Colitis. The Journal of Immunology 195:5011-5024 (Nov. 15, 2015).
Hajishengallis et al. Type II Heat-labile Enterotoxins: Structure, Function, and Immunomodulatory Properties. Vet Immunol Immunopathol 152(1-2):68-77 (Mar. 15, 2013). doi:10.1016/j.vetimm.2012.09.034.
Hallegua et al. Potential therapeutic uses of interleukin 1 receptor antagonists in human diseases. Ann Rheum Dis 61:960-967 (2002).
Huyghebaert et al. In vitro evaluation of coating polymers for enteric coating and human ileal targeting. International Journal of Pharmaceutics 298(1):26-37 (2005). Available online May 13, 2005.
Hyams et al. Relationship of interleukin-1 receptor antagonist to mucosal inflammation in inflammatory bowel disease. J Pediatr Gastroenterol Nutr. 21(4):419-425 (1995). DOI: 10.1097/00005176-199511000-00008.
Jiang et al. A Multiparticulate Delivery System for Potential Colonic Targeting Using Bovine Serum Albumin as a Model Protein. Pharmaceutical Research 34:2663-2674 (Dec. 2017). Published online Aug. 14, 2017.
Johnson et al. Complete Genome Assemblies for Two Single-Chromosome Vibrio cholerae Isolates, Strains 1154-74 (Serogroup O49) and 10432-62 (Serogroup O27). Genome Announc 3(3):e00462-15 (May 14, 2015). 2 pages. doi:10.1128/genomeA.00462-15.
Jovanović et al. Stabilization of Proteins in Dry Powder Formulations Using Supercritical Fluid Technology. Pharmaceutical Research 21:1955-1969 (Nov. 2004).
Jørgensen, et al. Cholix toxin, a novel ADP-ribosylating factor from Vibrio cholerae. Journal of Biological Chemistry 283.16 (Apr. 18, 2008): 10671-10678.
Jung et al. Biodegradable nanoparticles for oral delivery of peptides: is there a role for polymers to affect mucosal uptake? EurJ Pharm Biopharm. Jul. 2000;50(1):147-60.
Karlin, et al. Applications and statistics for multiple high-scoring segments in molecular sequences. PNAS USA 90:5873-5877 (1993).
Karolewicz. A review of polymers as multifunctional excipients in drug dosage form technology. Saudi Pharmaceutical Journal 24(5):525-536 (2016). Available online Mar. 7, 2015.
Khan et al. Recent progress of drug nanoformulations targeting to brain. Journal of Controlled Release 291:37-64 (2018). Available online Oct. 9, 2018.
Kimball et al. Clinical and immunologic assessment of patients with psoriasis in a randomized, double-blind, placebo-controlled trial using recombinant human interleukin 10. Arch Dermatol 138:1341-6 (Oct. 2002).
Klukkert et al. Influence of Tableting on the Conformation and Thermal Stability of Trypsin as a Model Protein. Journal of Pharmaceutical Sciences 104(12):4314-4321 (2015). Published online Oct. 13, 2015.
Kornbluth et al. Ulcerative Colitis Practice Guidelines in Adults: American College of Gastroenterology, Practice Parameters Committee. American Journal of Gastroenterology 105(3):501-523 (2010). Published online Jan. 12, 2010.
Kounnas, et al. The alpha 2-macroglobulin receptor/low density lipoprotein receptor-related protein binds and internalizes Pseudomonas exotoxin A. Journal of Biological Chemistry 267.18 (1992): 12420-12423.
Kumar et al. Genome Sequence of Non-O1 Vibrio cholerae PS15. Genome Announcements 1(1):e00227-12 (Jan./Feb. 2013). 2 pages.
Larsen et al. Interleukin-1—Receptor Antagonist in Type 2 Diabetes Mellitus. N Engl J Med 356(15):1517-1526 (Apr. 12, 2007).
Lee et al. Impact of Regional Intestinal pH Modulation on Absorption of Peptide Drugs: Oral Absorption Studies of Salmon Calcitonin in Beagle Dogs. Pharmaceutical Research 16(8):1233-1239 (1999).
Lee et al. Nonclinical safety assessment of a human interleukin-22FCIG fusion protein demonstrates in vitro to in vivo and cross-species translatability. Pharmacol Res Perspect 2018:e00434 (2018). 13 pages. DOI: 10.1002/prp2.434.
Lee et al. Regional Differences in Intestinal Spreading and pH Recovery and the Impact on Salmon Calcitonin Absorption in Dogs. Pharmaceutical Research 17(3):284-290 (2000).
Lejeune et al. Interleukin-22 (IL-22) Activates the JAK/STAT, ERK, JNK, and p38 Map Kinase Pathways in a Rat Hepatoma Cell Line. Pathways that are Shared with and Distinct from IL-10. J Biol Chem 277(37):33676-33682 (Sep. 13, 2002). Published, JBC Papers in Press, Jun. 26, 2002, DOI 10.1074/jbc.M204204200.
Li et al. Increased Mucosal IL-22 Production of an IL-10RA Mutation Patient Following Anakinra Treatment Suggests Further Mechanism for Mucosal Healing. J Clin Immunol 37:104-107 (2017). DOI 10.1007/s10875-016-0365-3.
Li et al. Role of interleukin-22 in inflammatory bowel disease. World J Gastroenterol 20(48):18177-18188 (Dec. 28, 2014). DOI: 10.3748/wjg.v20.i48.18177.
Lim et al. Human Il-22 binding protein isoforms act as a rheostat for IL-22 signaling. Sci Signal 9(447):ra95 (Sep. 27, 2016). 12 pages. DOI: 10.1126/scisignal.aad9887.
Lin et al. Different Types of Cell Death Induced by Enterotoxins. Toxins 2:2158-2176 (Aug. 11, 2010). doi:10.3390/toxins2082158.
Lueben et al. Mucoadhesive Polymers in Peroral Peptide Drug Delivery. II. Carbomer and Polycarbophil Are Potent Inhibitors of the Intestinal Proteolytic Enzyme Trypsin. Pharmaceutical Research 12(9):1293-1298 (1995).
Lugo et al. The Father, Son and Cholix Toxin: the Third Member of the DT Group Mono-ADP-Ribosyltransferase Toxin Family. Toxins 7(8):2757-2772 (Jul. 24, 2015).
Magro et al. Third European Evidence-based Consensus on Diagnosis and Management of Ulcerative Colitis. Part 1: Definitions, Diagnosis, Extra-intestinal Manifestations, Pregnancy, Cancer Surveillance, Surgery, and Ileo-anal Pouch Disorders. J Crohns Colitis 11(6):649-670 (2017). Advance Access publication Feb. 2, 2017.
Maharaj et al. Simple rapid method for the preparation of enteric-coated microspheres. Journal of Pharmaceutical Sciences 73(1):39-42 (Jan. 1984).
Mahato et al. Emerging trends in oral delivery of peptide and protein drugs. Crit Rev Ther Drug Carrier Syst. 2003;20(2-3):153-214.
Marshall. Ilodecakin. Schering-Plough Corp. Drugs 2(10):1045-1048 (1999). 14 pages.
Mattoo et al. Interactions of bacterial effector proteins with host proteins. Curr Opin Immunol. Aug. 2007;19(4):392-401.
Mekalanos et al. Cholera toxin genes: nucleotide sequence, deletion analysis and vaccine development. Nature 306:551-557 (1983).
Mensink et al. How sugars protect proteins in the solid state and during drying (review): Mechanisms of stabilization in relation to stress conditions. European Journal of Pharmaceutics and Biopharmaceutics 114:288-295 (May 2017). Available online Feb. 9, 2017.
Merritt et al. Crystal structure of cholera toxin B-pentamer bound to receptor GM1 pentasaccharide. Protein Science 3:166-175 (1994).
Mühl et al. IL-22 in tissue-protective therapy. British Journal of Pharmacology 169:761-771 (2013).
Milling et al. Regulation of intestinal immunity: Effects of the oral adjuvant *Escherichia coli* heat-labile enterotoxin on heat-labile enterotoxin on migrating dendritic cells. Eur. J. Immunol. 37:87-99 (2007). DOI 10.1002/eji.200636199.
Mizoguchi. Healing of intestinal inflammation by IL-22. Inflamm Bowel Dis 18(9):1777-1784 (Sep. 2012). doi:10.1002/ibd.22929.
Mizoguchi. Clinical importance of IL-22 cascade in IBD. J Gastroenterol 53(4):465-474 (Apr. 2018). Epub Oct. 26, 2017. doi: 10.1007/s00535-017-1401-7.

(56) References Cited

OTHER PUBLICATIONS

Müller et al. Modulating the Th1/Th2 balance in inflammatory arthritis. Springer Semin Immunopathol 20(1-2):181-196 (1998).

Moroz, et al. Oral delivery of macromolecular drugs: Where we are after almost 100years of attempts. Adv Drug Deliv Rev. Jun. 1, 2016;101:108-121.

Mowat et al. Guidelines for the management of inflammatory bowel disease in adults. Gut 60(5):571-607 (2011). Published online Apr. 4, 2011.

Mowat et al. Regional specialization within the intestinal immune system. Nature Reviews Immunology 14:667-685 (Oct. 2014).

Mrsny. Breaking Through the Biological Barriers that Limit Protein Drug Delivery. Bangor University, United Kingdom (Presentation.) (Aug. 6, 2015.) 26 pages.

Mrsny. Breaking Through the Biological Barriers that Limit Protein Drug Delivery. (Presentation.) Controlled Release Society, Florence, Italy (Nov. 8, 2014.) 43 pages.

Mrsny. Breaking Through the Biological Barriers that Limit Protein Drug Delivery. (Presentation.) Tours, France (Jul. 2, 2015.) 25 pages.

Mrsny. Employing endogenous pathways for the oral delivery of biopharmaceuticals. (Presentation.) Reading, United Kingdom (Jul. 18, 2018.) 35 pages.

Mrsny, et al. Bacterial toxins as tools for mucosal vaccination. Drug Discovery Today. 2002; 4:247-258.

Mrsny et al. Mucosal administration of a chimera composed of Pseudomonas exotoxin and the gp120 V3 loop sequence of HIV-1 induces both salivary and serum antibody responses. Vaccine 17(11-12):1425-1433 (Mar. 17, 1999).

Mrsny. Harnessing Mucosal Immunology for Health. Bath, United Kingdom (Presentation.) (Sep. 25, 2018.) 29 pages.

Mrsny. Harnessing Mucosal Immunology for Health. Ma'alot-Tarshiha, Israel (Presentation.) (Oct. 7, 2018.) 28 pages.

Mrsny. It Starts With Asking Big Questions. Valencia, Spain (Presentation.) (Jul. 21, 2019.) 20 pages.

Mrsny, Lessons from nature: "Pathogen-Mimetic" systems for Mucosal Nano-medicines, Advanced Drug Delivery Reviews, vol. 61 :172-192 (online Dec. 24, 2008).

Mrsny. Molecular mechanisms of transcytosis pathways: Drug delivery thru epithelial and endothelial barriers. (Presentation.) (Dec. 3, 2010). 42 pages.

Mrsny. Molecular mechanisms of transcytosis pathways: Drug delivery thru epithelial and endothelial barriers. (Presentation.) Emory University, Atlanta, GA, United States. (Sep. 24, 2010). 51 pages.

Mrsny. Molecular mechanisms of transcytosis pathways: Drug delivery thru epithelial and endothelial barriers. (Presentation.) Nanomedicine and Drug Delivery Symposium (NanoDDS), University of Nebraska Omaha, Omaha, NE, United States. (Oct. 3, 2010.) 42 pages.

Mrsny. My Secondment(Gap Years?) at AMT. University of Bath, United Kingdom(Presentation.) (Oct. 6, 2017.) 20 pages.

Mrsny. Overcoming Barriers to Oral Protein Delivery. Boston, MA, United States (Presentation.) (Jul. 23, 2018.) 35 pages.

Mrsny. Overcoming Biological Barriers that Limit Peptide and Protein Drug Delivery. Berlin, Germany (Presentation.) (May 23, 2016.) 26 pages.

Mrsny. Overcoming Biological Barriers that Limit Peptide and Protein Drug Delivery. Denver, CO, United States (Presentation.) (Nov. 17, 2016.) 15 pages.

Mrsny. Overcoming Biological Barriers that Limit Peptide and Protein Drug Delivery. (Presentation.) (Jun. 14, 2016.) 36 pages.

Mrsny. Overcoming Biological Barriers that Limit Peptide and Protein Drug Delivery. University of California San Francisco, CA, United States (Presentation.) (Mar. 24, 2016.) 36 pages.

Mrsny. Paracellular and Transcellular Strategies to Enhance Oral Protein Delivery. (Presentation.) San Francisco, CA, United States (Mar. 15, 2013.) 41 pages.

Mrsny. Paracellular and Transcellular Strategies to Enhance Oral Protein Delivery. (Presentation.) Seoul, South Korea (Mar. 15, 2012.) 54 pages.

Mrsny. Paracellular and Transcellular Strategies to Enhance Oral Protein Delivery. (Presentation.) University of California, Santa Barbara, CA, United States. (Feb. 26, 2013.) 54 pages.

Mrsny. Permeation of barriers for GI and pulmonary drug delivery. (Presentation.) Gordon Research Conference, New Hampshire, United States. (Aug. 13, 2012.) 46 pages.

Mrsny. Prospects for Oral Delivery of Peptide and Protein Therapeutics. San Francisco, CA, United States (Presentation.) (May 21, 2018.) 29 pages.

Mrsny. Prospects for Oral Delivery of Peptide and Protein Therapeutics. University of Nottingham, United Kingdom(Presentation.) (Jun. 20, 2018.) 62 pages.

Mrsny. Strategies to Enhance the Oral Delivery of Therapeutic Proteins and Peptides. (Presentation.) Berlin, Germany. (Sep. 28, 2011.) 42 pages.

Mrsny. Strategies to Enhance the Oral Delivery of Therapeutic Proteins and Peptides. (Presentation.) Dunedin, New Zealand (Feb. 15, 2012). 42 pages.

Mrsny. Strategies to Enhance the Oral Delivery of Therapeutic Proteins and Peptides. (Presentation.) Nottingham, United Kingdom. (Sep. 2, 2011.) 42 pages.

Mrsny. Strategies to Enhance the Oral Delivery of Therapeutic Proteins and Peptides. (Presentation.) San Francisco, CA, United States. (Jun. 20, 2011.) 42 pages.

Mrsny. Strategies to Enhance the Oral Delivery of Therapeutic Proteins and Peptides. (Presentation.) The University of Sheffield, Sheffield, United Kingdom. (Jan. 16, 2012.) 42 pages.

Mrsny. TJ Regulation using Cell-Penetrating Peptides. (Presentation.) University of Copenhagen, Denmark (May 12, 2015.) 62 pages.

Mrsny. Understanding & Developing the Science Behind Oral Protein and Peptide Delivery. (Presentation.) Nottingham, United Kingdom (Jan. 22, 2014.) 48 pages.

Mrsny. Understanding & Developing the Science Behind Oral Protein Delivery: An Academic Case Study. (Presentation.) Berlin, Germany (Feb. 20, 2013.) 39 pages.

Mrsny. Understanding & Developing the Science Behind Oral Protein Delivery. (Presentation.) University of North Carolina at Chapel Hill, Chapel Hill, North Carolina, United States. (May 28, 2014.) 37 pages.

Mrsny. Understanding & Developing the Science Behind Oral Protein Delivery. (Presentation.) University of Westminster, London, United Kingdom. (Mar. 15, 2013). 40 pages.

Mrsny. Understanding & Developing the Science Behind Oral Protein Delivery. (Presentation.) Academy of Pharmaceutical Sciences, Edinburgh, United Kingdom.(Sep. 3, 2013). 40 pages.

Mrsny. Understanding & Developing the Science Behind Oral Protein Delivery. (Presentation.) University College Dublin, Dublin, Ireland (May 22, 2013). 44 pages.

Mrsny. Understanding & Developing the Science Behind Oral Protein Delivery. (Presentation.) University of East Anglia, Norwich, United Kingdom (Jun. 27, 2013). 43 pages.

Mrsny. Understanding Exotoxin Transcytosis for the Application of Oral Protein Delivery. Dresden, Germany (Presentation.) (Nov. 12, 2015.) 26 pages.

Mudrak et al. Heat-Labile Enterotoxin: Beyond GM1 Binding. Toxins 2:1445-1470 (Jun. 14, 2010). doi:10.3390/toxins2061445.

Mullis et al. Specific Enzymatic Amplification of DNA in Vitro: the Polymerase Chain Reaction. Cold Spring Harbor Symposia on Quantitative Biology. 1986;51:263-273.

Murata et al. Bifidobacterium breve MCC-117 Induces Tolerance in Porcine Intestinal Epithelial Cells: Study of the Mechanisms Involved in the Immunoregulatory Effect. Bioscience of Microbiota, Food and Health 33(1):1-10 (2014).

Nagalakshmi et al. Interleukin-22 activates STAT3 and induces IL-10 by colon epithelial cells. International Immunopharmacology 4:679-691 (2004).

Neurath. Current and emerging therapeutic targets for IBD. Nature Reviews Gastroenterology & Hepatology 14:269-278 (May 2017).

(56) References Cited

OTHER PUBLICATIONS

Neurath. Cytokines in inflammatory bowel disease. Nature Reviews Immunology 14:329-342 (May 2014).
Nguyen et al. STAT3-Activating Cytokines: A Therapeutic. Journal of Interferon & Cytokine Research 35(5):340-350 (May 5, 2015). Published online Mar. 11, 2015.
O'Farrell et al. IL-10 inhibits macrophage activation and proliferation by distinct signaling mechanisms: evidence for Stat3-dependent and -independent pathways. The EMBO Journal 17(4):1006-1018 (1998).
Pakula et al. Genetic Analysis of Protein Stability and Function. Annu. Rev. Genet. 23:289-310 (1989).
Parks et al. Interleukin-22 Signaling in the Regulation of Intestinal Health and Disease. Frontiers in Cell and Developmental Biology. vol. 3, Article 85 (Jan. 13, 2016). 13 pages.
Pastan et al. Recombinant Toxins as Novel Therapeutic Agents. Annu Rev Biochem 61:331-54 (1992).
PCT/US2019/060356 International Search Report and Written Opinion dated Apr. 8, 2020.
Porat. Accelerating Development of a Novel Chimera Protein through the Identification of a Two Column Purification Process Using NH2-750F and CaPure Resins. San Francisco, CA, United States.(Presentation.) (Nov. 7, 2018.) 30 pages.
Purdy et al. A Glimpse into the Expanded Genome Content of Vibrio cholerae through Identification of Genes Present in Environmental Strains. Journal of Bacteriology 187(9):2992-3001 (May 2005). DOI: 10.1128/JB.187.9.2992-3001.2005.
Purdy et al. Diversity and distribution of cholix toxin, a novel ADP-ribosylating factor from Vibrio cholerae. Environmental Microbiology Reports 2(1):198-207 (Feb. 2010). First published Feb. 8, 2010. DOI: https://doi.org/10.1111/j.1758-2229.2010.00139.x.
Roberts. Therapeutic protein aggregation: mechanisms, design, and control. Trends in Biotechnology 32(7):372-380 (Jul. 2014).
Rodighiero, et al. Structural Basis for the Differential Toxicity of Cholera Toxin and *Escherichia coli* Heat-labile Enterotoxin. The Journal of Biological Chemistry 274.77 (1999): 3962-3969.
Roszak et al. Survival strategies of bacteria in the natural environment. Microbiol Rev. Sep. 1987; 51(3): 365-379.
Rubas et al. Flux Measurements across Caco-2 Monolayers May Predict Transport in Human Large Intestinal Tissue. J Pharm Sci 85(2):165-169 (Feb. 1996).
Sabat et al. Therapeutic opportunities of the IL-22-IL-22R1 system. Nature Reviews Drug Discovery 13:21-38 (Jan. 2014).
Saidi et al. Prevalence of Vibrio cholerae O1 El Tor variant in a cholera-endemic zone of Kenya. Journal of Medical Microbiology 63:415-420 (2014). First published online Mar. 1, 2014. doi:10.1099/jmm.0.068999-0.
Sarnovsky, et al. Initial characterization of an immunotoxin constructed from domains II and III of cholera exotoxin. Cancer Immunol. Immunother., 59.5 2010 (published online Nov. 2009):737-746.
Shabgah et al. Interleukin-22 in human inflammatory diseases and viral infections. Autoimmunity Reviews 16:1209-1218 (2017). Available online Oct. 14, 2017.
Simmons et al. Immunomodulation Using Bacterial Enterotoxins. Scand J Immunol 53:518-226 (2001).
Simon, et al. Novel bacterial ADP-ribosylating toxins: structure and function. Nature Reviews Microbiology 12.9 (2014): 599-611.
Sims et al. The IL-1 family: regulators of immunity. Nature Reviews Immunology 10:89-102 (Feb. 2010). Published online Jan. 18, 2010.
Sonnenberg et al. Border patrol: regulation of immunity, inflammation and tissue homeostasis at barrier surfaces by IL-22. Nature Immunology 12(5):383-390 (May 2011). Published online Apr. 19, 2011. doi:10.1038/ni.2025.
Spooner et al. Retrograde transport pathways utilised by viruses and protein toxins. Virology Journal, 3:26 (2006).
Stefanich et al. Pre-clinical and translational pharmacology of a human interleukin-22 IgG fusion protein for potential treatment of infectious or inflammatory diseases. Biochemical Pharmacology 152:224-234 (2018). Available online Mar. 31, 2018. DOI: https://doi.org/10.1016/j.bcp.2018.03.031.
Sugimoto et al. IL-22 ameliorates intestinal inflammation in a mouse model of ulcerative colitis. J Clin Invest 118(2):534-544 (Feb. 2008). doi: 10.1172/JCI33194.
Sun et al. Cholera toxin B subunit: An efficient transmucosal carrier-delivery system for induction of peripheral immunological tolerance. Proc Natl Acad Sci USA 91:10795-10799 (Nov. 1994).
Tachiiri et al. Genomic structure and inducible expression of the IL-22 receptor a chain in mice. Genes and Immunity 4:153-159 (2003). doi:10.1038/sj.gene.6363934.
Taverner et al. Cholix protein domain I functions as a carrier element for efficient apical to basal epithelial transcytosis. Tissue Barriers, pp. 1710429-1 to 1710429-1 (Jan. 13, 2020). doi: 10.1080/21688370.2019.1710429.
Tokuriki et al. Stability effects of mutations and protein evolvability. Curr. Opin. Struc. Biol. 19:596-604 (2009).
Veas et al. Chapter 4: IL-22 Induces an Acute-Phase Response Associated to a Cohort of Acute Phase Proteins and Antimicrobial Peptides as Players of Homeostasis, pp. 85-104. Acute Phase Proteins—Regulation and Functions of Acute Phase Proteins. Published online Oct. 3, 2011. ISBN: 978-953-307-252-4, InTech.
Wang et al. Interleukin-22 alleviates metabolic disorders and restores mucosal immunity in diabetes. Nature 514:237-241 (Oct. 9, 2014). Published online Aug. 6, 2014. doi: 10.1038/nature13564.
Wang et al. Methods to determine intestinal permeability and bacterial translocation during liver disease. J Immunol Methods 421:44-53 (Jun. 2015). Epub Jan. 13, 2015. doi:10.1016/j.jim.2014.12.015.
Weiss et al. Cloning of murine IL-22 receptor alpha 2 and comparison with its human counterpart. Genes and Immunity 5:330-336 (2004). Published online Jun. 17, 2004. doi:10.1038/sj.gene.6364104.
Wileman, et al. Receptor-mediated endocytosis. Biochemical Journal 232.1 (1985): 1-14.
Wingfield. N-Terminal Methionine Processing. Curr Protoc Protein Sci 88:6.14.1-6.14.3 (2017). First published Apr. 3, 2017. doi:10.1002/cpps.29.
Wolk et al. Deficiency of IL-22 Contributes to a Chronic Inflammatory Disease: Pathogenetic Mechanisms in Acne Inversa. J Immunol 186:1228-1239 (2011). Prepublished online Dec. 8, 2010. doi: 10.4049/jimmunol.0903907.
Wolk et al. Is there an interaction between interleukin-10 and interleukin-22? Genes and Immunity 6:8-18 (2005).
Wolk et al. Cutting edge: immune cells as sources and targets of the IL-10 family members? J Immunol 168(11):5397-5402 (2002).
Woodley, J.F. Enzymatic barriers for GI peptide and protein delivery. Crit Rev Ther Drug Carrier Syst. 1994;11(2-3):61-95.
Wu. Identification of Endoplasmic Reticulum Export Motifs for G Protein-Coupled Receptors. Methods in Enzymol 521:189-202 (2013). DOI: https://doi.org/10.1016/6978-0-12-391862-8.00010-7.
Xu et al. IL-22 secreting CD4+ T cells in the patients with neuromyelitis optica and multiple sclerosis. J Neuroimmunol 261(1-2):87-91 (Aug. 15, 2013). Epub May 28, 2013. doi: 10.1016/j.jneuroim.2013.04.021.
Yahiro et al. Cholix toxin, an eukaryotic elongation factor 2 ADP-ribosyltransferase, interacts with Prohibitins and induces apoptosis with mitochondrial dysfunction in human hepatocytes. Cell Microbiol. Aug. 2019;21(8):e13033.doi: 10.1111/cmi.13033. Epub May 14, 2019.
Yates, et al. Stealth and Mimicry by Deadly Bacterial Toxins. Trends Biochemical Science 31 (2006): 123-133.
Zdanov. Structural analysis of cytokines comprising the IL-10 family. Cytokine & Growth Factor Reviews 21(5):325-330 (Oct. 2010). Available online Sep. 16, 2010. DOI: https://doi.org/10.1016/j.cytogfr.2010.08.003.
Zenewicz et al. IL-22 but not IL-17 provides protection to hepatocytes during acute liver inflammation. Immunity 27(4): 647-659 (Oct. 2007).

(56) References Cited

OTHER PUBLICATIONS

Zenewicz et al. Innate and adaptive interleukin-22 protects mice from inflammatory bowel disease. Immunity 29(6):947-957 (Dec. 19, 2008). doi:10.1016/j.immuni.2008.11.003.

* cited by examiner

| Group | Route frequency | Dose |
|---|---|---|
| Naive | p.o., q.d. | NA |
| Vehicle | p.o., q.d. | 10 mg/mL SBTI in bicarb |
| Cyclosporine A (model positive control) | p.o., q.d. | 75 mg/kg |
| rhIL-22 | i.p., q.d. | 4 mg/kg |
| SEQ ID NO: 15 | p.o., q.d. | 1 mg/kg |
| SEQ ID NO: 15 | p.o., q.d. | 30 mg/kg |

| Parameter | Acute Dosing | Subchronic Dosing |
|---|---|---|
| Cmax | 1711 ng/ml | 1409 ng/ml |
| Tmax | 30 min | 30 min |
| $AUC_{0-24}$ | 2796 (ng/ml)xh | 2454 (ng/ml)xh |

MW: 48 kDa
Theoretical pI: 5.5
Disulfide bonds: 4

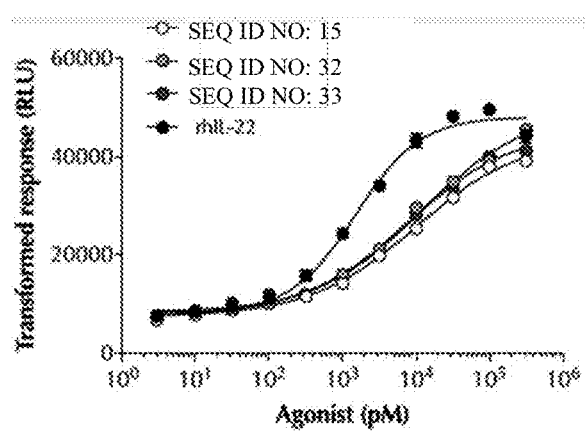 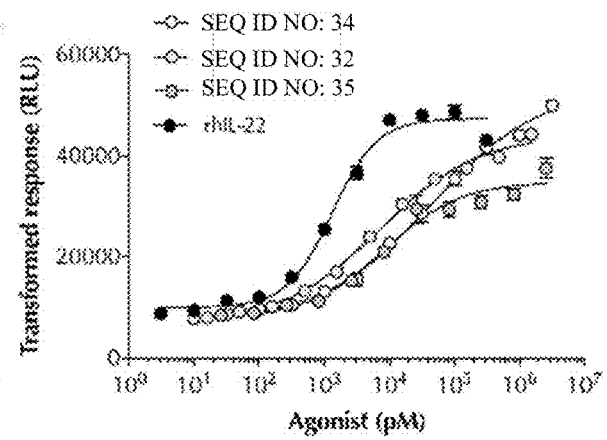
FIG. 27A                FIG. 27B
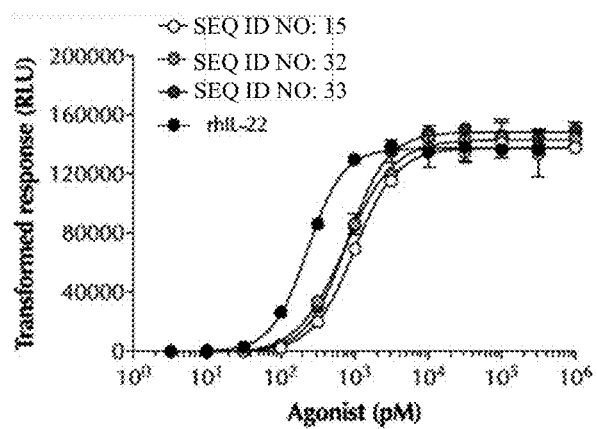 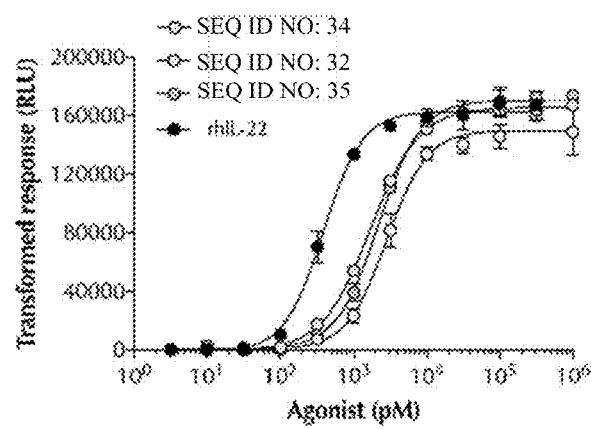
FIG. 27C                FIG. 27D

DELIVERY CONSTRUCTS FOR TRANSCYTOSIS AND RELATED METHODS

CROSS-REFERENCE

This application is a Continuation Application of International Application No. PCT/US2019/060356, filed Nov. 7, 2019, which claims the benefit of U.S. Provisional Application No. 62/756,889, filed Nov. 7, 2018, U.S. Provisional Application No. 62/888,133, filed Aug. 16, 2019, and U.S. Provisional Application No. 62/888,238 filed Aug. 16, 2019, which applications are incorporated herein by reference in their entirety.

BACKGROUND

The gut epithelium has thwarted efforts to orally administer large therapeutic molecules such as proteins because proteins cannot diffuse across the intact epithelial barrier or cross the barrier through the tight junctions. Once taken up by an epithelial cell, a therapeutic protein can enter the destructive lysosomal trafficking pathway, or can be released back into the intestinal lumen. This inability to be readily transported across the intestinal epithelium can be a limiting factor in developing commercially viable oral formulations, particularly for polypeptide-based therapeutics.

Parenteral administration such as intravenous or subcutaneous administration can be a solution, but these administration routes can often create considerable side effects, lower the therapeutic efficacy, and reduce patient convenience that can negatively affect compliance. There is a need for improved compositions and methods for transporting therapeutics across an epithelium, e.g., a gut epithelium.

Additionally, purification and refolding of biologically active polypeptides in order to obtain correctly folded, biologically active, and stable polypeptides in high yields and with low endotoxin levels is still considered one of the most challenging aspects for a cost- and resource-effective production of biological therapeutics (e.g., polypeptides). Thus, there is also a need for improved methods for the production (fermentation, refolding, purification, and formulation) of such biologically active molecules.

SUMMARY

In the various aspects, the present disclosure provides a delivery construct comprising an amino acid sequence set forth in SEQ ID NO: 15 or SEQ ID NO: 17, or an amino acid sequence having at least 90%, 95% or 99% sequence identity thereto.

In the various aspects, the present disclosure provides a delivery construct comprising a carrier consisting of an amino acid sequence set forth in SEQ ID NO: 7 or SEQ ID NO: 9. In some instances, the carrier is coupled to a heterologous payload. In some instances, the heterologous payload is a human IL-22. In some instances, the human IL-22 consists of an amino acid sequence set forth in SEQ ID NO: 11. In some instances, the carrier is coupled covalently or non-covalently to the IL-22. In some instances, the carrier is coupled covalently to the IL-22 via a spacer. In some instances, the spacer consists of an amino acid sequence set forth in SEQ ID NO: 13. In some instances, the delivery construct consists of an amino acid sequence set forth in SEQ ID NO: 15 or SEQ ID NO: 17.

Provided herein is a method of treating an inflammatory disease in a subject, the method comprising administering to the subject an effective amount of a delivery construct described herein (e.g., SEQ ID NO: 15 or SEQ ID NO: 17). In some instances, the inflammatory disease is hepatitis, obesity, fatty liver disease, liver inflammation, or pancreatitis, Crohn's disease, ulcerative colitis, pouchitis, proctitis, multiple sclerosis, systemic lupus erythematosus, graft versus host disease, rheumatoid arthritis, or psoriasis. In some instances, the disease is Crohn's disease or ulcerative colitis.

Described herein, in certain embodiments, are methods for obtaining a purified non-naturally occurring fusion protein, the method comprising: performing anion exchange chromatography on a mixture comprising the non-naturally occurring fusion protein to obtain a first fraction comprising the non-naturally occurring fusion protein; wherein the non-naturally occurring fusion protein comprises IL-22 and a carrier. In some embodiments, wherein performing anion exchange chromatography comprises binding the non-naturally occurring fusion protein to anionic exchange resin and providing an increasing salt gradient for subsequent elution of the non-naturally occurring fusion protein to obtain the first fraction. In some embodiments, performing anion exchange chromatography comprises contacting the mixture with a resin comprising amine-functionalized polymethacrylate beads. In some embodiments, the resin is an $NH_2$-750F resin.

In some embodiments, the method further comprises refolding the non-naturally occurring fusion protein prior to performing anion exchange chromatography. In some embodiments, refolding the non-naturally occurring fusion protein comprises contacting chaotrope-solubilized protein from inclusion bodies with a refolding solution, wherein the refolding solution comprises: arginine (0.75 M to 1.25 M); glycerol (2% to 20% v/v); cysteine (0.5 mM to 10 mm); and cystamine (0.2 mM to 10 mM); wherein the refolding solution has a pH of between 7.5 and 8.5. In some embodiments, the arginine is present in the refolding solution at a concentration of between 0.9 M and 1.1 M; glycerol is present in the refolding solution at a concentration of between 7% and 13% (w/w); cysteine is present in the refolding solution at a concentration of between 1.5 mM and 6 mM; cystamine is present in the refolding solution at a concentration of between 0.6 mM and 3 mM; and the refolding solution has a pH of between 7.8 and 8.2.

In some embodiments, the method further comprises subjecting a sample comprising the first fraction to a hydroxyapatite resin to obtain a second fraction comprising the non-naturally occurring fusion protein. In some embodiments, the hydroxyapatite resin is a CaPure-hydroxyapatite resin. In some embodiments, the method further comprises performing cation exchange chromatography on a sample comprising the first fraction. In some embodiments, performing cation exchange chromatography comprises contacting the sample comprising the first fraction with a resin comprising sulfate-functionalized polymethacrylate beads. In some embodiments, the resin is a TOYOPEARL Sulfate-650F resin.

In some embodiments, upon contact with a cell, the carrier promotes endocytosis or transcytosis of the non-naturally occurring fusion protein. In some embodiments, upon contact with the cell, the carrier promotes transcytosis of the non-naturally occurring fusion protein. In some embodiments, the cell is a gut epithelial cell. In some embodiments, the gut epithelial cell is a polarized gut epithelial cell. In some embodiments, the carrier is a truncated variant of a naturally occurring or non-naturally occurring cholix polypeptide. In some embodiments, the carrier has at least 70%, 80%, 85%, 90%, 95%, 98%, 99%, or 100% sequence identity to any one of SEQ ID NOS: 1, 2, 3, 4, 5, 6, 7, 8, 9, 22, or 23. In some embodiments, the non-naturally occurring fusion protein has at least 70%, 80%, 85%, 90%, 95%, 98%, 99%, or 100% sequence identity to the sequence of any one of SEQ ID NOS: 14-21. In some embodiments, IL-22 has at least 85%, 90%, 95%, 98%, 99% or 100% sequence identity to any one of SEQ ID NOS: 10, 11, or 12.

In some embodiments, the carrier, by itself, has a first isoelectric point (pI) and the IL-22, by itself, has a second isoelectric point, wherein the first isoelectric point is at least 1 pH unit, at least 1.5 pH units, at least 1.7 pH units, or at least 2 pH units lower than the second isoelectric point. For instance, in some embodiments, the carrier has a pI of between 4.8 and 5.4, between 4.9 and 5.3, between 5.0 and 5.2, such as a pI of about 5.1. In some embodiments, the pI of the IL-22 is between about 6.8 and 7.4, such as between about 6.9 and 7.3, between about 7.0 ant 7.2, such as about 7.1. In some embodiments, the non-naturally occurring fusion protein is obtained by any of the methods described herein.

Described herein, in certain embodiments, are methods of refolding a non-naturally occurring fusion protein comprising a carrier and IL-22, the method comprising: (i) contacting inclusion bodies comprising the non-naturally occurring fusion protein with a solubilization solution comprising a chaotropic agent to produce a soluble non-naturally occurring fusion protein; (iii) contacting the non-naturally occurring fusion protein with a refolding solution, wherein the refolding solution comprises: arginine (0.75 M to 1.25 M); glycerol (2% to 20% v/v); cysteine (0.5 mM to 10 mm); and cystamine (0.2 mM to 10 mM); wherein the refolding solution has a pH of between 7.5 and 8.5.

In some embodiments, arginine is present in the refolding solution at a concentration of between 0.9 M and 1.1 M; glycerol is present in the refolding solution at a concentration of between 7% and 13% (w/w); cysteine is present in the refolding solution at a concentration of between 1.5 mM and 6 mM; cystamine is present in the refolding solution at a concentration of between 0.6 mM and 3 mM; and the refolding solution has a pH of between 7.8 and 8.2.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 21A illustrates a size-exclusion chromatograph following a first column purification of SEQ ID NO: 15 using anion exchange resin $NH_2$-750F with a column volume of 10 mL and a bed height of 20 cm. FIG. 21B illustrates a size-exclusion chromatograph following a first column purification of SEQ ID NO: 15 using anion exchange resin $NH_2$-750F with column volume of 4.6 L and a bed height of 30 cm.

FIG. 22A illustrates a size exclusion chromatograph following a second column purification of SEQ ID NO: 15 using hydroxyapatite resin $Ca^{++}$Pure with a column volume of 5 mL, a bed height of 10 cm, and a gradient of 0-25% B, 25 C. FIG. 22B illustrates a size exclusion chromatograph following a second column purification of SEQ ID NO: 15 using hydroxyapatite resin CaPure® with a column volume of 800 mL, a bed height of 21 cm, and a gradient of 0-25% B, 25CV. For each figure a corresponding SDS-PAGE of samples from the different fractions eluted from the CaPure® resin.

FIG. 23A illustrates an LC-MS chromatograph of SEQ ID NO: 17. Peak 1 illustrates correctly refolded SEQ ID NO: 17. FIG. 23B illustrates an LC-MS chromatograph of SEQ ID NO: 15. Peak 1 illustrates corrected refolded SEQ ID NO: 15. Peak 2 illustrates SEQ ID NO: 15 with the terminal methionine cleaved (illustrated by SEQ ID NO: 20). Peak 3 illustrates SEQ ID NO: 15 with the terminal methionine cleaved (illustrates by SEQ ID NO: 20) and acetylation of the resulting N-terminal amino acid.

FIG. 25A illustrates total IL-22 plasma concentration as a function of time after administration of the delivery construct of SEQ ID NO: 15. FIG. 25B illustrates IL-22BP plasma concentration as a function of time after administration of the delivery construct of SEQ ID NO: 15.

FIGS. 27A-27D illustrate that spacer length and coupling of payload to the N- or C-terminus of a carrier does not significantly affect a payload's biological activity. FIG. 27A illustrates the length of various amino acid spacers did not affect the induction of IL-22 receptor dimerization. FIG. 27B illustrates that coupling the IL-22 payload to the N- or C-terminus of a carrier did not affect induction of IL-22 dimerization. FIG. 27C illustrates the length of various amino acid spacers did not affect induction of pSTAT3 activation. FIG. 27D illustrates that coupling the IL-22 payload to the N- or C-terminus of a carrier did not affect induction of pSTAT3 activation.

DETAILED DESCRIPTION

Figure 1:
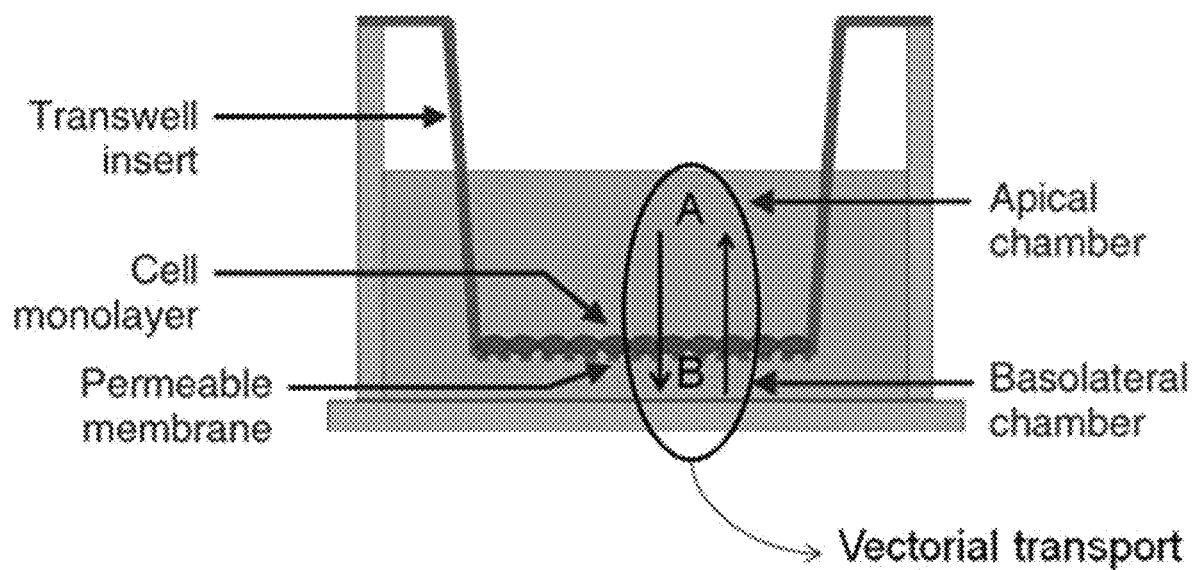
FIG. 1 schematically shows a setup comprising an apical chamber above an epithelial cell monolayer and a basal chamber below such epithelial cell monolayer. For apical to basolateral permeability, test articles (e.g., delivery constructs, payloads, etc.) were applied to the apical (A) side and the amount of permeated (e.g., transcytosed) material was determined on the basolateral (B) side.
Figure 2:
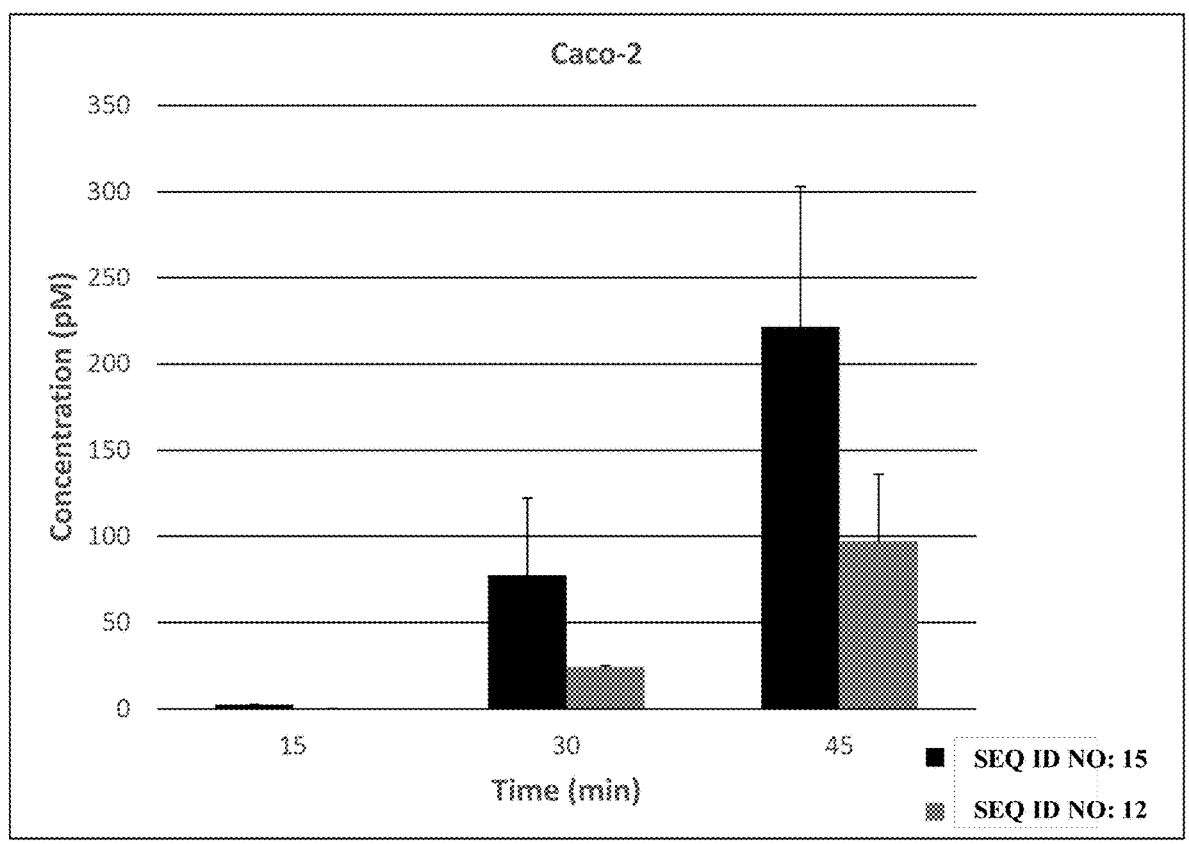
FIG. 2 shows that a delivery construct (SEQ ID NO: 15), which includes a carrier (SEQ ID NO: 7) coupled to an IL-22 (SEQ ID NO: 11) via a spacer (SEQ ID NO: 13), transported the IL-22 payload across intact, polarized, Caco-2 gut epithelial cell monolayers in a time-dependent manner (the amount of protein on the basolateral site was measured 15, 30, and 45 minutes after the delivery construct was applied to the basal membrane of the monolayer as described above in FIG. 1). The data further shows that when the delivery construct with a carrier of SEQ ID NO: 7 and IL-22 (SEQ ID NO: 11) is applied to the to the Caco-2 epithelial cells, about 2-3 fold more IL-22 crossed the Caco-2 epithelial cell monolayer as compared to when an IL-22 (SEQ ID NO: 12) was not coupled to a carrier.
Figure 3:
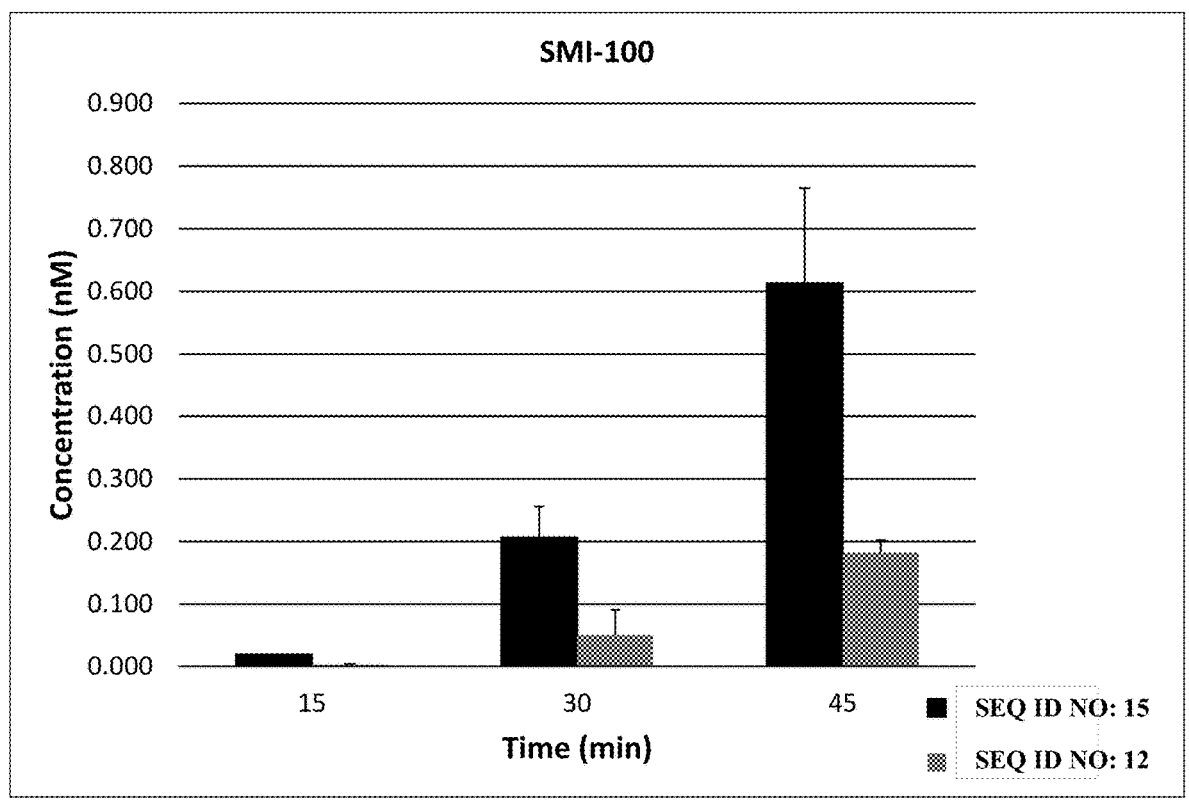
FIG. 3 shows that a delivery construct (SEQ ID NO: 15) resulted in IL-22 (SEQ ID NO: 11) being transported across intact and polarized SMI-100 gut epithelial cell monolayers in a time-dependent manner (the amount of protein in the basolateral chamber was measured at 15, 30, and 45 minutes after the delivery construct was applied to the basal membrane of the monolayer). The data further shows that when the delivery construct including the carrier with SEQ ID NO: 7 coupled to IL-22 (SEQ ID NO: 11) is applied to the SMI-100 epithelial cells, about 2-3 fold more IL-22 crossed the SMI-100 epithelial cell monolayer as compared to when an IL-22 (SEQ ID NO: 12) was not coupled to a carrier.
Figure 4:
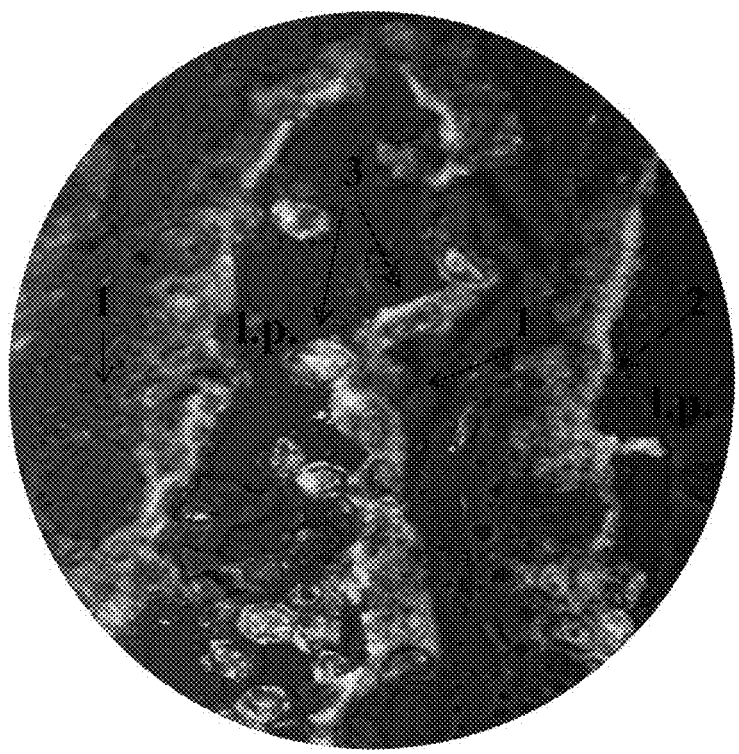
FIG. 4 demonstrates that a delivery construct (SEQ ID NO: 15) including a carrier (SEQ ID NO: 7) coupled to an IL-22 (SEQ ID NO: 11) via a spacer (SEQ ID NO: 13) results in IL-22 being transported in significant amounts across an intact and polarized gut epithelium in vivo. The apical site of the gut epithelium is highlighted by white arrow #1. The lamina propria is abbreviated as "l.p." The outer basal membrane of the polarized epithelium is highlighted by white arrow #2. IL-22 localization is indicated white arrow #3).
Figure 5A:
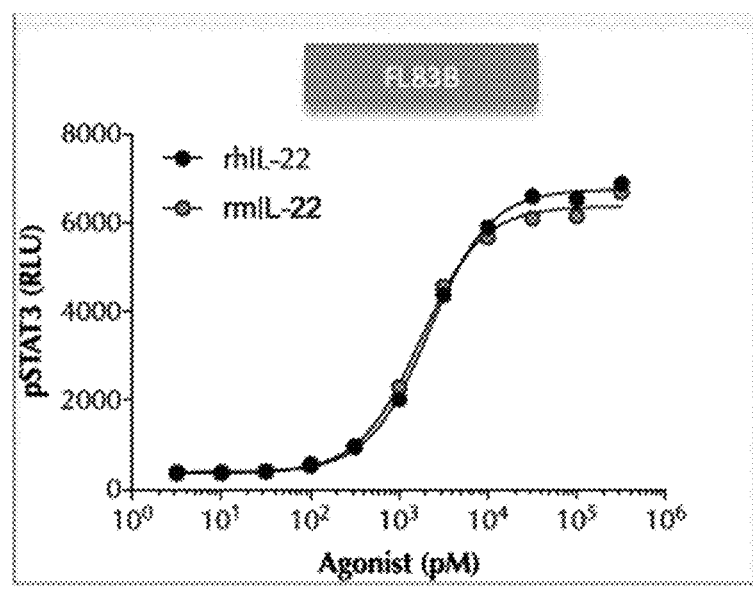
FIG. 5A demonstrates STAT3 phosphorylation in murine FL83 B cells as a function of agonist concentration (in pM), wherein the agonist is recombinant human IL-22 (rhIL-22, SEQ ID NO: 12) or recombinant murine IL-22 (rmIL-22; MAVLQKSMSFSLMGTLAASCLLLIALWAQE ANALPVNTRCKLEVSNFQQPYIVNRTFMLAKEAS-LADNNTDVRLIGEKLFRGVSAKDQCYL MKQVLNF-TLEDVLLPQ SDRFQPYMQEVVPFLTKLSNQL S SCHISGDDQNIQKNVRRLKETV KKLGE-SGEIKAIGELDLLFMSLRNACV (SEQ ID NO: 30)). The data show that rhIL-22 and rmIL-22 induced STAT3 phosphorylation in a concentration-dependent manner, demonstrating that the human IL-22 protein can bind and induce signal transduction through mouse IL-22 receptors as effectively as mouse IL-22.
Figure 5B:
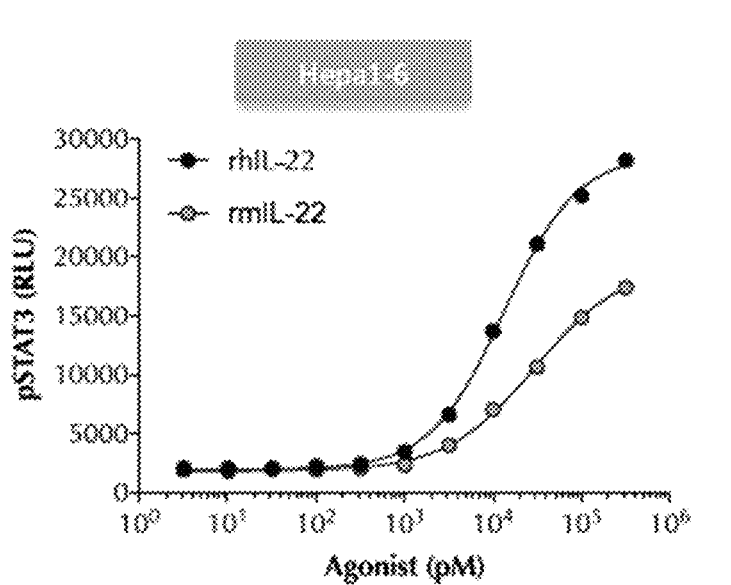
FIG. 5B demonstrates that rhIL-22 (SEQ ID NO: 12) and rmIL-22 also induced STAT3 phosphorylation in murine Hepa1-6 cells.
Figure 6A:
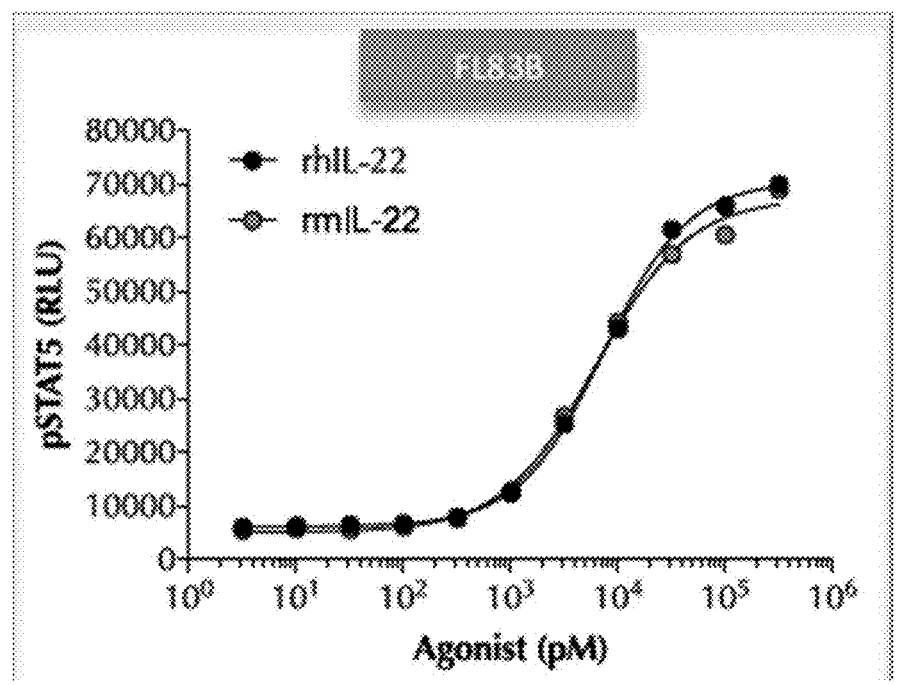
FIG. 6A demonstrates that rhIL-22 (SEQ ID NO: 12) and rmIL-22 induced STAT5 phosphorylation in murine FL83 B cells in a dose-dependent manner, demonstrating that the human IL-22 protein can bind and induce signal transduction through mouse IL-22 receptors as effectively as mouse IL-22.
Figure 6B:
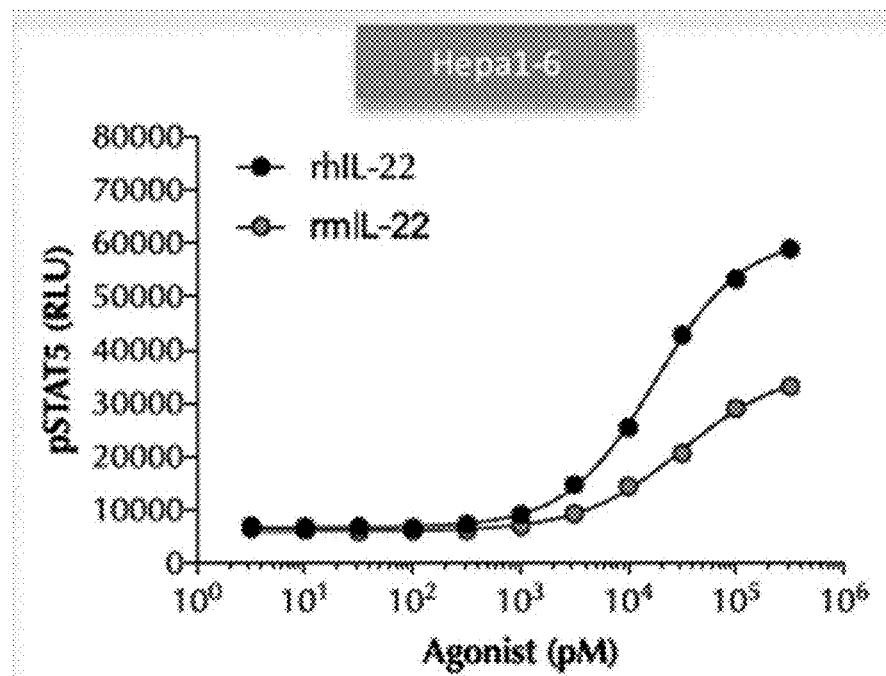
FIG. 6B demonstrates that rhIL-22 (SEQ ID NO: 12) and rmIL-22 also induced STAT5 phosphorylation in murine Hepa1-6 cells.

The present disclosure describes non-naturally occurring fusion proteins (e.g. delivery constructs capable of transporting one or more heterologous payload molecules) and methods for the refolding and purification of non-naturally occurring fusion proteins. For example, the non-naturally occurring fusion protein can be an IL-22 delivery construct described herein.

The below terms are discussed to illustrate meanings of the terms as used in this specification, in addition to the understanding of these terms by those of skill in the art. As used herein and in the appended claims, the singular forms "a," "an," and, "the" include plural referents unless the context clearly dictates otherwise. It is further noted that the claims can be drafted to exclude any optional element. As such, this statement is intended to serve as antecedent basis for use of such exclusive terminology as "solely," "only," and the like in connection with the recitation of claim elements, or use of a "negative" limitation.

Certain ranges or numbers are presented herein with numerical values being preceded by the term "about." The term "about" is used herein shall mean plus or minus 1%, 2%, 3%, 4%, or 5% of the number that the term refers to. As used herein, the terms "subject" and "individual," are used interchangeably and can be any animal, including mammals (e.g., a human or non-human animal).

As used herein, the terms "treat," "treating," or "treatment," and other grammatical equivalents, include alleviating, abating or ameliorating one or more symptoms of a disease or condition, ameliorating, preventing or reducing the appearance, severity or frequency of one or more additional symptoms of a disease or condition, ameliorating or preventing the underlying causes of one or more symptoms of a disease or condition, inhibiting the disease or condition, such as, for example, arresting the development of the disease or condition, relieving the disease or condition, causing regression of the disease or condition, relieving a condition caused by the disease or condition, or inhibiting the symptoms of the disease or condition either prophylactically and/or therapeutically.

As described herein, the term "percent (%) sequence identity," and terms related thereto, in the context of amino acid sequences, is the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as Clustal Omega, BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

The terms "polypeptide" and "protein" are used interchangeably herein to refer to a polymer of amino acid residues. Peptides also include essentially any polyamino acid including, but not limited to, peptide mimetics such as amino acids joined by an ether as opposed to an amide bond.

Payloads and Delivery Constructs

Provided herein are delivery constructs capable of transporting one or more heterologous payload molecules (e.g., one or more therapeutic payloads) across epithelial cells (e.g., polarized gut epithelial cells) and into the lamina propria via transcytosis. The delivery constructs can comprise a carrier coupled to a heterologous payload. The delivery construct can be a non-naturally occurring fusion protein. The carrier can be capable of transporting the heterologous payload across polarized epithelial cells (e.g., polarized gut epithelial cells) using endogenous trafficking pathways. Utilization of endogenous trafficking pathways, as opposed to use of passive diffusion, can allow the carrier to shuttle the heterologous payload rapidly and efficiently across epithelial cells without impairing the barrier function of these cells or the biological activity of the heterologous payload. Further provided herein are methods for purification and refolding of the delivery constructs described herein.

A carrier herein may be derived from a polypeptide secreted by a bacterium. Such carrier may be derived from a polypeptide secreted from *Vibrio cholerae* or *Pseudomonas aeruginosa*. The polypeptide secreted by *Vibrio cholerae* can be a Cholix polypeptide. A carrier derived from a Cholix polypeptide can be naturally occurring or non-naturally occurring. For example, a non-naturally occurring Cholix polypeptide can consist of the amino acid sequence set forth in SEQ ID NO: 1 (an example of a Cholix$^{1-634}$) (TABLE 1). A carrier derived from a Cholix polypeptide can be a truncated and/or mutated variant of a polypeptide derived from Cholix. For example, the carrier can comprise or consist of an amino acid sequence of those with amino acid residues 1-206, 1-245, 1-251, 1-266, and 1-386 of SEQ ID NO: 1 or SEQ ID NO: 26. In some instances, such carriers have an amino acid sequence of those with amino acid residues 1-206, 1-245, 1-251, 1-266, and 1-386 of SEQ ID NO: 4. Mutation(s) can include one or more substitution(s), deletion(s), and/or addition(s). For example, a carrier herein can comprise a V1L substitution. Stated differently, in some embodiments, the cholix-related carrier has a leucine amino acid at position "1." (Position 1 refers to the first amino acid of variants that do not have an N-terminal methionine or the second position in variants that include an N-terminal methionine. In other words, in determining the length of a carrier, an N-terminal methionine, if present, is ignored.) In some embodiments, carriers comprising the V1L substitution experience reduced or eliminated cleavage of the N-terminal amino acid. In some embodiments, carriers comprising the V1L substitution experience reduced or eliminated acetylation of the N-terminal amino acid. A carrier provided herein can have a reduced (e.g., at least 50% reduced) or ablated ADP ribosylation activity (e.g., ribosylation of elongation factor 2) relative to a naturally-occurring Cholix variant. In some embodiments, the carrier can comprise an N-terminal methionine. In other embodiments, no N-terminal methionine is present.

A truncated Cholix carrier can consist of, consist essentially of, or comprise amino acid residues 1-386 of a sequence set forth in SEQ ID NO: 26 (FORMULA I). A truncated Cholix carrier can consist of, consist essentially of, or comprise amino acid residues 1-266 of a sequence set forth in SEQ ID NO: 26 (FORMULA I). In such instances, a carrier can consist of, consist essentially of, or comprise amino acid residues 1-266 of a sequence set forth in SEQ ID NO: 1. Thus, in some instances, the carrier consists of the amino acid sequence set forth in SEQ ID NO: 2 (an example of Cholix$^{1-386}$) or SEQ ID NO: 3 (an example of Cholix$^{1-266}$). In some instances, a carrier has the amino acid sequence represented by SEQ ID NO: 2 with a V1L substitution. Thus, in some instances, the carrier consists of the amino acid sequence set forth in SEQ ID NO: 4 (an example of V1L-Cholix$^{1-386}$) or SEQ ID NO: 5 (an example of V1L Cholix$^{1-266}$). Any of these carriers can include one or more amino acids at its N-terminus for expression in various microorganisms (e.g., bacteria), e.g., an N-terminal methionine. Such carrier can have an amino acid sequence set forth in SEQ ID NOS: 6-9.

The Cholix polypeptide can be a protein comprising, consisting essentially of, or consisting of an amino acid sequence having at least 80%, 85%. 90%, 95%, 98%, or 99% sequence identity, or having 100% sequence identity, to an amino acid sequence set forth in any one of SEQ ID NOS: 1-9 or SEQ ID NOS: 22-23. An example of a Cholix polypeptide is provided herein as SEQ ID NO: 1. or SEQ ID NO: 22. Also contemplated herein are truncated Cholix polypeptide variants that are able to transport a payload across polarized epithelia cells (e.g., polarized gut epithelial cells). Such Cholix polypeptides can be truncated at any one of the amino acid positions from 206 to 633 as compared to a reference sequence, e.g. SEQ ID NO: 1, SEQ ID NO: 22, or SEQ ID NO: 26, or an amino acid sequence having at least 80%, 85%, 90%, 95%, 98% or 99% sequence identity thereto.

Also contemplated herein are delivery constructs comprising carriers having high sequence identity to the sequences above. Such high sequence identity can include, at least 90%, 95%, 96%, 97%, 98% or 99% sequence identity. Thus, in some instances, the carrier comprises a sequence identify of at least 90%, 95%, 96%, 97%, 98% or 99% sequence identity to an amino acid sequence set forth in SEQ ID NO: 6-9.

A carrier contemplated herein can be coupled to a payload, such as a heterologous payload. Such payload can be a therapeutic payload. A therapeutic payload can be a cytokine, a hormone, a growth factor, a therapeutic antibody, an antigen, a functional fragment of any of the above, or any other protein that has biological, therapeutic activity, or a protein that may be deficient in a subject (e.g., a genetic/ inherited deficiency of a certain protein). Cytokines contemplated herein include monomeric chemokines and interleukins (also abbreviated herein as "ILs"). The interleukin can be IL-22. The interleukin may be from any species (e.g., from a human or a rodent). The interleukin may be a human interleukin. Human IL-22 can have the amino acid sequence set forth in SEQ ID NO: 10 (IL-22$^{1-179}$) or SEQ ID NO: 11 (IL-22$^{34-179}$). An IL-22 herein can further include a methionine at its N-terminus, e.g., when such IL-22 protein is bacterially expressed. In one instance, an IL-22 has an amino acid sequence set forth in SEQ ID NO: 12 (MAL-22$^{34-179}$). An IL-22 herein can further include a methionine at its N-terminus, e.g., when such IL-22 protein is bacterially expressed. In one instance, an IL-22 has an amino acid sequence set forth in SEQ ID NO: 12 (M+IL-22$^{34179}$). The IL-22 can comprise, consist essentially of, or consist of SEQ ID NO: 10, or an amino acid sequence having at least 80%, 85%, 90%, 95%, 98% or 99%% sequence identity thereto or fragment thereof. The IL-22 can comprise, consists essentially of, or consist of SEQ ID NO: 11 (IL-22$^{34-179}$), which is a secreted form of IL-22, or an amino acid sequence having at least 80%, 85%, 90%, 95%, 98% or 99%% sequence identity thereto or fragment thereof. An IL-22 can include a methionine at its N-terminus, e.g., when such IL-22 protein is bacterially expressed. Such IL-22 can consist of, consist essentially of, or comprise an amino acid sequence set forth in SEQ ID NO: 12 (M+IL-22$^{34-179}$).

In some instances, a carrier used in any of the delivery constructs herein can be a protein or another type of molecule capable of transporting the therapeutic payload across an epithelium (e.g., a polarized gut epithelium of a subject). Such transport can include transcytosis. As referred to herein, "transcytosis" refers to the trafficking of the fusion molecule through a polarized epithelial cell. Such trafficking permits the release of the biologically active cargo from the basolateral membrane of the polarized epithelial cell. The transcytosis process may involve interaction(s) of the carrier with one or more receptor(s) and/or protein(s) on the apical and/or basal surface(s) as well as inside a cell of the epithelium (e.g., a polarized gut epithelial cell). The carrier can be capable of transporting the therapeutic payload across an epithelium without impairing the epithelium, the carrier, and/or the biological and/or therapeutic function of the payload.

A carrier can be coupled to a therapeutic payload covalently or non-covalently and directly or indirectly. The therapeutic payload can be directly coupled to the N-terminus or C-terminus of the carrier. In instances where the carrier is covalently coupled to the payload, the carrier can be coupled to such payload via a spacer (also referred to herein as a linker). The spacer can comprise at least 1, 2, 3, 4, 5, 6, 7, 8, 9, 10, 15, 20, or more amino acid residues. Spacer amino acid residues can be e.g., glycine, serine, and/or tryptophan. A spacer may be a cleavable or a non-cleavable spacer. A cleavable spacer may be cleavable by an enzyme or in a pH-dependent manner.

Examples of spacers contemplated herein include oligopeptide sequences such as S, (GS)x, (GGS)x, (GGGS)x (SEQ ID NO: 27), (GGGGS)x (SEQ ID NO: 28), or (GGGGGS)x (SEQ ID NO: 29), wherein x=1, 2, 3, 4, 5, 6, 7, 8, 9, 10, 11, 12, 13, 14, or 15. In some cases, a spacer consists of, consists essentially of, or comprises a sequence set forth in SEQ ID NO: 13 ((G$_4$S)$_3$). (GGGGSGGGGSGGGGS). In some cases, a spacer consists of, consists essentially of, or comprises a sequence set forth in SEQ ID NO: 31 ((G$_4$S)$_5$). (GGGGSGGGGSGGGGSGGGGSGGGGS). In some instances, a delivery construct comprises a therapeutic payload and a carrier that are non-covalently linked (e.g., via ionic interactions, van der Waals interactions, π-π interactions, etc.). A carrier can further comprise one or more features, elements, amino acids, or modifications on its N-terminus and/or C-terminus. For instance, some embodiments include a N-terminal methionine at the N-terminus of the carrier. Other modifications (e.g., acetylation) may also be present, including modifications for expression in a heterologous system.

A delivery construct herein can have an amino acid sequence set forth in SEQ ID NO: 15 or 17 (examples of M+Cholix$^{1-266}$-(G$_4$S)$_3$-IL-22$^{34-179}$) (TABLE 1). Other delivery constructs can have the amino acid sequence set forth in SEQ ID NOs: 24 or 25 (e.g., when expressed in a mammalian cell such as CHO cell). Such exemplary delivery constructs transport IL-22 across intact, polarized gut epithelial cells and into the lamina propria.

Figure 16:
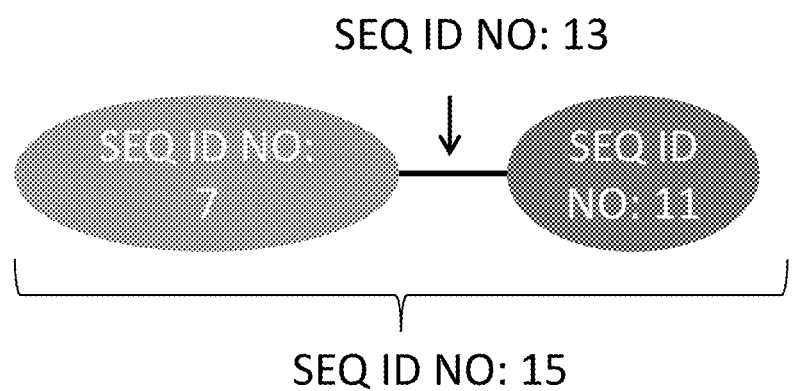
FIG. 16 illustrates that SEQ ID NO: 15 is a heterologous fusion protein comprising a carrier domain (SEQ ID NO: 7) linked via a spacer (SEQ ID NO: 13) to interleukin-22 (IL-22, SEQ ID NO: 11). The heterologous fusion proteins may be sequestered in E. coli inclusion bodies (IB) and thus require refolding and/or purification.

In various embodiments, the non-naturally occurring fusion protein has an amino acid sequence set forth in SEQ ID NO: 14-21, 24, or 25, or an amino acid sequence having at least 80%, 85%, 90%, 95%, 98% or 99% sequence identity thereto. A schematic of the carrier, spacer, and payload of a non-naturally occurring fusion protein comprising an amino acid sequence set forth in SEQ ID NO: 15 is illustrated in FIG. 16.

TABLE 1 shows exemplary amino acid sequences of biologically active molecules used in combination with the herein disclosed methods.

TABLE 1

Exemplary Amino Acid Sequences

| Category | SEQ ID NO | Amino Acid Sequence |
|---|---|---|
| Cholix$^{1-634}$ | SEQ ID NO: 1 | VEEALNIFDECRSPCSLTPEPGKPIQSKLSIPSDVVLD EGVLYYSMTINDEQNDIKDEDKGESIITIGEFATVRA TRHYVNQDAPFGVIHLDITTENGTKTYSYNRKEGEF AINWLVPIGEDSPASIKISVDELDQQRNIIEVPKLYSI DLDNQTLEQWKTQGNVSFSVTRPEHNIAISWPSVS YKAAQKEGSRHKRWAHWHTGLALCWLVPMDAIY NYITQQNCTLGDNWFGGSYETVAGTPKVITVKQGI EQKPVEQRIHFSKGNAMSALAAHRVCGVPLETLAR SRKPRDLTDDLSCAYQAQNIVSLFVATRILFSHLDS VFTLNLDEQEPEVAERLSDLRRINENNPGMVTQVL TVARQIYNDYVTHHPGLTPEQTSAGAQAADILSLFC PDADKSCVASNNDQANINIESRSGRSYLPENRAVIT PQGVTNWTYQELEATHQALTREGYVFVGYHGTNH VAAQTIVNRIAPVPRGNNTENEEKWGGLYVATHAE VAHGYARIKEGTGEYGLPTRAERDARGVMLRVYIP RASLERFYRTNTPLENAEEHITQVIGHSLPLRNEAFT GPESAGGEDETVIGWDMAIHAVAIPSTIPGNAYEEL AIDEEAVAKEQSISTKPPYKERKDELK |
| Cholix$^{1-386}$ | SEQ ID NO: 2 | VEEALNIFDECRSPCSLTPEPGKPIQSKLSIPSDVVLD EGVLYYSMTINDEQNDIKDEDKGESIITIGEFATVRA TRHYVNQDAPFGVIHLDITTENGTKTYSYNRKEGEF AINWLVPIGEDSPASIKISVDELDQQRNIIEVPKLYSI DLDNQTLEQWKTQGNVSFSVTRPEHNIAISWPSVS YKAAQKEGSRHKRWAHWHTGLALCWLVPMDAIY NYITQQNCTLGDNWFGGSYETVAGTPKVITVKQGI EQKPVEQRIHFSKGNAMSALAAHRVCGVPLETLAR SRKPRDLTDDLSCAYQAQNIVSLFVATRILFSHLDS VFTLNLDEQEPEVAERLSDLRRINENNPGMVTQVL TVARQIYNDYVTHHPGLTPEQTSAGAQA |
| Cholix$^{1-266}$ | SEQ ID NO: 3 | VEEALNIFDECRSPCSLTPEPGKPIQSKLSIPSDVVLD EGVLYYSMTINDEQNDIKDEDKGESIITIGEFATVRA TRHYVNQDAPFGVIHLDITTENGTKTYSYNRKEGEF AINWLVPIGEDSPASIKISVDELDQQRNIIEVPKLYSI DLDNQTLEQWKTQGNVSFSVTRPEHNIAISWPSVS YKAAQKEGSRHKRWAHWHTGLALCWLVPMDAIY NYITQQNCTLGDNWFGGSYETVAGTPKVITVKQGI EQKPVEQRIHFSKG |
| (V1L)-Cholix$^{1-386}$ | SEQ ID NO: 4 | LEEALNIFDECRSPCSLTPEPGKPIQSKLSIPSDVVLD EGVLYYSMTINDEQNDIKDEDKGESIITIGEFATVRA TRHYVNQDAPFGVIHLDITTENGTKTYSYNRKEGEF AINWLVPIGEDSPASIKISVDELDQQRNIIEVPKLYSI DLDNQTLEQWKTQGNVSFSVTRPEHNIAISWPSVS YKAAQKEGSRHKRWAHWHTGLALCWLVPMDAIY NYITQQNCTLGDNWFGGSYETVAGTPKVITVKQGI EQKPVEQRIHFSKGNAMSALAAHRVCGVPLETLAR SRKPRDLTDDLSCAYQAQNIVSLFVATRILFSHLDS VFTLNLDEQEPEVAERLSDLRRINENNPGMVTQVL TVARQIYNDYVTHHPGLTPEQTSAGAQA |
| (V1L)-Cholix$^{1-266}$ | SEQ ID NO: 5 | LEEALNIFDECRSPCSLTPEPGKPIQSKLSIPSDVVLD EGVLYYSMTINDEQNDIKDEDKGESIITIGEFATVRA TRHYVNQDAPFGVIHLDITTENGTKTYSYNRKEGEF AINWLVPIGEDSPASIKISVDELDQQRNIIEVPKLYSI DLDNQTLEQWKTQGNVSFSVTRPEHNIAISWPSVS |

TABLE 1-continued

Exemplary Amino Acid Sequences

| Category | SEQ ID NO | Amino Acid Sequence |
|---|---|---|
| | | YKAAQKEGSRHKRWAHWHTGLALCWLVPMDAIY<br>NYITQQNCTLGDNWFGGSYETVAGTPKVITVKQGI<br>EQKPVEQRIHFSKG |
| M + Cholix[1-386] | SEQ ID NO: 6 | MVEEALNIFDECRSPCSLTPEPGKPIQSKLSIPSDVVL<br>DEGVLYYSMTINDEQNDIKDEDKGESIITIGEFATVR<br>ATRHYVNQDAPFGVIHLDITTENGTKTYSYNRKEG<br>EFAINWLVPIGEDSPASIKISVDELDQQRNIIEVPKLY<br>SIDLDNQTLEQWKTQGNVSFSVTRPEHNIAISWPSV<br>SYKAAQKEGSRHKRWAHWHTGLALCWLVPMDAI<br>YNYITQQNCTLGDNWFGGSYETVAGTPKVITVKQG<br>IEQKPVEQRIHFSKGNAMSALAAHRVCGVPLETLA<br>RSRKPRDLTDDLSCAYQAQNIVSLFVATRILFSHLD<br>SVFTLNLDEQEPEVAERLSDLRRINENNPGMVTQVL<br>TVARQIYNDYVTHHPGLTPEQTSAGAQA |
| M + Cholix[1-266] | SEQ ID NO: 7 | MVEEALNIFDECRSPCSLTPEPGKPIQSKLSIPSDVVL<br>DEGVLYYSMTINDEQNDIKDEDKGESIITIGEFATVR<br>ATRHYVNQDAPFGVIHLDITTENGTKTYSYNRKEG<br>EFAINWLVPIGEDSPASIKISVDELDQQRNIIEVPKLY<br>SIDLDNQTLEQWKTQGNVSFSVTRPEHNIAISWPSV<br>SYKAAQKEGSRHKRWAHWHTGLALCWLVPMDAI<br>YNYITQQNCTLGDNWFGGSYETVAGTPKVITVKQG<br>IEQKPVEQRIHFSKG |
| M + (V1L)-Cholix[1-386] | SEQ ID NO: 8 | MLEEALNIFDECRSPCSLTPEPGKPIQSKLSIPSDVVL<br>DEGVLYYSMTINDEQNDIKDEDKGESIITIGEFATVR<br>ATRHYVNQDAPFGVIHLDITTENGTKTYSYNRKEG<br>EFAINWLVPIGEDSPASIKISVDELDQQRNIIEVPKLY<br>SIDLDNQTLEQWKTQGNVSFSVTRPEHNIAISWPSV<br>SYKAAQKEGSRHKRWAHWHTGLALCWLVPMDAI<br>YNYITQQNCTLGDNWFGGSYETVAGTPKVITVKQG<br>IEQKPVEQRIHFSKGNAMSALAAHRVCGVPLETLA<br>RSRKPRDLTDDLSCAYQAQNIVSLFVATRILFSHLD<br>SVFTLNLDEQEPEVAERLSDLRRINENNPGMVTQVL<br>TVARQIYNDYVTHHPGLTPEQTSAGAQA |
| M + (V1L)-Cholix[1-266] | SEQ ID NO: 9 | MLEEALNIFDECRSPCSLTPEPGKPIQSKLSIPSDVVL<br>DEGVLYYSMTINDEQNDIKDEDKGESIITIGEFATVR<br>ATRHYVNQDAPFGVIHLDITTENGTKTYSYNRKEG<br>EFAINWLVPIGEDSPASIKISVDELDQQRNIIEVPKLY<br>SIDLDNQTLEQWKTQGNVSFSVTRPEHNIAISWPSV<br>SYKAAQKEGSRHKRWAHWHTGLALCWLVPMDAI<br>YNYITQQNCTLGDNWFGGSYETVAGTPKVITVKQG<br>IEQKPVEQRIHFSKG |
| IL-22[1-179] | SEQ ID NO: 10 | MAALQKSVSSFLMGTLATSCLLLLALLVQGGAAAP<br>ISSHCRLDKSNFQQPYITNRTFMLAKEASLADNNTD<br>VRLIGEKLFHGVSMSERCYLMKQVLNFTLEEVLFP<br>QSDRFQPYMQEVVPFLARLSNRLSTCHIEGDDLHIQ<br>RNVQKLKDTVKKLGESGEIKAIGELDLLFMSLRNA<br>CI |
| IL-22[34-179] | SEQ ID NO: 11 | APISSHCRLDKSNFQQPYITNRTFMLAKEASLADNN<br>TDVRLIGEKLFHGVSMSERCYLMKQVLNFTLEEVL<br>FPQSDRFQPYMQEVVPFLARLSNRLSTCHIEGDDLH<br>IQRNVQKLKDTVKKLGESGEIKAIGELDLLFMSLRN<br>ACI |
| M + IL-22[34-179] | SEQ ID NO: 12 | MAPISSHCRLDKSNFQQPYITNRTFMLAKEASLADN<br>NTDVRLIGEKLFHGVSMSERCYLMKQVLNFTLEEV<br>LFPQSDRFQPYMQEVVPFLARLSNRLSTCHIEGDDL<br>HIQRNVQKLKDTVKKLGESGEIKAIGELDLLFMSLR<br>NACI |
| (G4S)3 | SEQ ID NO: 13 | GGGGSGGGGSGGGGS |
| M + Cholix[1-386]-(G4S)3-IL-22[34-179] | SEQ ID NO: 14 | MLEEALNIFDECRSPCSLTPEPGKPIQSKLSIPSDVVL<br>DEGVLYYSMTINDEQNDIKDEDKGESIITIGEFATVR<br>ATRHYVNQDAPFGVIHLDITTENGTKTYSYNRKEG<br>EFAINWLVPIGEDSPASIKISVDELDQQRNIIEVPKLY<br>SIDLDNQTLEQWKTQGNVSFSVTRPEHNIAISWPSV<br>SYKAAQKEGSRHKRWAHWHTGLALCWLVPMDAI<br>YNYITQQNCTLGDNWFGGSYETVAGTPKVITVKQG<br>IEQKPVEQRIHFSKGNAMSALAAHRVCGVPLETLA |

TABLE 1-continued

| Exemplary Amino Acid Sequences | | |
|---|---|---|
| Category | SEQ ID NO | Amino Acid Sequence |
| | | RSRKPRDLTDDLSCAYQAQNIVSLFVATRILFSHLD SVFTLNLDEQEPEVAERLSDLRRINENNPGMVTQVL TVARQIYNDYVTHHPGLTPEQTSAGAQAGGGGSG GGGSGGGGSAPISSHCRLDKSNFQQPYITNRTFMLA KEASLADNNTDVRLIGEKLFHGVSMSERCYLMKQ VLNFTLEEVLFPQSDRFQPYMQEVVPFLARLSNRLS TCHIEGDDLHIQRNVQKLKDTVKKLGESGEIKAIGE LDLLFMSLRNACI |
| M + Cholix$^{1-266}$-$(G_4S)_3$-IL-22$^{34-179}$ | SEQ ID NO: 15 | MVEEALNIFDECRSPCSLTPEPGKPIQSKLSIPSDVVL DEGVLYYSMTINDEQNDIKDEDKGESIITIGEFATVR ATRHYVNQDAPFGVIHLDITTENGTKTYSYNRKEG EFAINWLVPIGEDSPASIKISVDELDQQRNIIEVPKLY SIDLDNQTLEQWKTQGNVSFSVTRPEHNIAISWPSV SYKAAQKEGSRHKRWAHWHTGLALCWLVPMDAI YNYITQQNCTLGDNWFGGSYETVAGTPKVITVKQG IEQKPVEQRIHFSKGGGGGSGGGGSGGGGSAPISSH CRLDKSNFQQPYITNRTFMLAKEASLADNNTDVRLI GEKLFHGVSMSERCYLMKQVLNFTLEEVLFPQSDR FQPYMQEVVPFLARLSNRLSTCHIEGDDLHIQRNVQ KLKDTVKKLGESGEIKAIGELDLLFMSLRNACI |
| M + (V1L)-Cholix$^{1-386}$-$(G_4S)_3$-IL-22$^{34-179}$ | SEQ ID NO: 16 | MVEEALNIFDECRSPCSLTPEPGKPIQSKLSIPSDVVL DEGVLYYSMTINDEQNDIKDEDKGESIITIGEFATVR ATRHYVNQDAPFGVIHLDITTENGTKTYSYNRKEG EFAINWLVPIGEDSPASIKISVDELDQQRNIIEVPKLY SIDLDNQTLEQWKTQGNVSFSVTRPEHNIAISWPSV SYKAAQKEGSRHKRWAHWHTGLALCWLVPMDAI YNYITQQNCTLGDNWFGGSYETVAGTPKVITVKQG IEQKPVEQRIHFSKGNAMSALAAHRVCGVPLETLA RSRKPRDLTDDLSCAYQAQNIVSLFVATRILFSHLD SVFTLNLDEQEPEVAERLSDLRRINENNPGMVTQVL TVARQIYNDYVTHHPGLTPEQTSAGAQAGGGGSG GGGSGGGGSAPISSHCRLDKSNFQQPYITNRTFMLA KEASLADNNTDVRLIGEKLFHGVSMSERCYLMKQ VLNFTLEEVLFPQSDRFQPYMQEVVPFLARLSNRLS TCHIEGDDLHIQRNVQKLKDTVKKLGESGEIKAIGE LDLLFMSLRNACI |
| M + (V1L)-Cholix$^{1-266}$-$(G_4S)_3$-IL-22$^{34-179}$ | SEQ ID NO: 17 | MLEEALNIFDECRSPCSLTPEPGKPIQSKLSIPSDVVL DEGVLYYSMTINDEQNDIKDEDKGESIITIGEFATVR ATRHYVNQDAPFGVIHLDITTENGTKTYSYNRKEG EFAINWLVPIGEDSPASIKISVDELDQQRNIIEVPKLY SIDLDNQTLEQWKTQGNVSFSVTRPEHNIAISWPSV SYKAAQKEGSRHKRWAHWHTGLALCWLVPMDAI YNYITQQNCTLGDNWFGGSYETVAGTPKVITVKQG IEQKPVEQRIHFSKGGGGGSGGGGSGGGGSAPISSH CRLDKSNFQQPYITNRTFMLAKEASLADNNTDVRLI GEKLFHGVSMSERCYLMKQVLNFTLEEVLFPQSDR FQPYMQEVVPFLARLSNRLSTCHIEGDDLHIQRNVQ KLKDTVKKLGESGEIKAIGELDLLFMSLRNACI |
| Cholix$^{1-386}$-$(G_4S)_3$-IL-22$^{34-179}$ | SEQ ID NO: 18 | VEEALNIFDECRSPCSLTPEPGKPIQSKLSIPSDVVLD EGVLYYSMTINDEQNDIKDEDKGESIITIGEFATVRA TRHYVNQDAPFGVIHLDITTENGTKTYSYNRKEGEF AINWLVPIGEDSPASIKISVDELDQQRNIIEVPKLYSI DLDNQTLEQWKTQGNVSFSVTRPEHNIAISWPSVS YKAAQKEGSRHKRWAHWHTGLALCWLVPMDAIY NYITQQNCTLGDNWFGGSYETVAGTPKVITVKQGI EQKPVEQRIHFSKGNAMSALAAHRVCGVPLETLAR SRKPRDLTDDLSCAYQAQNIVSLFVATRILFSHLDS VFTLNLDEQEPEVAERLSDLRRINENNPGMVTQVL TVARQIYNDYVTHHPGLTPEQTSAGAQAGGGGSG GGGSGGGGSAPISSHCRLDKSNFQQPYITNRTFMLA KEASLADNNTDVRLIGEKLFHGVSMSERCYLMKQ VLNFTLEEVLFPQSDRFQPYMQEVVPFLARLSNRLS TCHIEGDDLHIQRNVQKLKDTVKKLGESGEIKAIGE LDLLFMSLRNACI |
| (V1L)-Cholix$^{1-386}$-$(G_4S)_3$-IL-22$^{34-179}$ | SEQ ID NO: 19 | LEEALNIFDECRSPCSLTPEPGKPIQSKLSIPSDVVLD EGVLYYSMTINDEQNDIKDEDKGESIITIGEFATVRA TRHYVNQDAPFGVIHLDITTENGTKTYSYNRKEGEF AINWLVPIGEDSPASIKISVDELDQQRNIIEVPKLYSI DLDNQTLEQWKTQGNVSFSVTRPEHNIAISWPSVS YKAAQKEGSRHKRWAHWHTGLALCWLVPMDAIY NYITQQNCTLGDNWFGGSYETVAGTPKVITVKQGI |

TABLE 1-continued

Exemplary Amino Acid Sequences

| Category | SEQ ID NO | Amino Acid Sequence |
|---|---|---|
| | | EQKPVEQRIHFSKGNAMSALAAHRVCGVPLETLAR<br>SRKPRDLTDDLSCAYQAQNIVSLFVATRILFSHLDS<br>VFTLNLDEQEPEVAERLSDLRRINENNPGMVTQVL<br>TVARQIYNDYVTHHPGLTPEQTSAGAQAGGGGSG<br>GGGSGGGGSAPISSHCRLDKSNFQQPYITNRTFMLA<br>KEASLADNNTDVRLIGEKLFHGVSMSERCYLMKQ<br>VLNFTLEEVLFPQSDRFQPYMQEVVPFLARLSNRLS<br>TCHIEGDDLHIQRNVQKLKDTVKKLGESGEIKAIGE<br>LDLLFMSLRNACI |
| Cholix$^{1-266}$-<br>(G$_4$S)$_3$-<br>IL-22$^{34-179}$ | SEQ ID NO:<br>20 | VEEALNIFDECRSPCSLTPEPGKPIQSKLSIPSDVVLD<br>EGVLYYSMTINDEQNDIKDEDKGESIITIGEFATVRA<br>TRHYVNQDAPFGVIHLDITTENGTKTYSYNRKEGEF<br>AINWLVPIGEDSPASIKISVDELDQQRNIIEVPKLYSI<br>DLDNQTLEQWKTQGNVSFSVTRPEHNIAISWPSVS<br>YKAAQKEGSRHKRWAHWHTGLALCWLVPMDAIY<br>NYITQQNCTLGDNWFGGSYETVAGTPKVITVKQGI<br>EQKPVEQRIHFSKGGGGSGGGGSGGGGSAPISSHC<br>RLDKSNFQQPYITNRTFMLAKEASLADNNTDVRLI<br>GEKLFHGVSMSERCYLMKQVLNFTLEEVLFPQSDR<br>FQPYMQEVVPFLARLSNRLSTCHIEGDDLHIQRNVQ<br>KLKDTVKKLGESGEIKAIGELDLLFMSLRNACI |
| (V1L)-<br>Cholix$^{1-266}$-<br>(G$_4$S)$_3$-IL-<br>22$^{34-179}$ | SEQ ID NO:<br>21 | LEEALNIFDECRSPCSLTPEPGKPIQSKLSIPSDVVLD<br>EGVLYYSMTINDEQNDIKDEDKGESIITIGEFATVRA<br>TRHYVNQDAPFGVIHLDITTENGTKTYSYNRKEGEF<br>AINWLVPIGEDSPASIKISVDELDQQRNIIEVPKLYSI<br>DLDNQTLEQWKTQGNVSFSVTRPEHNIAISWPSVS<br>YKAAQKEGSRHKRWAHWHTGLALCWLVPMDAIY<br>NYITQQNCTLGDNWFGGSYETVAGTPKVITVKQGI<br>EQKPVEQRIHFSKGGGGSGGGGSGGGGSAPISSHC<br>RLDKSNFQQPYITNRTFMLAKEASLADNNTDVRLI<br>GEKLFHGVSMSERCYLMKQVLNFTLEEVLFPQSDR<br>FQPYMQEVVPFLARLSNRLSTCHIEGDDLHIQRNVQ<br>KLKDTVKKLGESGEIKAIGELDLLFMSLRNACI |
| (V1L)-<br>Cholix$^{1-634}$ | SEQ ID NO:<br>22 | LEEALNIFDECRSPCSLTPEPGKPIQSKLSIPSDVVLD<br>EGVLYYSMTINDEQNDIKDEDKGESIITIGEFATVRA<br>TRHYVNQDAPFGVIHLDITTENGTKTYSYNRKEGEF<br>AINWLVPIGEDSPASIKISVDELDQQRNIIEVPKLYSI<br>DLDNQTLEQWKTQGNVSFSVTRPEHNIAISWPSVS<br>YKAAQKEGSRHKRWAHWHTGLALCWLVPMDAIY<br>NYITQQNCTLGDNWFGGSYETVAGTPKVITVKQGI<br>EQKPVEQRIHFSKGNAMSALAAHRVCGVPLETLAR<br>SRKPRDLTDDLSCAYQAQNIVSLFVATRILFSHLDS<br>VFTLNLDEQEPEVAERLSDLRRINENNPGMVTQVL<br>TVARQIYNDYVTHHPGLTPEQTSAGAQAADILSLFC<br>PDADKSCVASNNDQANINIESRSGRSYLPENRAVIT<br>PQGVTNWTYQELEATHQALTREGYVFVGYHGTNH<br>VAAQTIVNRIAPVPRGNNTENEEKWGGLYVATHAE<br>VAHGYARIKEGTEYGLPTRAERDARGVMLRVYIP<br>RASLERFYRTNTPLENAEEHITQVIGHSLPLRNEAFT<br>GPESAGGEDETVIGWDMAIHAVAIPSTIPGNAYEEL<br>AIDEEAVAKEQSISTKPPYKERKDELK |
| M + (V1L)-<br>Cholix$^{1-634}$ | SEQ ID NO:<br>23 | MLEEALNIFDECRSPCSLTPEPGKPIQSKLSIPSDVVL<br>DEGVLYYSMTINDEQNDIKDEDKGESIITIGEFATVR<br>ATRHYVNQDAPFGVIHLDITTENGTKTYSYNRKEG<br>EFAINWLVPIGEDSPASIKISVDELDQQRNIIEVPKLY<br>SIDLDNQTLEQWKTQGNVSFSVTRPEHNIAISWPSV<br>SYKAAQKEGSRHKRWAHWHTGLALCWLVPMDAI<br>YNYITQQNCTLGDNWFGGSYETVAGTPKVITVKQG<br>IEQKPVEQRIHFSKGNAMSALAAHRVCGVPLETLA<br>RSRKPRDLTDDLSCAYQAQNIVSLFVATRILFSHLD<br>SVFTLNLDEQEPEVAERLSDLRRINENNPGMVTQVL<br>TVARQIYNDYVTHHPGLTPEQTSAGAQAADILSLFC<br>PDADKSCVASNNDQANINIESRSGRSYLPENRAVIT<br>PQGVTNWTYQELEATHQALTREGYVFVGYHGTNH<br>VAAQTIVNRIAPVPRGNNTENEEKWGGLYVATHAE<br>VAHGYARIKEGTEYGLPTRAERDARGVMLRVYIP<br>RASLERFYRTNTPLENAEEHITQVIGHSLPLRNEAFT<br>GPESAGGEDETVIGWDMAIHAVAIPSTIPGNAYEEL<br>AIDEEAVAKEQSISTKPPYKERKDELK |

TABLE 1-continued

| Exemplary Amino Acid Sequences | | |
|---|---|---|
| Category | SEQ ID NO | Amino Acid Sequence |
| Cholix$^{1-266}$-(G$_4$S)$_3$-IL-22$^{34-179}$ | SSEQ ID NO: 24 | VEEALNIFDECRSPCSLTPEPGKPIQSKLSIPSDVVLD EGVLYYSMTINDEQNDIKDEDKGESITTIGEFATVRA TRHYVNQDAPFGVIHLDITTENGTKTYSYNRKEGEF AINWLVPIGEDSPASIKISVDELDQQRNIIEVPKLYSI DLDNQTLEQWKTQGNVSFSVTRPEHNIAISWPSVS YKAAQKEGSRHKRWAHWHTGLALCWLVPMDAIY NYITQQNCTLGDNWFGGSYETVAGTPKVITVKQGI EQKPVEQRIHFSKGGGGGSGGGGSGGGGSAPISSHC RLDKSNFQQPYITNRTFMLAKEASLADNNTDVRLI GEKLFHGVSMSERCYLMKQVLNFTLEEVLFPQSDR FQPYMQEVVPFLARLSNRLSTCHIEGDDLHIQRNVQ KLKDTVKKLGESGEIKAIGELDLLFMSLRNACI |
| (V1L)-Cholix$^{1-266}$-(G$_4$S)$_3$-IL-22$^{34-179}$ | SSEQ ID NO: 25 | LEEALNIFDECRSPCSLTPEPGKPIQSKLSIPSDVVLD EGVLYYSMTINDEQNDIKDEDKGESITTIGEFATVRA TRHYVNQDAPFGVIHLDITTENGTKTYSYNRKEGEF AINWLVPIGEDSPASIKISVDELDQQRNIIEVPKLYSI DLDNQTLEQWKTQGNVSFSVTRPEHNIAISWPSVS YKAAQKEGSRHKRWAHWHTGLALCWLVPMDAIY NYITQQNCTLGDNWFGGSYETVAGTPKVITVKQGI EQKPVEQRIHFSKGGGGGSGGGGSGGGGSAPISSHC RLDKSNFQQPYITNRTFMLAKEASLADNNTDVRLI GEKLFHGVSMSERCYLMKQVLNFTLEEVLFPQSDR FQPYMQEVVPFLARLSNRLSTCHIEGDDLHIQRNVQ KLKDTVKKLGESGEIKAIGELDLLFMSLRNACI |
| M + Cholix$^{1-266}$-(G$_4$S)$_1$-IL-22$^{34-179}$ | SEQ ID NO: 32 | MVEEALNIFDECRSPCSLTPEPGKPIQSKLSIPSDVVL DEGVLYYSMTINDEQNDIKDEDKGESIITIGEFATVR ATRHYVNQDAPFGVIHLDITTENGTKTYSYNRKEG EFAINWLVPIGEDSPASIKISVDELDQQRNIIEVPKLY SIDLDNQTLEQWKTQGNVSFSVTRPEHNIAISWPSV SYKAAQKEGSRHKRWAHWHTGLALCWLVPMDAI YNYITQQNCTLGDNWFGGSYETVAGTPKVITVKQG IEQKPVEQRIHFSKGGGGGSAPISSHCRLDKSNFQQP YITNRTFMLAKEASLADNNTDVRLIGEKLFHGVSM SERCYLMKQVLNFTLEEVLFPQSDRFQPYMQEVVP FLARLSNRLSTCHIEGDDLHIQRNVQKLKDTVKKL GESGEIKAIGELDLLFMSLRNACI |
| M + Cholix$^{1-266}$-(G$_4$S)$_5$-IL-22$^{34-179}$ | SEQ ID NO: 33 | MVEEALNIFDECRSPCSLTPEPGKPIQSKLSIPSDVVL DEGVLYYSMTINDEQNDIKDEDKGESIITIGEFATVR ATRHYVNQDAPFGVIHLDITTENGTKTYSYNRKEG EFAINWLVPIGEDSPASIKISVDELDQQRNIIEVPKLY SIDLDNQTLEQWKTQGNVSFSVTRPEHNIAISWPSV SYKAAQKEGSRHKRWAHWHTGLALCWLVPMDAI YNYITQQNCTLGDNWFGGSYETVAGTPKVITVKQG IEQKPVEQRIHFSKGGGGGSGGGGSGGGGSGGGGS GGGGSAPISSHCRLDKSNFQQPYITNRTFMLAKEAS LADNNTDVRLIGEKLFHGVSMSERCYLMKQVLNFT LEEVLFPQSDRFQPYMQEVVPFLARLSNRLSTCHIE GDDLHIQRNVQKLKDTVKKLGESGEIKAIGELDLLF MSLRNACI |
| M + IL-22$^{34-179}$-(G$_4$S)$_1$-Cholix$^{1-266}$ | SEQ ID NO: 34 | MAPISSHCRLDKSNFQQPYITNRTFMLAKEASLADN NTDVRLIGEKLFHGVSMSERCYLMKQVLNFTLEEV LFPQSDRFQPYMQEVVPFLARLSNRLSTCHIEGDDL HIQRNVQKLKDTVKKLGESGEIKAIGELDLLFMSLR NACIGGGGSVEEALNIFDECRSPCSLTPEPGKPIQSK LSIPSDVVLDEGVLYYSMTINDEQNDIKDEDKGESII TIGEFATVRATRHYVNQDAPFGVIHLDITTENGTKT YSYNRKEGEFAINWLVPIGEDSPASIKISVDELDQQR NIIEVPKLYSIDLDNQTLEQWKTQGNVSFSVTRPEH NIAISWPSVSYKAAQKEGSRHKRWAHWHTGLALC WLVPMDAIYNYITQQNCTLGDNWFGGSYETVAGT PKVITVKQGIEQKPVEQRIHFSKG |
| M + Cholix$^{1-386}$-(G$_4$S)$_1$-IL-22$^{34-179}$ | SEQ ID NO: 35 | MVEEALNIFDECRSPCSLTPEPGKPIQSKLSIPSDVVL DEGVLYYSMTINDEQNDIKDEDKGESIITIGEFATVR ATRHYVNQDAPFGVIHLDITTENGTKTYSYNRKEG EFAINWLVPIGEDSPASIKISVDELDQQRNIIEVPKLY SIDLDNQTLEQWKTQGNVSFSVTRPEHNIAISWPSV SYKAAQKEGSRHKRWAHWHTGLALCWLVPMDAI YNYITQQNCTLGDNWFGGSYETVAGTPKVITVKQG IEQKPVEQRIHFSKGNAMSALAAHRVCGVPLETLA RSRKPRDLTDDLSCAYQAQNIVSLFVATRILFSHLD SVFTLNLDEQEPEVAERLSDLRRINENNPGMVTQVL |

TABLE 1-continued

Exemplary Amino Acid Sequences

| Category | SEQ ID NO | Amino Acid Sequence |
|---|---|---|
| | | TVARQIYNDYVTHHPGLTPEQTSAGAQAGGGGSAP ISSHCRLDKSNFQQPYITNRTFMLAKEASLADNNTD VRLIGEKLFHGVSMSERCYLMKQVLNFTLEEVLFP QSDRFQPYMQEVVPFLARLSNRLSTCHIEGDDLHIQ RNVQKLKDTVKKLGESGEIKAIGELDLLFMSLRNA CI |
| Cholix Consensus Sequence | SEQ ID NO: 26 | X1-E-X3-X4-L-X6-I-F-D-E-C-R-S-P-C-X16-L-T-P-E-X21-G-K-X24-I-Q-S-K-L-X30-I-P-X33-D-V-V-L-D-E-G-V-L-Y-Y-S-M-T-I-N-D-E-Q-N-D-I-X56-D-E-X59-K-G-E-S-I-I-T-X67-G-E-F-A-T-X73-R-A-T-R-H-Y-V-X81-Q-D-A-P-F-G-V-I-X90-L-D-I-T-T-E-N-G-T-K-X101-Y-S-X104-N-R-K-X108-X109-E-F-X112-I-X114-W-L-V-X118-X119-G-E-D-S-P-A-S-I-K-I-S-X131-D-E-X134-D-Q-X137-R-N-I-I-E-V-P-K-L-Y-S-I-D-L-D-N-Q-T-L-E-Q-W-X160-X161-Q-G-N-V-X166-F-X168-V-T-R-P-E-X174-X175-I-A-I-S-W-P-S-V-S-Y-X186-A-A-X189-K-X191-G-X193-R-H-K-R-W-A-X200-W-X202-T-X204-X205-X206-X207-X208-X209-L-X211-X212-X213-X214-X215-X216-X217-X218-X219-X220-X221-X222-X223-X224-C-T-X227-G-X229-X230-W-X232-G-G-X235-Y-X237-T-V-A-G-X242-P-X244-X245-I-X247-V-K-Q-G-X252-E-Q-K-X256-V-E-Q-R-I-H-F-S-X265-X266-N-A-X269-X270-X271-L-A-A-H-R-V-C-G-V-P-L-E-T-L-A-R-X288-R-K-P-R-X293-L-X295-D-D-L-X299-C-X301-Y-X303-A-Q-X306-I-V-S-L-F-X312-A-T-R-X316-L-F-X319-H-X321-D-S-X324-F-T-L-N-L-X330-X331-Q-X333-P-X335-V-X337-E-R-L-X341-X342-X343-R-X345-I-N-E-X349-N-P-X353-V-X355-Q-V-L-T-X360-A-R-Q-I-Y-N-D-Y-V-T-X371-H-P-X374-L-X376-P-E-Q-T-S-A-X383-A-Q-A-A-D-1-L-S-L-X393-X394-P-D-X397-D-X399-X400-C-V-A-X404-X405-X406-D-Q-A-N-I-N-X413-E-S-R-S-G-R-S-Y-L-X423-E-N-R-A-V-I-T-X431-Q-G-V-T-N-W-T-Y-Q-E-L-X443-X444-X445-H-Q-X448-L-T-X451-E-X453-Y-V-F-V-G-Y-H-G-T-N-H-X465-A-A-Q-X469-I-V-N-R-I-X475-P-V-P-R-G-X481-X482-T-E-X485-E-X487-X488-W-G-G-X492-Y-V-X495-T-X497-A-X499-X500-X501-X502-X503-Y-X505-R-X507-X508-X509-G-T-X512-X513-X514-X515-X516-X517-T-X519-X520-X521-X522-X523-X524-R-G-V-M-L-X530-V-Y-X533-X534-X535-A-S-L-E-R-F-Y-R-X544-N-X546-X547-L-E-X550-X551-X552-X553-X554-X555-X556-X557-V-I-G-H-X562-L-P-L-R-N-E-A-F-T-G-X573-X574-X575-X576-X577-G-X579-X580-E-T-X583-I-G-W-D-X588-A-I-X591-X592-V-A-I-P-S-T-I-P-G-N-X603-Y-X605-X606-L-X608-X609-X610-E-E-A-X614-A-X616-E-Q-S-I-S-X622-K-P-P-Y-K-E-X629-X630-D-E-L-K; wherein X1 is selected from the group consisting of V and L; X3 is selected from the group consisting of E and D; X4 is selected from the group consisting of A and E; X6 is selected from the group consisting of N and K; X16 is selected from the group consisting of S and L; X21 is selected from the group consisting of P and L; X24 is selected from the group consisting of P and Q; X30 is selected from the group consisting of S and F; X33 is selected from the group consisting of S and G; X56 is selected from the group consisting of K and M; X59 is selected from the group consisting of D and G; X67 is selected from the group consisting of I and F; X73 is selected from the group consisting of V and I; X81 is selected from the group consisting of N and S; X90 is selected from the group consisting of H and N; X101 is selected from the group consisting of T and M; X104 is selected from the group consisting of Y and F; X108 is selected from the group consisting of E and D; X109 is selected from the group consisting of G and S; X112 is selected from the group consisting of A and T; X114 is selected from the group consisting of N and H; X118 is selected from the group consisting of P and I; X119 is selected from the group consisting of I and P; X131 is selected from the group consisting of V and I; X134 is selected from the group consisting L and I; X137 is selected from the group consisting Q and K; X160 is selected from the group consisting K and E; X161 is selected from the group consisting T and N; X166 is |

TABLE 1-continued

Exemplary Amino Acid Sequences

| Category | SEQ ID NO | Amino Acid Sequence |
|---|---|---|
| | | selected from the group consisting S and F; X168 is selected from the group consisting S and A; X174 is selected from the group consisting H and Q; X175 is selected from the group consisting N, S, SIAKQS, and SIAKQSIAKQS; X186 is selected from the group consisting of K and N; X189 is selected from the group consisting of Q, E, and H; X191 is selected from the group consisting of E, N, and D; X193 is selected from the group consisting of S and A; X200 is selected from the group consisting of H and N; X202 is selected from the group consisting of H, L, F, and R; X204 is selected from the group consisting of G and T; X205 is selected from the group consisting of L and S; X206 is selected from the group consisting of A and P; X207 is selected from the group consisting of L, E, and K; X208 is selected from the group consisting of C and V; X209 is selected from the group consisting of W, V, and T; X211 is selected from the group consisting of V and no amino acid; X212 is selected from the group consisting of P and no amino acid; X213 is selected from the group consisting of M, I, L, and no amino acid; X214 is selected from the group consisting of D and no amino acid; X215 is selected from the group consisting of A and no amino acid; X216 is selected from the group consisting of I and no amino acid; X217 is selected from the group consisting of Y and C; X218 is selected from the group consisting of N and F; X219 is selected from the group consisting of Y and F; X220 is selected from the group consisting of I and E; X221 is selected from the group consisting of T and D; X222 is selected from the group consisting of Q and P; X223 is selected from the group consisting of Q, E, and A; X224 is selected from the group consisting of N, L, and Q; X227 is selected from the group consisting of L and Y; X229 is selected from the group consisting of D and E; X230 is selected from the group consisting of N and D; X232 is selected from the group consisting of F, H, and Y; X235 is selected from the group consisting of S and A; X237 is selected from the group consisting of E and K; X242 is selected from the group consisting of T and I; X244 is selected from the group consisting of K, E, and G; X245 is selected from the group consisting of V and A; X247 is selected from the group consisting of T and M; X252 is selected from the group consisting of I and M; X256 is selected from the group consisting of P, T, and A; X265 is selected from the group consisting of K, Q, and N; X266 is selected from the group consisting of G and K; X269 is selected from the group consisting of M and I; X270 is selected from the group consisting of S and E; X271 is selected from the group consisting of A and T; X288 is selected from the group consisting of S and G; X293 is selected from the group consisting of D and Y; X295 is selected from the group consisting of T, P, and Q; X299 is selected from the group consisting of S and Q; X301 is selected from the group consisting of A and V; X303 is selected from the group consisting of Q and N; X306 is selected from the group consisting of N and Q; X312 is selected from the group consisting of V and L; X316 is selected from the group consisting of I and M; X319 is selected from the group consisting of S and T; X321 is selected from the group consisting of L and I; X324 is selected from the group consisting of V and I; X330 is selected from the group consisting of D, E, and H; X331 is selected from the group consisting of E and G; X333 is selected from the group consisting of E and A; X335 is selected from the group consisting of E and A; X337 is selected from the group consisting of A and T; X341 is selected from the group consisting of S, D, and T; X342 is selected from the group consisting of D and A; X343 is selected from the group consisting of L and I; X345 is selected from the group consisting of R and Q; X349 is selected from the group consisting of N and D; X353 is selected from the group consisting of M and V; X355 is selected from the group consisting of T and I; X360 is selected from the group consisting of V and I; X371 is selected from the group consisting of H and E; X374 is selected from the group consisting of G and L; |

TABLE 1-continued

Exemplary Amino Acid Sequences

| Category | SEQ ID NO | Amino Acid Sequence |
|---|---|---|
| | | X376 is selected from the group consisting of T and I; X383 is selected from the group consisting of G and S; X393 is selected from the group consisting of F and L; X394 is selected from the group consisting of C and Y; X397 is selected from the group consisting of A and T; X399 is selected from the group consisting of K, E, and G; X400 is selected from the group consisting of S, P, and H; X404 is selected from the group consisting of S and L; X405 is selected from the group consisting of N and D; X406 is selected from the group consisting of N and S; X413 is selected from the group consisting of I and V; X423 is selected from the group consisting of P and L; X431 is selected from the group consisting of P and Q; X443 is selected from the group consisting of E and D; X444 is selected from the group consisting of A and T; X445 is selected from the group consisting of T and K; X448 is selected from the group consisting of A and T; X451 is selected from the group consisting of R and Q; X453 is selected from the group consisting of G and D; X465 is selected from the group consisting of V and A; X469 is selected from the group consisting of T, S, and N; X475 is selected from the group consisting of A, S, and T; X481 is selected from the group consisting of N and S; X482 is selected from the group consisting of N and D; X485 is selected from the group consisting of N, S, and K; X487 is selected from the group consisting of E, R, and K; X488 is selected from the group consisting of K, A, and E; X492 is selected from the group consisting of L and V; X495 is selected from the group consisting of A and S; X497 is selected from the group consisting of H and D; X499 is selected from the group consisting of E and S; X500 is selected from the group consisting of V and L; X501 is selected from the group consisting of A and N; X502 is selected from the group consisting of H and Y; X503 is selected from the group consisting of G and R; X505 is selected from the group consisting of A and T; X507 is selected from the group consisting of I and L; X508 is selected from the group consisting of K and Q; X509 is selected from the group consisting of E and K; X512 is selected from the group consisting of G and A; X513 is selected from the group consisting of E, D, and N; X514 is selected from the group consisting of Y, G, A, and N; X515 is selected from the group consisting of G and E; X516 is selected from the group consisting of L and G; X517 is selected from the group consisting of P and L; X519 is selected from the group consisting of R, P, and T; X520 is selected from the group consisting of A and E; X521 is selected from the group consisting of E and K; X522 is selected from the group consisting of R, Q, and K; X523 is selected from the group consisting of D, K, and E; X524 is selected from the group consisting of A, T, and S; X530 is selected from the group consisting of R and K; X533 is selected from the group consisting of I and L; X534 is selected from the group consisting of P and H; X535 is selected from the group consisting of R and Q; X544 is selected from the group consisting of T and I; X546 is selected from the group consisting of T, A, and I; X547 is selected from the group consisting of P and D; X550 is selected from the group consisting of N and K; X551 is selected from the group consisting of A and E; X552 is selected from the group consisting of E, R, and D; X553 is selected from the group consisting of E, N, and R; X554 is selected from the group consisting of H and L; X555 is selected from the group consisting of I and V; X556 is selected from the group consisting of T and E; X557 is selected from the group consisting of Q, R, H, and D; X562 is selected from the group consisting of S and P; X573 is selected from the group consisting of P and T; X574 is selected from the group consisting of E and D; X575 is selected from the group consisting of S, A, and R; X576 is selected from the group consisting of A, E, and V; X577 is selected from the group consisting of G, E, and D; X579 is selected from the group consisting of E and S; X580 is selected from the group consisting of D and N; X583 is selected from the group consisting of V and A; X588 is selected from the group consisting of M |

TABLE 1-continued

Exemplary Amino Acid Sequences

| Category | SEQ ID NO | Amino Acid Sequence |
|---|---|---|
| | | and I; X591 is selected from the group consisting of H and Y; X592 is selected from the group consisting of A and G; X603 is selected from the group consisting of A and S; X605 is selected from the group consisting of E and A; X606 is selected from the group consisting of E, A, Q, G, V, and R; X608 is selected from the group consisting of A, P, and T; X609 is selected from the group consisting of I, T, and P; X610 is selected from the group consisting of D and A; X614 is selected from the group consisting of V and VVKEAI; X616 is selected from the group consisting of K and E; X622 is selected from the group consisting of T, A, and P; and X629 is selected from the group consisting of R, Q, and H; and X630 is selected from the group consisting of K and no amino acid. |

In some embodiments, the non-naturally occurring fusion protein comprises or consists of: a carrier selected from the group consisting of any one of the sequences set forth in SEQ ID NO: 1-9,22-23, and 26 and a payload selected from the group consisting of any one of the sequences set forth in SEQ ID NO: 10-12, and wherein the carrier and the payload are optionally coupled by a spacer selected from the group consisting of any one of the sequences set forth in SEQ ID NO: 13 and 27-29.

Further provided herein are pharmaceutical compositions comprising a delivery construct and one or more pharmaceutically acceptable carriers. In some cases, the delivery construct consists of the amino acid sequence set forth in SEQ ID NO: 15. In some cases, the delivery construct consists of the amino acid sequence set forth in SEQ ID NO: 17. Such pharmaceutical compositions can be formulated for administration to a subject. In some instances, a pharmaceutical composition is formulated for oral administration to a subject.

A pharmaceutical composition comprising a delivery construct can be administered to a subject (e.g., a human) in need thereof to treat a disease. Diseases that can be treated using the delivery constructs of this disclosure include autoimmune diseases and inflammatory diseases. In some instances, the disease is an epithelial cell injury or damage of epithelial cell membranes (e.g., in the GI tract). In some instances, the disease is hepatitis, obesity, fatty liver disease, liver inflammation, or pancreatitis, Crohn's disease (e.g., fistulizing Crohn's disease), ulcerative colitis (e.g., mild-to-moderate or moderate-to-severe), pouchitis, proctitis, multiple sclerosis, systemic lupus erythematosus, graft versus host disease, rheumatoid arthritis, or psoriasis.

Purification Methods and Compositions

The present disclosure contemplates methods for obtaining a purified non-naturally occurring fusion protein. The non-naturally occurring fusion protein can comprise IL-22 and a carrier, and optionally a spacer coupling the IL-22 to the carrier. The non-naturally occurring fusion protein can be a protein comprising, consisting essentially of, or consisting of an amino acid sequence having at least 80%, 85%. 90%, 95%, 98%, or 99% sequence identity, or having 100% sequence identity, to an amino acid sequence set forth in SEQ ID NOS: 14-21, 24, or 25. Advantages of the methods and compositions described herein include maintaining high purity and biological activity of the purified polypeptides or proteins.

Specific advantages of the herein disclosed methods include: a) high biological activity of the non-naturally occurring fusion proteins due to correct folding using specifically developed folding buffers; b) high chemical purity of the purified non-naturally occurring fusion proteins paired with low toxicity; c) high recovery yield of the material subjected to purification; d) reproducibility of the results enables reliable production and supply; e) manufacturability and scalability to multi-gram and multi-kilogram scale for clinical and commercial applications; f) sustainable use of materials and resources provide a cost- and logistically effective purification method for clinically relevant molecules. Additionally, improved manufacturing methods can increase the speed at which these purified proteins can be developed for therapeutic use (FIG. 22).

Figure 17:
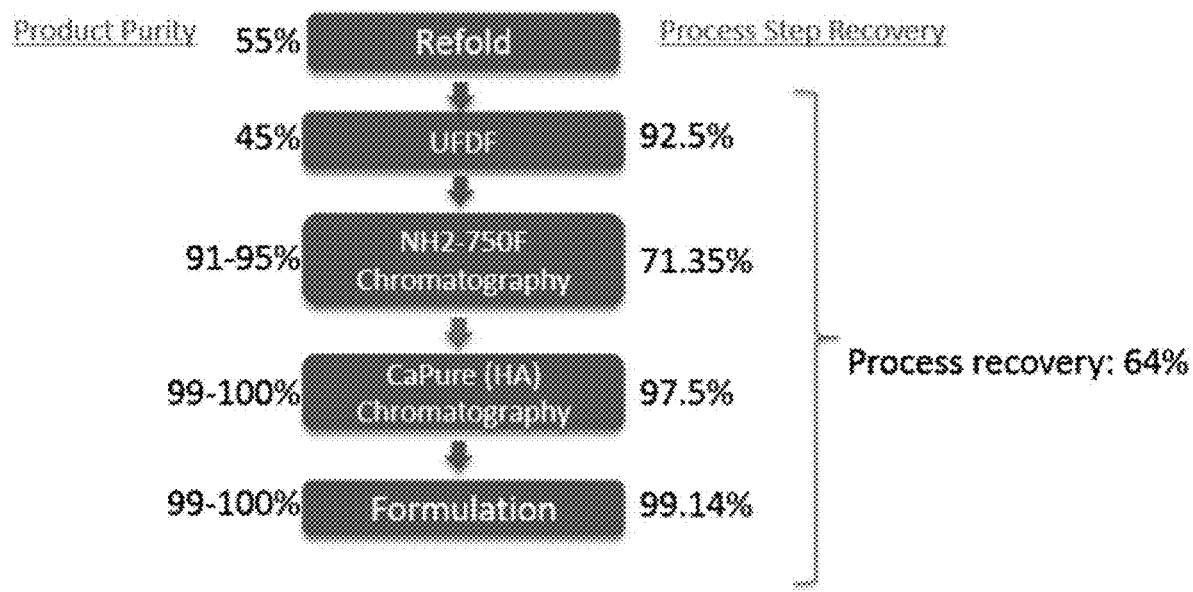
FIG. 17 illustrates a flow chart summarizing the refolding, purification, and formulation of heterologous fusion proteins described herein, such as, for example SEQ ID NOS: 14-21, and fusion proteins comprising a carrier of SEQ ID NO: 1-9, 22, or 23.

An exemplary process for purification of the non-naturally occurring fusion proteins described herein is shown in FIG. 17, which further illustrates exemplary purity and recovery amounts for the non-naturally occurring fusion protein at each stage in the purification process.

As used herein, "purity," indicates a level of the desired protein (e.g. non-naturally occurring fusion protein) or desired form of the protein (e.g. a monomer of the non-naturally occurring fusion protein, a corrected folded non-naturally occurring fusion protein, or a combination thereof) in a composition which can also comprise non-desired proteins or non-desired forms of the protein (e.g. an aggregate of the non-naturally occurring fusion protein, an incorrectly folded protein, or a combination thereof). The level can be represented by a percentage (%) of the desired protein or desired form of the protein. For example, the purity can be greater than 40%, 50%, 60%, 70%, 80%, 90%, 95%, or 99%, or can be 100%. The term "purified" can be used to indicate a composition which has experienced an increase in purity. An increase in purity can be due to purification procedures described herein, such as anion exchange chromatography, hydroxyapatite chromatography, cation exchange chromatography, or a combination thereof.

In some cases, the methods and compositions of the present disclosure comprise the use of at least two chromatography columns that are performed in tandem, follow by a concentration/buffer exchange step (ultrafiltration/diafiltration (UF/DF) to concentrate and buffer exchange the solution). The chromatography columns can be low pressure chromatography systems, such as the AKTA Avant 150 column or an AKTA Pilot column from General Electric (GE). In some cases, at least one column contains an anion exchange resin (e.g. NH$_2$-750F resin) and at least one column contains a hydroxyapatite resin (e.g., CaPure® resin). In some case, at least one column containing the anion exchange resin is used for the capture step, whereas the at least one column containing the hydroxyapatite resin is used for the polishing step. In some cases, instead (or in addition to) the hydroxyapatite column, a cation exchange column may be used. For instance, in some embodiments, the cation exchange column with a sulfate-functionalized polymethacrylate resin, such as TOYOPEARL Sulfate-650F. The purity of the solubilized protein can increase from 44% to 47% following UF/DF to from 93% to 97% following anion exchange chromatography to at least 99% following hydroxyapatite chromatography. The recovery of the solubilized protein can increase from 70% to 73% following the anion exchange chromatography to at least 97% following the hydroxyapatite chromatography.

Isolation of Non-Naturally Occurring Fusion Proteins from Inclusion Bodies

In some embodiments, the non-naturally occurring fusion proteins to be purified are isolated from inclusion bodies (IBs). IBs as described herein may be nuclear or cytoplasmic aggregates of stable substances, such as proteins and polypeptides. In some embodiments, double-washed inclusion bodies (DWIB) comprising the non-naturally occurring fusion proteins (e.g., SEQ ID NOs: 14-21) from fermentation is resuspended in a specific buffer system (see EXAMPLE 6).

In some cases, the concentration of DWIB is from about 0.5 g DWIB/100 mL buffer to about 5 g DWIB/10 mL buffer. In some cases, the concentration of DWIB is from about 2 g DWIB/50 mL buffer to about 5 g DWIB/50 mL buffer. In some cases, the concentration of DWIB is from about 1 g DWIB/20 mL buffer to about 1 g DWIB/10 mL buffer. In some cases, the concentration of DWIB is at least 1 g DWIB/100 mL buffer. In some cases, the concentration of DWIB is at least 1 g DWIB/10 mL buffer.

The buffer system for resuspension may comprise a variety of buffer agents and ingredients. In some cases, the buffer system for resuspension comprises Guanidine/HCl (Gu-HCl) at a concentration of at least 1M, at least 2 M, at least 4M, at least 6 M, at least 8M. In some cases, the concentration of Gu-HCl is from about 4 M to about 8 M. In some cases, the buffer system for resuspension comprises Tris buffer, wherein the concentration of Tris is at least 5 mM, at least 10 mM, at least 20 mM, at least 50 mM, or at least 100 mM. In some cases, the Tris buffer has a concentration from about 40 mM to about 60 mM. The Tris buffer can be Tris-HCl. The Tris-HCl can have a pH from 8.0 to 8.5. The Tris-HCl can have a pH of 8.2. In some cases, the buffer system for resuspension comprises dithiothreitol (DTT). The DTT can have a concentration of at least 7 mM, 8 mM, 9 mM, 10 mM, 20 mM, 30 mM, 40 mM, 50 mM, 60 mM, or 70 mM. The DDT can have a concentration from 7 mM to 11 mM, from 8 mM to 10 mM, or from 9 mM to 10 mM. In some cases, the buffer system for resuspension comprises ethylenediaminetetraacetic acid (EDTA). The EDTA can have a concentration of at least 1 mM, 1.5 mM, 2 mM, or 2.5 mM. The EDTA can have a concentration from 1 mM to 2.5 mM or from 1.9 mM to 2.1 mM. In some embodiments, the buffer system for resuspension comprises, consists essentially of, or consists of a Tris buffer, Gu-HCl, and DTT. The buffer system used for resuspension may have a pH from about 6 to about 10. In some cases, the buffer system has a pH from about 7.5 to about 8.5. In some cases, the pH of the buffer system is at least 7. In some cases, the pH of the buffer system is at least 8. In some cases, the pH of the buffer system is at least 8.5.

Reduction of Solubilized Non-Naturally Occurring Fusion Proteins

A reducing agent may be added to the resuspension solution. The reducing agent may be dithiothreitol (DTT). The amount of reducing agent used may depend on the volume of the resuspension solution and the fusion protein present in that solution. In some cases, the amount of reducing agent used is from about 0.025 mM to about 50 mM, from 0.5 mM to 30 mM, from 1 mM to 10 mM. In some cases, the amount of reducing agent used is at least (or between) 2 mM, 3 mM, 4 mM, 5 mM, 6 mM, 7 mM, 8 mM, 9 mM, or 10 mM.

The solubilized non-naturally occurring fusion protein (e.g., SEQ ID NOs: 14-21) solution may be incubated at various temperatures ranging from about 2° C. to about 40° C. In some cases, the protein solution may be incubated at room temperature (RT). Incubation may be performed while the solution is stirring. The solution may be stirred on a magnetic stir-plate and then centrifuged. Centrifugation may be performed at about 1,000×g to about 20,000×g. In some cases, centrifugation is performed at 15,970×g for 90 minutes at 4° C. The incubation time may vary from about 20 minutes to about 180 minutes, depending on the concentration of ingredients, the concentration of the fusion protein (e.g., SEQ ID NOs: 14-21).

Protein concentration in various solutions throughout the methods and procedures as described herein may be performed using Bradford assay. Concentration of the solubilized non-naturally occurring fusion protein may be from about 1 mg/mL to about 50 mg/mL. In some cases, the final concentration of the solubilized non-naturally occurring fusion protein may be from about 3 mg/mL to about 30 mg/mL. In some cases, the final concentration of the solubilized non-naturally occurring fusion protein may be from about 5 mg/mL to about 20 mg/mL. In some cases, the final concentration of the solubilized non-naturally occurring fusion protein may be at least 15 mg/mL.

Refolding of Non-Naturally Occurring Fusion Proteins

The non-naturally occurring fusion proteins of the present disclosure may exert their biological activity due to their specific three-dimensional structure or folding. Therefore, refolding of these polypeptides can be important in developing these polypeptides for pharmaceutical applications. Desirable refolding of a fusion protein comprising at least a carrier and an IL-22 can comprise refolding of the carrier or the IL-22 into a tertiary structure similar to a tertiary structure of a homologous naturally occurring carrier or IL-22 sequence or a tertiary structure which results in maintenance of the desired activity of the carrier (e.g. transcytosis of the fusion protein) and IL-22. The methods described herein can comprise refolding the solubilized non-naturally occurring fusion protein to produce refolded non-naturally occurring fusion protein. The refolding can occur prior to performing the anion exchange chromatography.

The solubilized protein (e.g., SEQ ID NOs: 14-21) may be added to a refolding solution, also referred to as a refold buffer solution. The amount of solubilized protein used may be from 0.1 mg/mL to 1 mg/mL, 1 mg/mL to 100 mg/mL, from 1 mg/mL to 50 mg/mL, from 1 mg/mL to 10 mg/mL, from 5 mg/mL to 20 mg/mL, or about 15 mg/mL. The amount of solubilized protein can be at least 1, 2, 3, 4, 5, 6, 7, 8, 9, or 10 mg/mL. The amount of solubilized protein can be no more than 0.1, 0.5, 1, 5, 10, 20, 30, 40, 50, 60, 70, 80, 90, or 100 mg/mL. The refolding solution can have a pH of between 7.5 and 8.5, or about 7.0.

The refold buffer solution can comprise an amino acid, a polyol, a salt, a sugar, a redox reagent, a chaotrope, or a combination thereof. The amino acid can be proline, glycine, arginine, or alanine. The polyol can be glycerol. The salt can be sodium chloride (NaCl), potassium chloride (KCl), or magnesium chloride ($MgCl_2$). The sugar can be glucose or sucrose. The redox reagent can be cysteine, cystamine, glutathione, dithiothreitol (DTT), or copper sulfate ($CuSO_4$). In some embodiments, the refold buffer comprises Tris-base, Arginine-HCl, urea, EDTA, glycerol, L-Cysteine, Cystamine-2HCl, DTT, Gu-HCl, or a combination thereof. In some embodiments, the refold buffer comprises, consists essentially of, or consists of Tris pH 8.5, arginine glycerol, cysteine, and cystamine. Concentrations of Tris buffer may range from about 20 mM to about 200 mM with pH ranging from about 6 to about 9. Concentrations of Arginine-HCl may range from about 0.1 M to about 1.5 M, from about 0.75 M to 1.25M, or about 1.0 M. Concentrations of urea may range from about 0.5 M to 1.5 M. Concentrations of EDTA may range from 1 mM to 3 mM. Concentrations of glycerol may range from about 2% v/v to about 20% v/v, from about 8% v/v to about 12% v/v, or about 10% v/v. Concentrations of cysteine can be from 1 mM to 5 mM, from 2 mM to 4 mM, or about 3 mM. The cysteine can be L-cysteine. Concentrations of cystamine may range from about 0.5 mM to about 5 mM, from about 1 mM to about 4 mM, or about 3 mM. The cystamine can be cystamine-2HCl. Concentrations of DTT may range from about 0.1 mM to about 1 mM. Concentrations of Gu-HCl may range from about 50 mM to about 500 mM. The refold buffer can comprise, consist essentially of, or consist of Tris, L-arginine, urea, EDTA, cysteine, and cystamine. The refold buffer can comprise, consist essentially of, or consist of 100 mM Tris pH 8.5, 1M arginine, 10% (v/v) glycerol, 3 mM L-Cysteine, and 1 mM Cystamine-2HCl. The solubilized non-naturally occurring fusion protein can be added to the refold buffer to produce a refold mixture. The concentration of the non-naturally occurring fusion protein, after addition to the refold mixture, can be from about 0.1 mg/mL to 1.0 mg/mL, 0.5/mL mg to 1.5 mg/mL, from 0.75 mg/mL to 1.25 mg/mL, or about 1 mg/mL. The concentration of the non-naturally occurring fusion protein in the refold mixture can be less than 0.5 mg/mL, 0.6 mg/mL, 0.7 mg/mL, 0.8 mg/mL, 0.9 mg/mL or 1.0 mg/mL.

In various embodiments, a volume of about 100 mL to about 10,000 L refold buffer is used. In some cases, the volume is from about 50 mL to about 1500 L. In some cases, the volume is from about 10 L to about 300 L. In some cases, the volume is at least 200 L.

Figure 18:
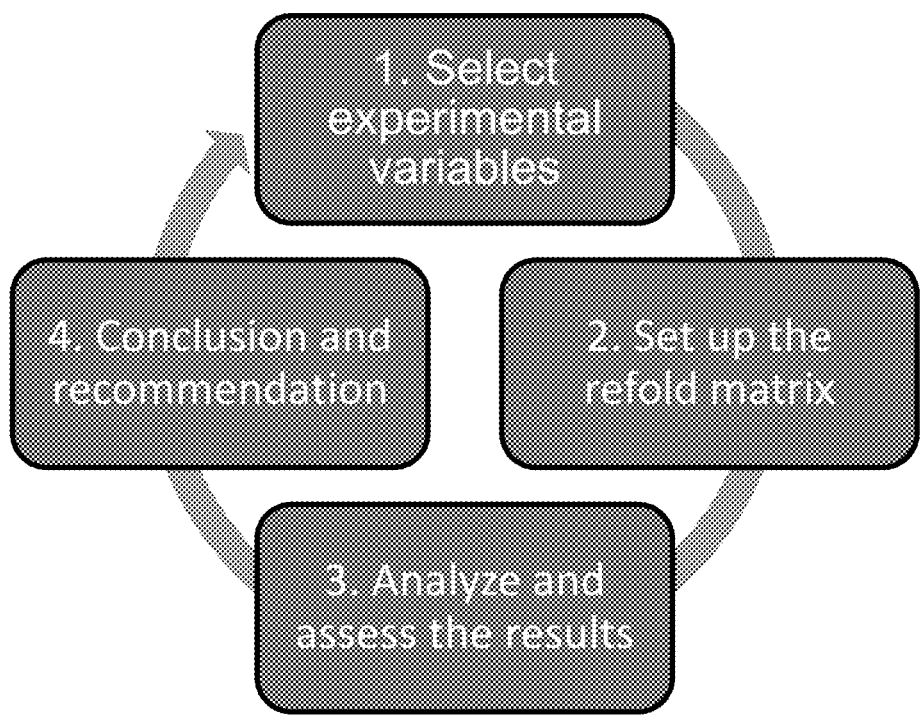
FIG. 18 illustrates iterative optimization for the improved refolding efficiency of the construct of SEQ ID NO: 15.

The refold solution may have a certain temperature. For example, the refold solution may be pre-chilled to about 2-12° C. In some cases, the refold solution is pre-chilled to at least about 3° C. This refolding process may be optimized depending on the protein used and the application (FIG. 18).

In some embodiments of the present disclosure, the refolding mixture is incubated for a certain period of time. In some cases, the process may be about one hour, two hours, four hours, five hours, or 20 hours. In some cases, the refolding process takes about 15 to about 25 hours. In some cases, a peristaltic pump set at a certain flow rate depending on the constitution of the solution (e.g., concentration or volume) to deliver the solubilized material into the refold solution. In some cases, a peristaltic pump set at a flow rate of 60-80 ml/min. The optimization process utilized a design of experiments (DOE) of 15 different matrices, 12 variables and 200 refold reactions. Decisions were made by a process of elimination.

In various embodiments, quantitative analysis may be performed to determine the amount or percentage of correctly folded protein in the solution comprising the refolded non-naturally occurring fusion proteins. In some instances, SEC-HPLC is performed to determine the amount of the properly folded non-naturally occurring fusion protein present in the refold samples.

The purity of the refolded non-naturally occurring fusion protein can be from 45% to 65%, from 40% to 60%, or from 45% to 55%. The purity of the refolded non-naturally occurring fusion protein can be at least 40%, 45%, 50%, or 55%.

Tangential Flow Filtration (TFF) of Solubilized IL-22 Delivery Constructs

In various embodiments, protein refolding is performed in combination with or prior to tangential flow filtration (TFF) systems (e.g., Millipore) and ultrafiltration/diafiltration (UF/DF) systems with certain molecular weight cut-offs (MWCOs).

Protein refolding mixture may be subsequently processed by TFF to concentrate and buffer exchange the solution. In some cases, the process is performed by ultrafiltration/diafiltration (UF/DF). During ultrafiltration, the solution can be concentrated from 8-fold to 12-fold, or about 10-fold. Ultrafiltration can be followed by a 5-fold buffer exchange during diafiltration with a diafiltration buffer. The UF/DF can comprise the use of 10-20 kDa MWCO Millipore Ultracell Pellican3 filters, with 1-2 $m^2$ TFF flat sheet cassettes. The specific parameters (i.e. TMP) may be varied depending on the molecular characteristics of the protein. The diafiltration buffer can comprise from 10-25 mM Tris-base at pH from about 7 to about 8.5, and from 50-200 mM NaCl. The specific parameters may be varied depending on the molecular characteristics of the protein. The final volume at the end of the UF/DF process may be from about 5 L to about 100 L. In some cases, the final volume ranges from about 10 to about 50 L. In some cases, the final volume ranges from about 80 mL to about 10 L.

Subsequent filtration may be carried out using a flow filtration system. In some cases, the flow filtration system is an AkroPac® filter system and ColeParmer® peristaltic pump and tubing. Bradford assay may be performed to determine the protein concentration, yield, and step recovery.

In various embodiments, quantitative analysis may be performed to determine the amount or percentage of correctly folded protein in the sample solutions. In some instances, SEC-HPLC is performed to determine the amount of the properly folded non-naturally occurring fusion protein present in the refold and UF/DF samples.

The purity of a solution comprising the refolded non-naturally occurring fusion protein following UF/DF can be from 35% to 55%, from 40% to 50%, from 43% to 47%, or about 45%. The purity of a solution comprising the refolded non-naturally occurring fusion protein following UF/DF can be at least 35%, 40%, or 45%. The recovery of the solubilized, refolded non-naturally occurring fusion protein following UF/DF can be from 87% to 97%, from 90% to 94%, from 92% to 93%, or about 92.5%. (Other concentration and buffer exchange systems can also be used.)

Purification and Recovery of Non-Naturally Occurring Fusion Proteins

As previously described, the use of two chromatography methods in tandem, such as an anion exchange chromatography and a hydroxyapatite chromatography (or alternatively cation exchange chromatography), can result in increased purity and recovery of the non-naturally occurring fusion protein, such as the IL-22 delivery constructs described herein, from solution. In various embodiments of the present disclosure, the chromatography specifics (e.g., column type, resin, flow rate, buffer systems, gradient, and conductivity) are determined and optimized depending on various parameters, e.g., the protein to be purified. A variety of purification columns may be used for protein purification as described herein.

Anion Exchange Chromatography

The methods described herein can comprise performing anion exchange chromatography (AEX) on a mixture comprising the non-naturally occurring fusion protein. The mixture can be a solution comprising the refolded non-naturally fusion protein. Performing anion exchange chromatography can produce a first fraction comprising the non-naturally occurring fusion protein.

A variety of resins may be used in combination with the methods and compositions of the present disclosure. In some cases, the resin comprises amine-functionalized polymethylacrylate beads. In some cases, anion exchange resin $NH_2$-750F is used for protein purification. A column with a bed-height of at least 15 cm, 20 cm, 25 cm, or 30 cm can be filled with the resin. A column with a bed-height from 10 to 50 cm may be filled with resin in a way to ensure a column volume that may facilitate an appropriate dynamic binding capacity (e.g., >20 g/L) to enable production of the desired quantity of protein. In some cases, the dynamic binding capacity of the column is from 5 g/L to 100 g/L, from 20 g/L to about 50 g/L, from 15 g/L to 30 g/L, or from 20 g/L to 25 g/L.

Buffer systems used for elution (e.g., gradient elution) in anion exchange chromatography may comprise one, two, three, or four different buffer solutions (e.g., Buffers A through D). In some embodiments, two buffers are used in the anion exchange chromatography and are referred to herein as Buffer A and Buffer B. In some cases, a buffer solution comprises Tris (e.g., 10-50 mM, pH 7-9), and/or NaCl (e.g., 0.1-5 M). In some cases, the buffer solution further comprises glycerol. In some embodiments, the buffer solution(s) used in anion exchange chromatography, such as for example Buffer A or Buffer B, comprises, consists essentially of, or consists of Tris pH 7.5 and NaCl, and optionally, glycerol.

Buffer A can comprise from 10 mM to 30 mM, from 15 mM to 25 mM, from 19 mM to 21 mM, or about 20 mM Tris pH 7.5. Buffer A can comprise from 0.25 M to 0.95 M, from 0.35 M to 0.75M, from 0.45 M to 0.55 M, about 0.5 M, from 0.65 M to 0.75 M, or about 0.7 M NaCl. Buffer B can comprise from 10 mM to 30 mM, from 15 mM to 25 mM, from 19 mM to 21 mM, or about 20 mM Tris pH 7.5. Buffer B can comprise from 1 M to 3 M, from 1.5 M to 2.5 M, from 1.9 M to 2.1 M, or about 2 M NaCl. Buffer A can further comprise from 8% to 12%, from 9% to 11%, or about 10% (v/v) glycerol. Buffer B can further comprise from 8% to 12%, from 9% to 11%, or about 10% (v/v) glycerol.

For anion exchange chromatography of SEQ ID NO: 15, Buffer A can comprise 20 mM Tris pH 7.5 and 0.5 M NaCl and Buffer B can comprise 20 mM Tris pH 7.5 and 2.0 M NaCl (TABLE 4). For anion exchange chromatography of SEQ ID NO: 17, Buffer A can comprise 20 mM Tris pH 7.5 and 0.5 M NaCl and Buffer B can comprise 20 mM Tris pH 7.5 and 2.0 M NaCl. For anion exchange chromatography of SEQ ID NO: 14, Buffer A can comprise 20 mM Tris pH 7.5, 0.7 M NaCl, and 10% (v/v) glycerol, and Buffer B can comprise 20 mM Tris pH 7.5, 2.0 M NaCl, and 10% (v/v) glycerol (TABLE 5).

In some embodiments, a certain volume of a salt solution is added to the protein solution. In some cases, NaCl solution with a concentration raging from about 0.1 to about 5 M is added to the protein solution.

Protein solutions may be loaded onto the column such that a specific flow-rate and a specific column residence time may be observed to ensure appropriate interaction of the protein and the solid phase (e.g., resin). In some cases, the flow rate is controlled such that a column residence time is from about 30 seconds to about 6 minutes, or about 5 minutes. The column residence time can be at least 30 seconds, or 1, 2, 3, 4, or 5 minutes. The column residence time can be no more than 3, 4, 5, 6, 7, 8, 9, or 10 minutes. The flow-through may be collected and analyzed to determine if there is unbound protein, which is considered as a loss. For protein analysis and purification, the absorbance at about 280 nm is determined for protein concentration and SEC-HPLC for protein purity.

In some embodiments, a percentage (e.g., 0-100%) or flow rate (e.g., 1-10 mL/min) of a first buffer is combined with a second buffer to achieve a specific final flow rate (e.g., 1-10 mL/min) of the column purification system. For example, a linear gradient of 20 column volumes (CV) from 0.0-62.5% B (100-37.5% A), followed by a step gradient to 100% B (0% A) for additional 5 CV is performed for protein purification. In some cases, a gradient of 0-75% B (100-25% A) 40 CV, Step 100% B, 10 CV may be performed as an elution gradient indicating 91-93% pure protein and a recovery of >90%.

The purity of the non-naturally occurring fusion protein in the first fraction can be from 90% to 99% or from 91% to 95%. The purity of the solubilized non-naturally occurring fusion protein in the first fraction can be at least 90%, 91%, 92%, 93%, 94%, or 95%. The recovery of the solubilized non-naturally occurring fusion protein in the first fraction can be from 61% to 81%, from 66% to 76%, or from 71% to 72%.

Cation Exchange Chromatography or Hydroxyapatite Chromatography

The methods described herein can further comprise subjecting the first fraction obtained following the anion exchange chromatography to a cation exchange resin to obtain a second fraction comprising the non-naturally occurring fusion protein. The cation exchange resin can be a sulfate-functionalized methacrylate resin. The cation exchange resin can be a TOYOPEARL® Sulfate-650F resin.

The methods described herein can additionally or alternatively comprise subjecting the first fraction obtained following the anion exchange chromatography to a hydroxyapatite resin to obtain a second fraction comprising the non-naturally occurring fusion protein. The hydroxyapatite resin can be a cation exchange resin further comprising a calcium affinity. The hydroxyapaptite resin can comprise calcium phosphate. The hydroxyapaptite resin can comprise a chemical formula of: $Ca_{10}(PO_4)_6(OH)_2$. The hydroxyapaptite resin can comprise a particle size from 30 μm to 50 μm, from 35 μm to 45 μm, or about 39 μm. The hydroxyapaptite resin can be the CaPure® resin.

Advantages of the CaPure® resin can include a) salt tolerance, allowing protein adsorption at high conductivity in aqueous solutions; b) no preparation of proteins (e.g., fusion proteins such as SEQ ID NO: 14-21) required prior to load; c) results in a high recovery (>90%); d) high binding capacity (>20 mg/mL resin); e) increases purity by removal of low molecular weight (LMW) impurities; and f) ensures endotoxin clearance (<1.0 EU/mg).

The cation exchange resin or hydroxyapatite resin can be used to pack a chromatograph column. The column can comprise a bed height from 10 cm to 50 cm, or about 20 cm. The column can comprise a bed height of at least 10 cm, 15 cm, 20 cm, 25 cm, or 30 cm. The column can comprise a bed height of no more than 20 cm, 30 cm, 40 cm, or 50 cm. In some cases, the hydroxyapatite mixed-mode resin CaPure® is used to pack a column with a bed-height of 10-50 cm, ensuring a column volume that facilitates a dynamic binding capacity of maximum 10-100 g/L to enable production of the desired quantity of protein.

Buffer systems used for elution (e.g., gradient elution) in hydroxyapatite chromatography may comprise one, two, three, or four different buffer solutions (e.g., Buffers A through D). In some embodiments, two buffers are used in the hydroxyapatite chromatography and are referred to herein as Buffer A and Buffer B. In some cases, a buffer solution comprises Tris (e.g., 10-50 mM, pH 7-9), and/or NaCl (e.g., 0.1-5 M). In some cases, the buffer solution further comprises glycerol. In some embodiments, a first buffer solution used in hydroxyapatite chromatography, such as for example Buffer A, comprises, consists essentially of, or consists of Tris pH 7.5, NaCl, and $CaCl_2$. In some embodiments, a second buffer solution used in hydroxyapatite chromatography, such as for example Buffer B, comprises, consists essentially of, or consists of sodium phosphate pH 7.0, NaCl, and $CaCl_2$.

Buffer A can comprise from 10 mM to 30 mM, from 15 mM to 25 mM, from 19 mM to 21 mM, or about 20 mM Tris pH 7.5. Buffer A can comprise from 80 mM to 120 mM, from 90 mM to 110 mM, or about 100 mM NaCl. Buffer A can comprise from 0.5 mM to 1.5 mM, from 0.75 mM to 1.25 mM, from 0.9 mM to 1.1 mM, or about 1 mM of $CaCl_2$. Buffer B can comprise from 150 mM to 250 mM, from 175 mM to 225 mM, from 190 mM to 210 mM, or about 200 mM sodium phosphate pH 7.0. Buffer B can comprise from 50 mM to 150 mM, from 75 mM to 125 mM, from 90 mM to 110 mM, or about 100 mM NaCl. Buffer B can comprise from 0.5 mM to 1.5 mM, from 0.75 mM to 1.25 mM, from 0.9 mM to 1.1 mM, or about 1 mM of $CaCl_2$.

For hydroxyapatite chromatography of SEQ ID NO: 15, Buffer A can comprise 20 mM Tris pH 7.5, 100 mM NaCl, and 1 mM $CaCl_2$ and Buffer B can comprise 200 mM sodium phosphate pH 7.0, 100 mM NaCl, and 1 mM $CaCl_2$ (TABLE 6). For hydroxyapatite chromatography of SEQ ID NO: 17, Buffer A can comprise 20 mM Tris pH 7.5, 100 mM NaCl, and 1 mM $CaCl_2$ and Buffer B can comprise 200 mM sodium phosphate pH 7.0, 100 mM NaCl, and 1 mM $CaCl_2$. For hydroxyapatite chromatography of SEQ ID NO: 14, Buffer A can comprise 20 mM Tris pH 7.5, 100 mM NaCl, and 1 mM $CaCl_2$ and Buffer B can comprise 200 mM sodium phosphate pH 7.0, 100 mM NaCl, and 1 mM $CaCl_2$ (TABLE 7).

The purity of the solubilized protein following the use of cation exchange resin or hydroxyapatite resin can be from 99% to 100%. The purity of the solubilized protein following the use of hydroxyapatite resin can be at least 95%, 96%, 97%, 98%, 99%, or 100%. The recovery of the solubilized protein following the use of hydroxyapatite resin can be from 85% to 100%, from 96% to 99%, or from 97% to 98%. The hydroxyapatite resin can be CaPure®.

Fractions collected during column chromatography that contain the purified compound (e.g., fusion protein) may be concentrated and formulated for administration using buffer exchange or diafiltration. For example, fractions collected during CaPure® can be concentrated and formulated using a TFF system (e.g., Pall corporation) to concentrate the protein. The protein can be concentrated to a final concentration of 20 mg/mL followed by 5-fold buffer exchange. The filtration process may be performed using ultrafiltration/diafiltration (UF/DF) and filters with a 10 kDa MWCO Millipore Pellican3, 0.114 $m^2$ TFF flat sheet cassettes. The MWCO of the filtration system may be varied depending on the protein (e.g., molecular weight) to be purified. The diafiltration buffer may consist of 10-20 mM sodium phosphate at about pH 7.0, 50-100 mM NaCl. Formulated SEQ ID NOS: 14-21 may subsequently be filtered using a flow filtration system employing an AkroPac® 0.8/0.2 um filter and a Cole-Parmer® peristaltic pump and tubing. Purified and formulated protein may be stored in aliquots at −80° C. until further use.

In specific embodiments, proteins analyzed by SEC-HPLC may show above 97% purity (typically >98%) using TSKgel GW3000SWXL, 5 μm, 7.8 mm ID×30.0 cm L column (Tosoh Bioscience, 8541).

Protein Analysis

Samples from different fractions may be analyzed by SDS-PAGE using the Bio-Rad ChemiDoc™ MP imaging system, and the fractions collected during column chromatography may be analyzed for protein content using Thermo Fisher Nanodrop One™. General techniques for protein detection or analysis include gel electrophoresis, fluorescence microscopy, capillary electrophoresis, mass spectrometry, electrophoretic mobility-shift assay, or nuclear magnetic resonance.

Methods of Treatment

In various embodiments of the present disclosure, pharmaceutical compositions comprising the fusion molecules of the disclosure are provided for use in treating and/or preventing inflammatory diseases. These pharmaceutical compositions can be formulated for oral delivery. "Inflammatory diseases" may include all diseases associated with acute or chronic inflammation. Acute inflammation is the initial response of the body to harmful stimuli and results from an increased movement of plasma and leukocytes (such as e.g. granulocytes) from the blood into the injured tissues. A number of biochemical events propagates and matures the inflammatory response, involving the local vascular system, the immune system, and various cells within the injured tissue. Prolonged inflammation is referred to as chronic inflammation, which leads to a progressive shift in the type of cells present at the site of inflammation and is characterized by simultaneous destruction and healing of the tissue from the inflammatory process. Inflammatory diseases can be caused by e.g. burns, chemical irritants, frostbite, toxins, infections by pathogens, physical injury, immune reactions due to hypersensitivity, ionizing radiation, or foreign bodies, such as e.g. splinters, dirt and debris. In some embodiments, the inflammatory disease is epithelial cell injury, hepatitis, obesity, fatty liver disease, liver inflammation, pancreatitis, Crohn's disease, fistulizing Crohn's disease, ulcerative colitis, mild-to-moderate ulcerative colitis, moderate-to-severe ulcerative colitis, pouchitis, proctitis, multiple sclerosis, systemic lupus erythematosus, graft versus host disease, rheumatoid arthritis, or psoriasis.

Further described herein are methods for treating a disease or condition in a subject, comprising administering to the subject the non-naturally occurring fusion protein. In some embodiments, the disease or condition is epithelial cell injury, hepatitis, obesity, fatty liver disease, liver inflammation, pancreatitis, Crohn's disease, fistulizing Crohn's disease, ulcerative colitis, mild-to-moderate ulcerative colitis, moderate-to-severe ulcerative colitis, pouchitis, proctitis, multiple sclerosis, systemic lupus erythematosus, graft versus host disease, rheumatoid arthritis, or psoriasis. The non-naturally occurring fusion protein can be oral administered to the subject. The subject can be human.

EXAMPLES

These examples are provided for illustrative purposes only and not to limit the scope of the claims provided herein.

Example 1

Expression of a Delivery Construct

In this example, the preparation of a delivery construct as a single amino acid sequence comprising a carrier sequence derived from Cholix, a spacer sequence, and a therapeutic payload, is generally described.

First, a nucleic acid sequence encoding a delivery construct of SEQ ID NO: 15 was amplified by PCR, incorporating restriction enzymes pairs of NdeI and EcoRI, PstI and PstI, AgeI and EcoRI, or PstI and EcoRI sites at two ends of the PCR products. After restriction enzyme digestion, the PCR products were cloned into an appropriate plasmid for cellular expression, which was digested with the corresponding restriction enzyme pairs. The plasmid encoded a delivery construct comprising the amino acid sequence set forth in SEQ ID NO: 15.

The delivery construct was expressed as follows: E. coli BL21(DE3) pLysS competent cells (Novagen, Madison, Wis.) were transformed using a standard heat-shock method in the presence of the appropriate plasmid to generate delivery construct expression cells, selected on ampicillin-containing media, and isolated and grown in Luria-Bertani broth (Difco; Becton Dickinson, Franklin Lakes, N.J.) with antibiotic, then induced for protein expression by the addition of 1 mM isopropyl-D-thiogalactopyranoside (IPTG) at OD 0.6. Two hours following IPTG induction, cells were harvested by centrifugation at 5,000 rpm for 10 min. Inclusion bodies were isolated following cell lysis and washed twice with water at a ratio of 1 g/10 mL. The pellet from the cell lysis was resuspended with water followed by one hour centrifugation at 10,000 rpm at 4° C. This wash was then repeated once. Double-washed D3 (DWIB) therein were solubilized in a buffer containing 50 mM Tris-HCl (pH 8.2), 6 M guanidine HCl, and 10 mM dithiothreitol (DTT). Solubilized material was then diluted into a refold buffer containing 0.1 M Tris (pH=8.5 at 4° C.), 1.0 M L-arginine, 10% glycerol, 3 mM L-cysteine, 1 mM cystamine-2HCl. The refolded protein with SEQ ID NO: 15 was purified by anion exchange chromatography (Q sepharose Ion Exchange) and Superdex 200 Gel Filtration chromatography (Amersham Biosciences, Inc., Sweden). The purity of the protein was assessed by SDS-PAGE and analytic HPLC (Agilent, Inc. Palo Alto, Calif.).

The delivery construct was evaluated to verify the proper folding with regard to its anticipated molecular size. Following induction, expressed protein was collected from inclusion bodies. Using the inclusion bodies, the extent of expression of the delivery construct was verified by gel electrophoresis, and the apparent molecular weight was compared to the calculated mass.

The results demonstrated stable and efficient production of a functional delivery construct in high yield and purity.

Example 2

In Vitro Model Assessing Transport of Payload Across Epithelial Cell Monolayers

This example demonstrates an in vitro model designed to evaluate the transport properties of payloads or delivery constructs described herein.

FIG. 1 schematically shows a setup comprising an apical chamber above the epithelial cell monolayer and a basal chamber below such epithelial cell monolayer.

For apical to basolateral permeability, test articles (e.g., delivery construct, payload, etc.) were added to the apical (A) side and the amount of permeation was determined on the basolateral (B) side. For basolateral to apical permeability, test articles were added to the basolateral (B) side and amount of permeation was determined on the apical (A) side.

Data can be expressed as permeability (Papp) according to the following equation: Papp=(dQ/dt)/(C0*A). Q/dt is a rate of permeation, C0 is initial concentration of test article, and A is the area of the monolayer. An efflux transport ratio (Re) can be calculated according to the following equation: (Re)=Papp(B−A)/Papp(A−B). Re>2 can indicate a potential substrate for P-gp or other active efflux transporters.

SMI-100 or Caco-2 cells can be used to assess the transcytosis function of a carrier or delivery construct in vitro.

For Caco-2 cells, an ELISA assay was performed to evaluate the ability of a carrier or delivery construct to move across Caco-2 cell monolayers via transcytosis. Caco-2 (ATCC HTB-37™) cells were maintained in 5% $CO_2$ at 37° C. in complete media: Dulbecco's modified Eagle's medium F12 (DMEM F12) supplemented with 10% fetal bovine serum, 2.5 mM glutamine, 100 U of penicillin/ml, and 100 µg of streptomycin/ml (Gibco BRL, Grand Island, N.Y.). Cells were fed every 2 to 3 days with this media (designated complete medium) and passaged every 5 to 7 days. For assays, cells were seeded into 24- or 96-well plates and grown to confluence.

Caco-2 cells were grown as confluent monolayers on collagen-coated 0.4-µm pore size polycarbonate membrane transwell supports (Corning-Costar, Cambridge, Mass.) and used 18-25 days after attaining a trans-epithelial electrical resistance (TER) of >250 Ω·cm2 as measured using a chopstick Millicell-ERS® voltmeter (Millipore). Apical to basolateral (A→B) transport of a carrier or delivery construct across these monolayer was determined by measuring the amount of transported protein at certain time points (e.g., 15, 30, and 45 minutes) after 4.7 nM, 23.6 nM and 236 nM apical application of delivery construct at 37° C. TER measurements and the extent of 10 kDa fluorescent dextran (measured using an HPLC size exclusion protocol) were used to verify monolayer barrier properties during the course of the study. The extent of transport of the delivery construct (e.g., SEQ ID NO: 15) was determined by titration of collected media in the cell-based cytotoxicity assay. Transported delivery construct was measured by enzyme linked immunosorbant assay (ELISA) using antibodies (e.g., anti-carrier or anti-payload, such as an anti-IL-22 antibody) for capture and detection.

Confluent monolayers of human small intestinal tissues (SMI-100, MatTek Corporation; Ashland, Mass., USA) established on cell culture inserts were allowed to stabilize for 24 h at 37° C. prior to use. Only inserts having a trans-epithelial electric resistance (TEER) of >400 Ω·cm² were considered to have sufficient monolayer integrity for use in studies. A secondary verification of monolayer integrity was performed by assessing suppression of 70 kD dextran transport. The chambers were washed once with transport buffer (PBS). Test molecules, prepared at a concentration of 20 μg/mL, were applied to the apical surface of inserts in 100 μL volumes. Basolateral volumes of 500 μL PBS were replaced at each time point for transport studies. Each experimental condition was performed in triplicate.

Example 3

Carrier-Mediated Transport of IL-22 Across Polarized Gut Epithelial Cells

This example demonstrates that a carrier (SEQ ID NO: 7) can transport an IL-22 payload (SEQ ID NO: 11) across polarized gut epithelial cells in vitro. This example further demonstrates that the carrier with SEQ ID NO: 7 can transport biologically active IL-22 payload across polarized gut epithelial cells and to the lamina propria in vivo.

Figures 7A, 7B:
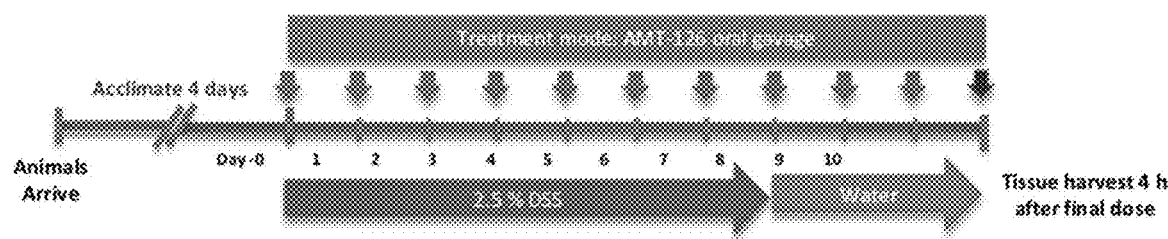
FIG. 7A shows an overview of an in vivo study design and timeline for comparing peroral (p.o.) administration of the delivery construct with SEQ ID NO: 15 at two once daily dose levels, 1 mg/kg and 30 mg/kg, and one once daily administration (intraperitoneal (i.p.)) of rhIL-22 at 4 mg/kg. The in vivo study was performed in Normal chow-fed, 8-10 week old, ~23 g, female C57BL/6 mice. Colitis was chemically induced with 2.5% dextran sulfate sodium (DSS) in drinking water, ad libitum. Study endpoints included percent change in body weight, disease activity index, colon length and weight, and histopathology.
FIG. 7B shows characteristics of the experimental and control groups used in the study described in FIG. 7A.

Transport of delivery construct (SEQ ID NO: 15) across Caco-2 cell monolayers and small intestine epithelial tissue (also referred to herein as SMI-100) was tested by applying the delivery construct to the apical membrane of the epithelial cells, according to EXAMPLE 2 and as illustrated in FIG. 1 for apical (A) to basal (B) transport. Experiments were run in duplicate and samples from the basolateral chamber were collected at 15, 30, and 45 minutes after apical application to determine the amount of transported protein. The amount of transcytosed protein was measured using ELISA assays as described in EXAMPLE 2.

The data in FIG. 2 and FIG. 3 show that a carrier (SEQ ID NO: 7) when coupled to IL-22 (SEQ ID NO: 11) resulted in the transport of IL-22 payload across both Caco-2 (FIG. 2) and SMI-100 (FIG. 3) monolayers in a time-dependent manner, and that the delivery construct resulted in about 2-3 fold more IL-22 crossing the epithelial cells as compared to an IL-22 (SEQ ID NO: 12, M+IL-$22^{34-179}$) alone that was not coupled to a carrier.

For in vivo experiments, transcytosis was tested using male Wistar rats. Male Wistar rats were housed 3-5 per cage with a 12/12 h light/dark cycle and were about 225-275 g (approximately 6-8 weeks old) when placed on study. Experiments were conducted during the light phase using a non-recovery protocol that uses continuous isoflurane anesthesia. A 4-5 cm midline abdominal incision that exposed mid-jejunum regions was conducted. Stock solutions at $3.86\times10^{-5}$ M of delivery construct (SEQ ID NO: 15) were prepared in phosphate buffered saline (PBS), with 50 (per 250 g rat) being administered by intraluminal injection (ILI) using a 29-gauge needle. The injection site mesentery was then marked with a permanent marker. At study termination, a 3-5 mm region that captured the marked intestine segment was isolated and processed for microscopic assessment.

The results of the transcytosis activity of the delivery construct (SEQ ID NO: 15) are shown in FIG. 4, demonstrating that significant amounts of IL-22 payload (SEQ ID NO: 11) crossed an intact and polarized gut epithelium in vivo when provided as part of a delivery construct that includes a cholix-derived carrier (SEQ ID NO: 7) coupled to IL-22. This microscopy image shows transportation of the IL-22 payload (SEQ ID NO: 11) from the apical site of the gut epithelium (highlighted by white arrows #1) to the basal site of the epithelial cells (highlighted by white arrow #2) and into the lamina propria (abbreviated as "l.p.") after luminal application of the delivery construct of SEQ ID NO: 15 to the jejunum of Wistar rats. The image further shows that the IL-22 interacted and bound to a significant extent to IL-22 receptors located on cells within the lamina propria and on the outer basal membrane of the polarized epithelium (highlighted by white arrows #3). IL-22 localization is indicated by white arrows #2 and #3.

Example 4

Recombinant Human IL-22 Binds to Murine IL-22 Receptors

This example demonstrates that recombinant human IL-22 (rhIL-22, SEQ ID NO: 12) binds to murine IL-22 receptors in a dose-dependent manner comparable to recombinant murine IL-22 (rmlL-22).

FIG. 5A demonstrates STAT3 phosphorylation in murine FL83 B cells as a function of agonist concentration (in pM), wherein the agonist is rhIL-22 (SEQ ID NO: 12) or rmlL-22. The data show that rhIL-22 and rmlL-22 induced STAT3 phosphorylation in a concentration-dependent manner, demonstrating that the human IL-22 protein can bind and induce signal transduction through mouse IL-22 receptors as effectively as mouse IL-22.

FIG. 5B demonstrates that rhIL-22 (SEQ ID NO: 12) and rmIL-22 also induced STAT3 phosphorylation in murine Hepa1-6 cells.

FIG. 6A demonstrates that rhIL-22 (SEQ ID NO: 12) and rmIL-22 induced STAT5 phosphorylation in murine FL83 B cells in a dose-dependent manner, demonstrating that the human IL-22 protein can bind and induce signal transduction through mouse IL-22 receptors with efficacy comparable to mouse IL-22.

FIG. 6B demonstrates that rhIL-22 (SEQ ID NO: 12) and rmIL-22 also induced STAT5 phosphorylation in murine Hepa1-6 cells but additional dose ranging will need to be performed in follow up experiments.

These data provide strong evidence that rhIL-22 (e.g., as used in the delivery constructs with SEQ ID NOs: 10 or 11) is capable of activating STAT3 and STAT5 in murine cells, thus providing rationale for using such delivery constructs in murine models to assess IL-22 activity and function.

Example 5

In Vivo Efficacy of the Delivery Construct with SEQ ID NO: 15 in Colitis Model This example demonstrates the in vivo efficacy of the delivery construct with SEQ ID NO: 15 comprising the Cholix derived carrier of SEQ ID NO: 7 coupled to an IL-22 with SEQ ID NO: 11 via a linker with SEQ ID NO: 13 compared to IL-22 alone (SEQ ID NO: 12) in a dextran sulfate sodium (DSS) mouse model.

FIG. 7A shows an overview of an in vivo study design and timeline for comparing peroral (p.o.) administration of the delivery construct of SEQ ID NO: 15 at two once-daily dose levels, 1 mg/kg and 30 mg/kg, and one once daily administration (intraperitoneal (i.p.)) of rhIL-22 at 4 mg/kg. The in vivo study was performed in Normal chow-fed, 8-10 week old, ~23 g, female C57BL/6 mice. Colitis was chemically induced with 2.5% dextran sulfate sodium (DSS) in drinking water, ad libitum. Study endpoints included percent change in body weight, disease activity index, colon length and weight, and histopathology.

FIG. 7B shows characteristics of the experimental and control groups used in the study described in FIG. 7A.

Figure 8A:
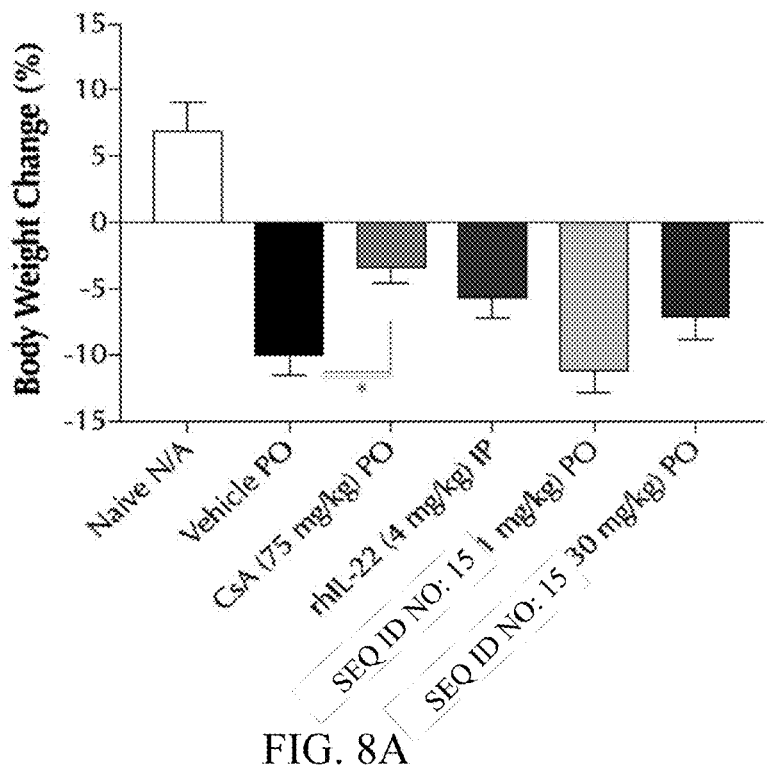
FIG. 8A shows the percent (%) change in body weight of animals at study day 10 relative to day 0 of the various experimental and control groups. Baseline (day 0 vs. 10) body weight change by rhIL-22 with SEQ ID NO: 12 or the delivery construct with SEQ ID NO: 15 relative to vehicle was not significant as assessed by 1-way ANOVA. Positive model control (cyclosporine) CsA was significantly different relative to Vehicle as assessed by a 1-way ANOVA.

FIG. 8A shows the percent (%) change in body weight of animals at study day 10 relative to day 0 of the various experimental and control groups. Baseline (day 0 vs. 10) body weight change by rhIL-22 with SEQ ID NO: 12 or the delivery construct with SEQ ID NO: 15 relative to vehicle was not significant as assessed by 1-way ANOVA. Positive model control (cyclosporine) CsA was significantly different relative to Vehicle as assessed by a 1-way ANOVA.

Figure 8B:
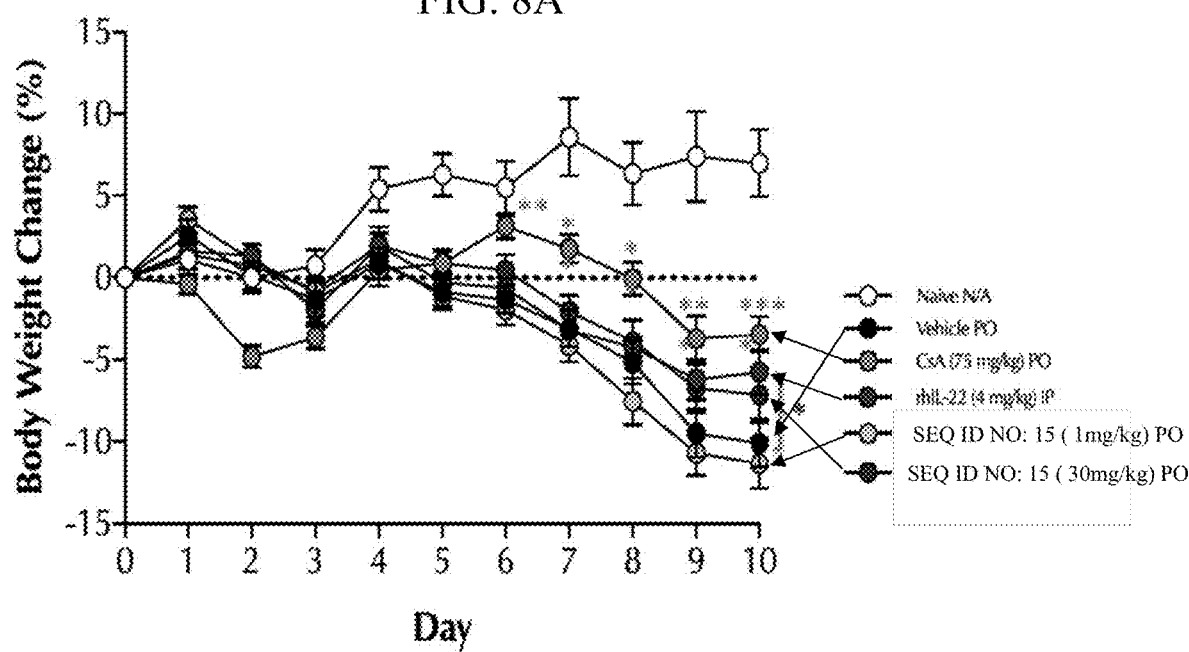
FIG. 8B shows the change in body weight of experimental and control animals over the first 10 study days. CsA group mean body weight over the study period was significantly improved relative to vehicle control day 6 through day 10 as assessed by 2-way ANOVA(*, , *) rhIL-22 (i.p.) body weight was significantly improved relative to vehicle control at day 10 as assessed by 2-way ANOVA (*), $*p<0.05$, $p<0.01$, $*p<0.001$.

FIG. 8B shows the change in body weight of experimental and control animals over the first 10 study days. CsA group mean body weight over the study period was significantly improved relative to vehicle control day 6 through day 10 as assessed by 2-way ANOVA(*, , *) rhIL-22 (i.p.) body weight was significantly improved relative to vehicle control at day 10 as assessed by 2-way ANOVA (*), $*p<0.05$, $p<0.01$, $*p<0.001$.

Figure 9:
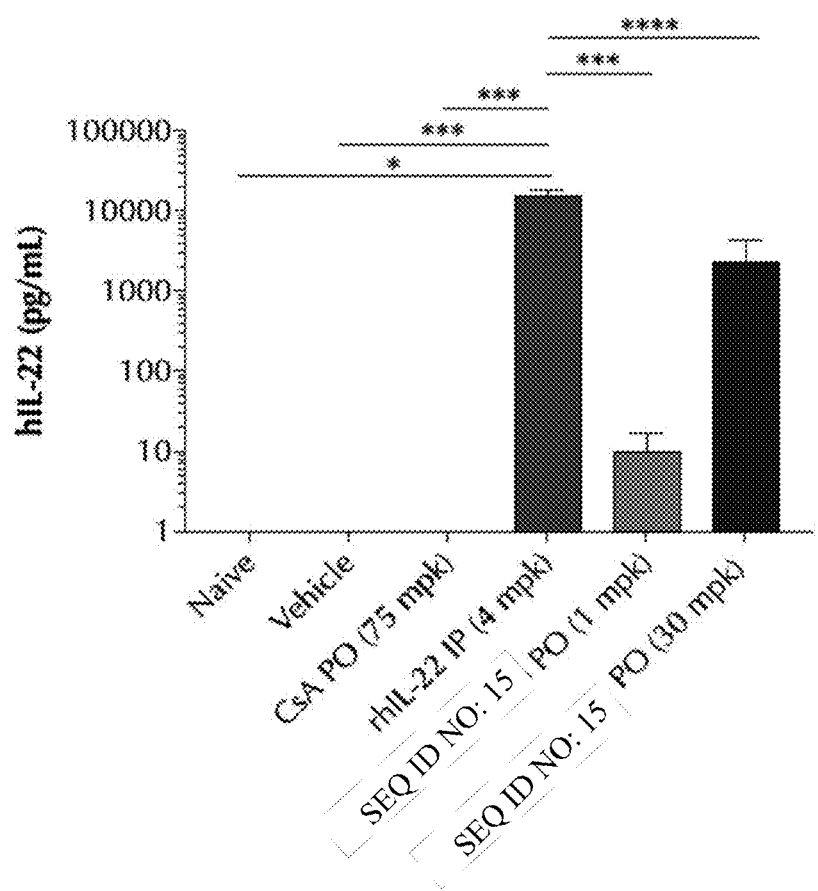
FIG. 9 shows results of plasma ELISA experiments to determine IL-22 plasma levels. The results show that plasma rhIL-22 concentrations trended towards increased levels in plasma after oral gavage of both 1 and 30 mg/kg doses of the delivery construct with SEQ ID NO: 15 in a dose-dependent manner ($*p<0.05$, $p<0.01$, $*p<0.001$. $****p<0.0001$; Mean±SEM; n=2 Naïve, 5 Vehicle, 5 CsA, 10 others)

FIG. 9 shows results of plasma ELISA experiments to determine IL-22 plasma levels. The results show that plasma rhIL-22 concentrations trended towards increased levels in plasma after oral gavage of both 1 and 30 mg/kg doses of the delivery construct with SEQ ID NO: 15 in a dose-dependent manner ($*p<0.05$, $p<0.01$, $*p<0.001$. $****p<0.0001$; Mean±SEM; n=2 Naïve, 5 Vehicle, 5 CsA, 10 others).

These data show that the delivery construct with SEQ ID NO: 15 induced a dose-dependent trend towards body weight improvement after administration via oral gavage. IL-22 was measured in increased levels in plasma after oral gavage of both 1 and 30 mg/kg doses of the delivery construct with SEQ ID NO: 15 in a dose-dependent manner. These data suggest that orally administered delivery construct with SEQ ID NO: 15 is capable of reducing symptoms of colitis in a DSS mouse model comparable to i.p. administered rhIL-22.

In addition, biomarkers for the orally administrable delivery construct with SEQ ID NO: 15 were evaluated by administering rhIL-22 to CD-1 mice as described below.

Figure 10A:
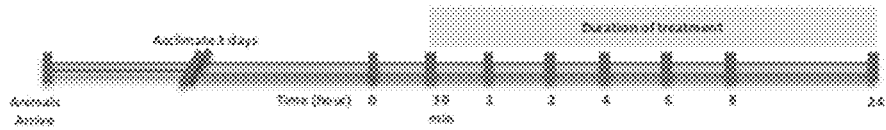
FIG. 10A shows an overview of a single dose in vivo study designed to identify biomarker(s) of target engagement after single (acute dosing) of rhIL-22 in healthy CD-1 mice.

FIG. 10A shows an overview of a single dose in vivo study designed to identify biomarker(s) of target engagement after single (acute dosing) of rhIL-22 in healthy CD-1 mice.

Figure 10B:
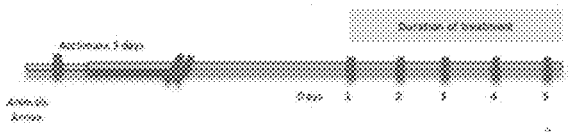
FIG. 10B shows an overview of a multiple dose (sub-chronic dosing) in vivo study designed to identify biomarker (s) of target engagement after single and multiple doses of rhIL-22 in healthy CD-1 mice.
Figure 10B:
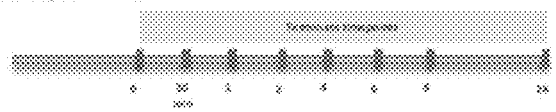

FIG. 10B shows an overview of a multiple dose (sub-chronic dosing) in vivo study designed to identify biomarker(s) of target engagement after single and multiple doses of rhIL-22 in healthy CD-1 mice.

Figures 11A, 11B:
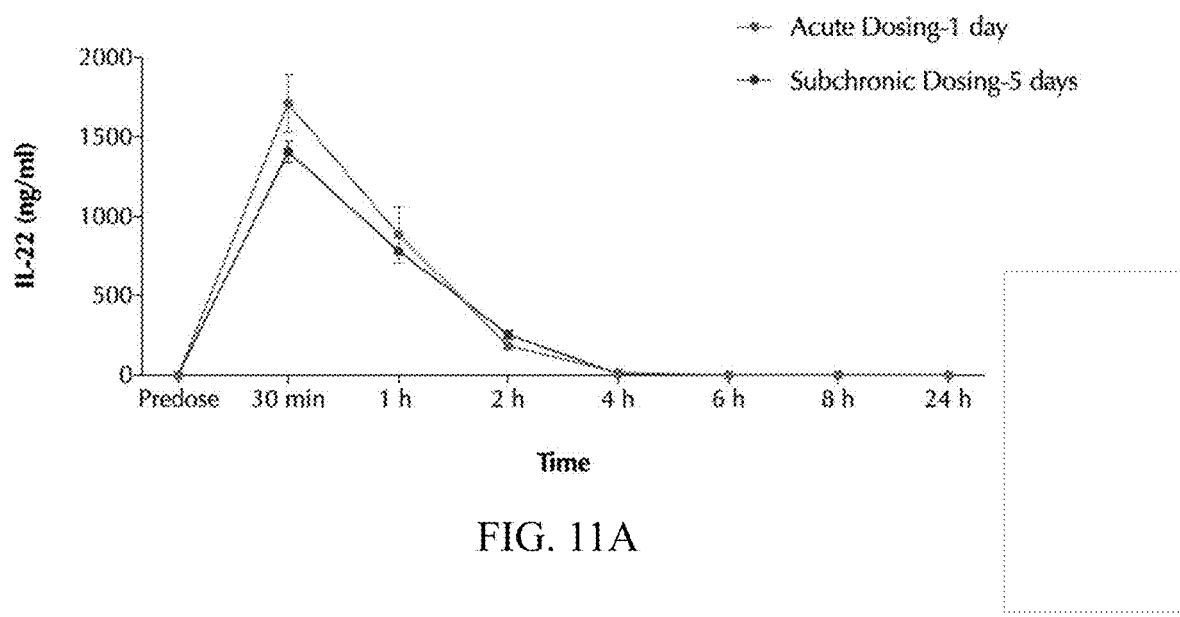
FIG. 11A shows that acute and sub-chronic administration of rhIL-22 increases IL-22 concentration consistently.
FIG. 11B shows some pharmacokinetic parameters measured during the acute and sub-chronic dosing experiments described in FIG. 11A.

FIG. 11A shows that acute and sub-chronic administration of rhIL-22 increases IL-22 concentration consistently.

FIG. 11B shows some pharmacokinetic parameters measured during the acute and sub-chronic dosing experiments described in FIG. 11A.

Figure 12A:
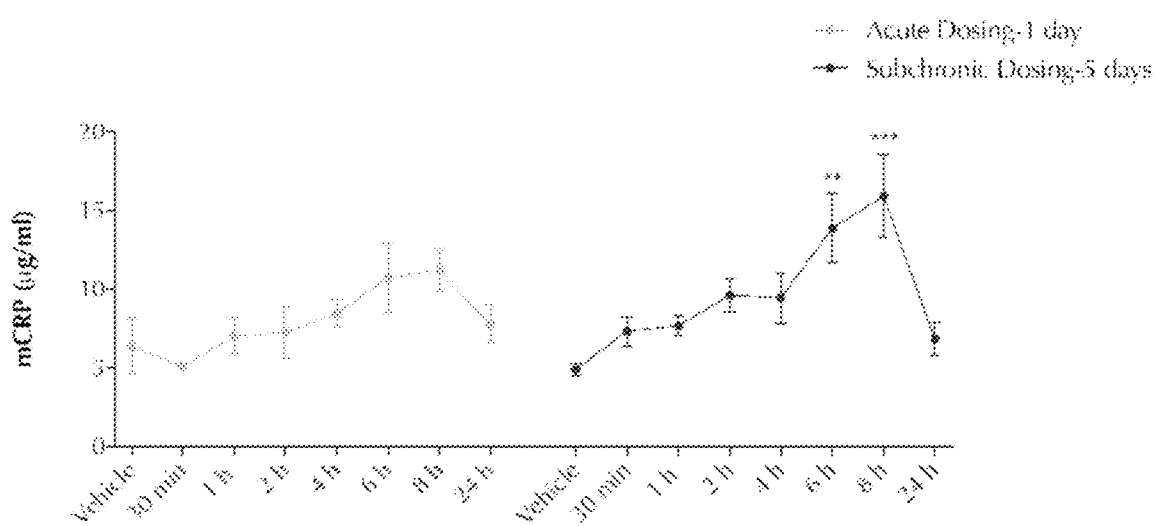
FIG. 12A shows the induced circulating murine C-reactive protein (mCRP) concentration in response to 1 day after acute dosing of rhIL-22 (SEQ ID NO: 12) and after 5 days of sub-chronic dosing of rhIL-22 (SEQ ID NO: 12). The results show a time-dependent increase in circulating mCRP in both study groups.

FIG. 12A shows the induced circulating murine C-reactive protein (mCRP) concentration in response to 1 day after acute dosing of rhIL-22 (SEQ ID NO: 12) and after 5 days of sub-chronic dosing of rhIL-22 (SEQ ID NO: 12). The results show a time-dependent increase in circulating mCRP in both study groups.

Figures 12B, 12C:
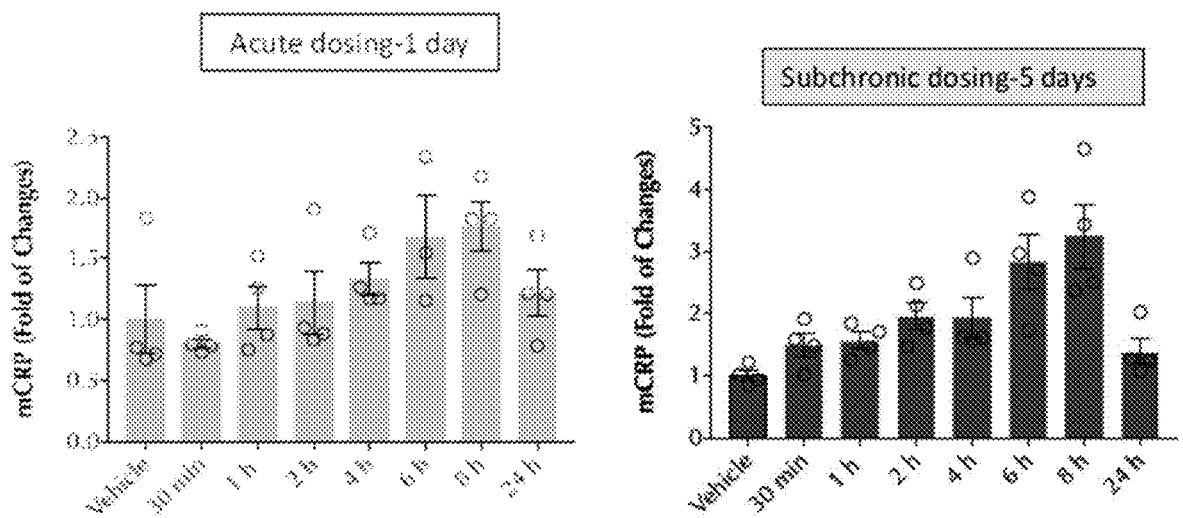
FIG. 12B shows fold change of plasma mCRP concentration 1 day after acute dosing of rhIL-22 (SEQ ID NO: 12).
FIG. 12C shows fold change of plasma mCRP concentration after 5 days of sub-chronic dosing of rhIL-22 (SEQ ID NO: 12).

FIG. 12B shows fold change of plasma mCRP concentration 1 day after acute dosing of rhIL-22 (SEQ ID NO: 12).

FIG. 12C shows fold change of plasma mCRP concentration after 5 days of sub-chronic dosing of rhIL-22 (SEQ ID NO: 12).

Figure 13A:
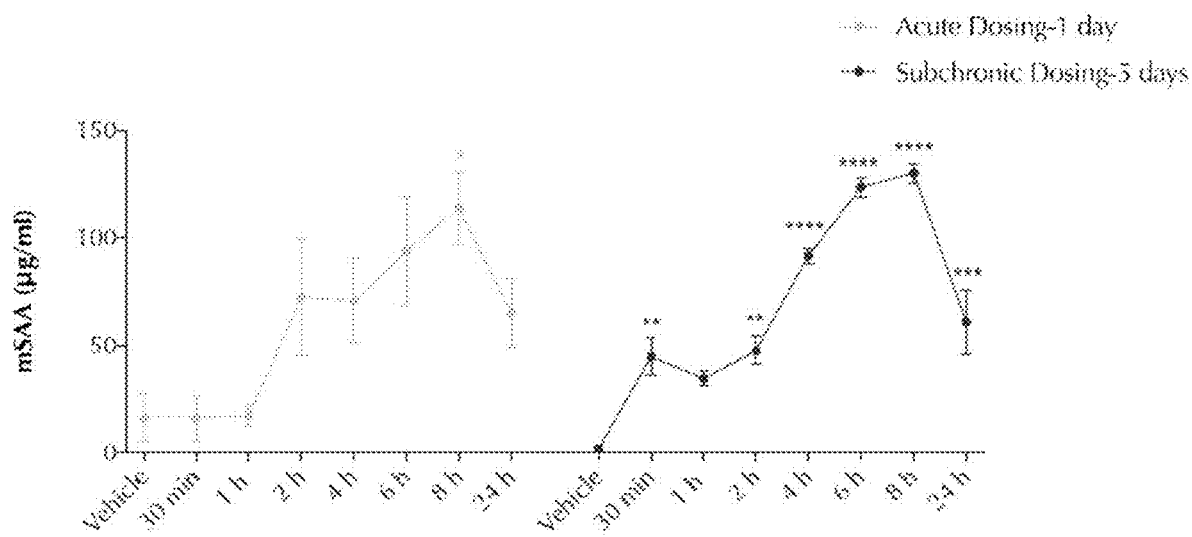
FIG. 13A shows the induced circulating murine serum amyloid protein A (mSAA) concentration in response to 1 day after acute dosing of rhIL-22 (SEQ ID NO: 12) and after 5 days of sub-chronic dosing of rhIL-22 (SEQ ID NO: 12). The results show a time-dependent increase in circulating mSAA in both study groups, with approximate plasma peak concentrations about 8 hours after administration
Figure 13B:
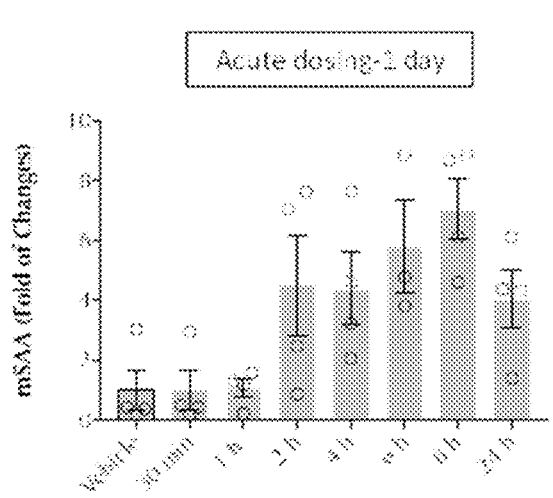
FIG. 13B shows fold change of plasma mSAA concentration 1 day after acute dosing of rhIL-22 (SEQ ID NO: 12).

FIG. 13A shows the induced circulating murine serum amyloid protein A (mSAA) concentration in response to 1 day after acute dosing of rhIL-22 (SEQ ID NO: 12) and after 5 days of sub-chronic dosing of rhIL-22 (SEQ ID NO: 12). The results show a time-dependent increase in circulating mSAA in both study groups, with approximate plasma peak concentrations about 8 hours after administration FIG. 13B shows fold change of plasma mSAA concentration 1 day after acute dosing of rhIL-22 (SEQ ID NO: 12).

Figure 13C:
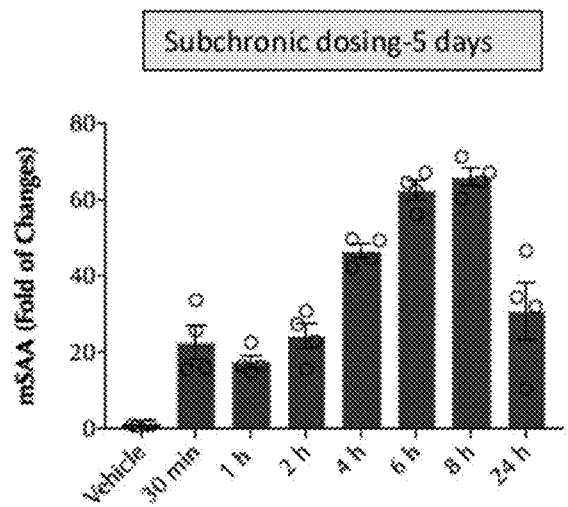
FIG. 13C shows fold change of plasma mSAA concentration after 5 days of sub-chronic dosing of rhIL-22 (SEQ ID NO: 12).

FIG. 13C shows fold change of plasma mSAA concentration after 5 days of sub-chronic dosing of rhIL-22 (SEQ ID NO: 12).

Figure 14A:
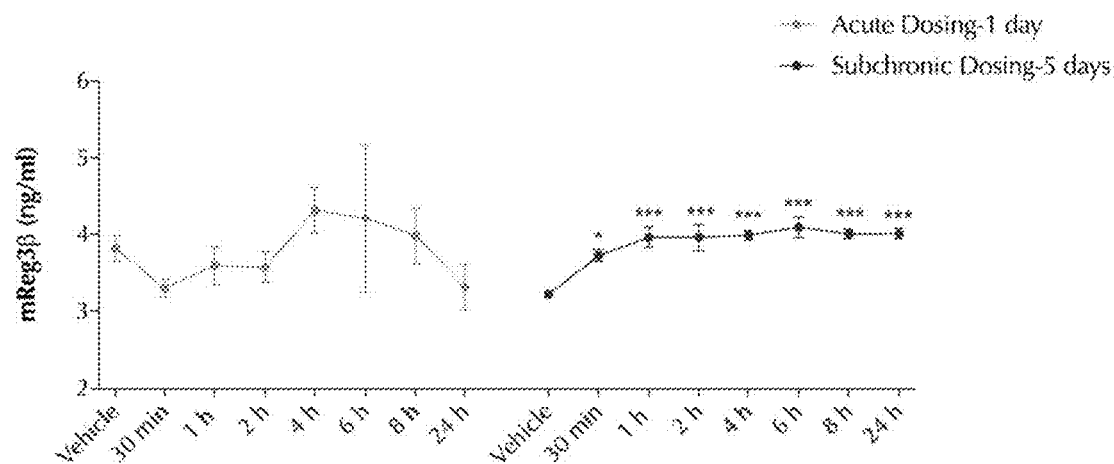
FIG. 14A shows the induced circulating regenerating islet-derived protein 3β (Reg3β) in response to 1 day after acute dosing of rhIL-22 (SEQ ID NO: 12) and after 5 days of sub-chronic dosing rhIL-22 (SEQ ID NO: 12).

FIG. 14A shows the induced circulating regenerating islet-derived protein 3β (Reg3β) in response to 1 day after acute dosing of rhIL-22 (SEQ ID NO: 12) and after 5 days of sub-chronic dosing rhIL-22 (SEQ ID NO: 12).

Figures 14B, 14C:
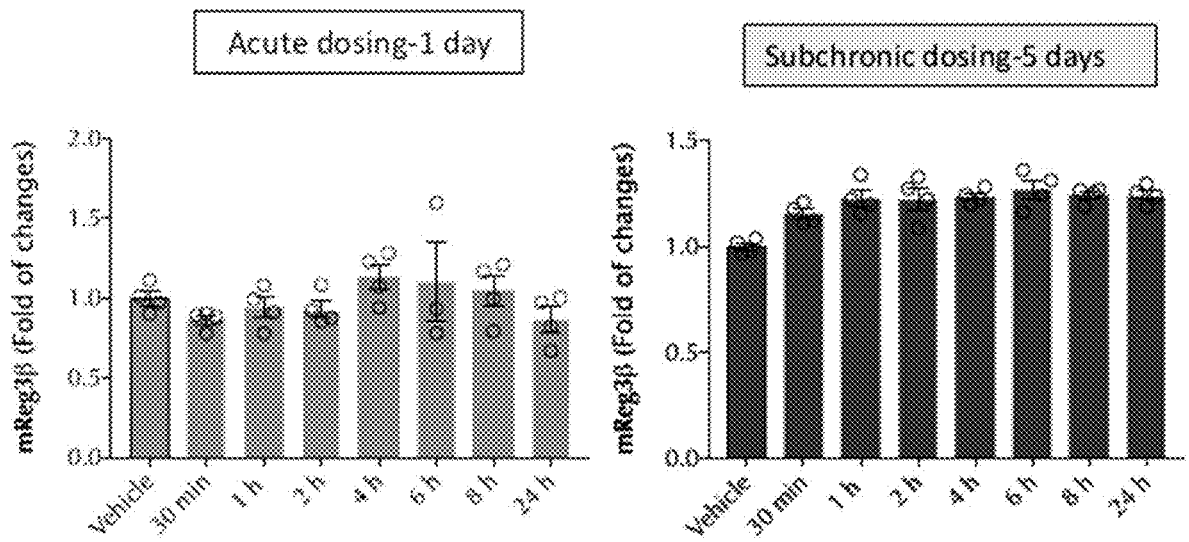
FIG. 14B shows fold change of plasma Reg3β concentration 1 day after acute dosing of rhIL-22 (SEQ ID NO: 12).
FIG. 14C shows fold change of plasma Reg3β concentration after 5 days of sub-chronic dosing of rhIL-22 (SEQ ID NO: 12).
Figure 15:
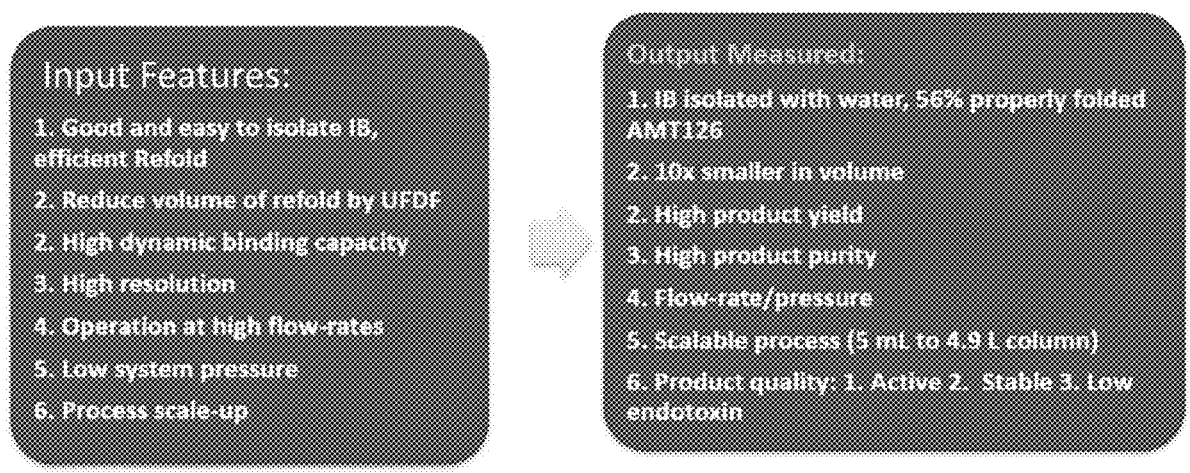
FIG. 15 illustrates a flow chart showing how improved manufacturability may enable clinical translation.

FIG. 14B shows fold change of plasma Reg3β concentration 1 day after acute dosing of rhIL-22 (SEQ ID NO: 12).

FIG. 14C shows fold change of plasma Reg3β concentration after 5 days of sub-chronic dosing of rhIL-22 (SEQ ID NO: 12).

These results demonstrate that three potential IL-22 PD biomarkers of target engagement: C reactive protein (CRP), serum amyloid protein A (SAA), and regenerating islet-derived protein 3β (Reg3β) that may be used in studies evaluating the pharmacodynamics (PD) of delivery constructs such as those with SEQ ID NOs: 15 or 17.

Example 6

Protein Solubilization 627 g of double-washed inclusion bodies (DWIB) from SEQ ID NO: 15 fermentation were resuspended in 4500 mL of 8M Guanidine/HCl (Gu-HCl), and 50 mM Tris pH at 8.0. Subsequently, 50 mM Tris pH 8.5 was added to complete the volume to 6.0 L. The solution was stirred gently on a stir-plate and 9.225 g of the reducing agent dithiothreitol (DTT) was added. The final solubilized protein (SEQ ID NO: 15) solution of 6 L consisted of 6M Gu-HCl, 50 mM Tris pH 8.0, 10 mM DTT, and ~1 g DWIB/10 mL buffer. The solubilized protein (SEQ ID NO: 15) solution was incubated at room temperature (RT) while stirred on a magnetic stir-plate, and then centrifuged at 15,970×g for 90 minutes at 4° C. The supernatant comprising the solubilized protein was carefully transferred to a new vessel with a total volume of 5520 mL. The protein concentration determination was performed by Bradford assay and was determined at 15 mg/mL.

The data demonstrate that protein solubilization can be performed using the above procedure.

Example 7

Protein Refolding

This example demonstrates protein refolding as part of the purification process as described in the flow chart of FIG. 17.

A refolding solution was carefully researched, developed and optimized (FIG. 18). The optimization process utilized a design of experiments (DOE) of 15 different matrices, 12 variables and 200 refold reactions. Decisions were made by a process of elimination. The initial refold mixture (containing the initial refold solution and the refolded solubilized protein (SEQ ID NO: 15)) is presented in TABLE 2. An optimized refold mixture (containing the optimized refold solution and the refolded solubilized protein (SEQ ID NO: 15)) is presented in TABLE 3.

TABLE 2

Initial refold mixture 100 mM Tris pH 8.5 (@ 4° C.)
0.5M arginine
1M urea
2 mM EDTA
0.3 mM GSH
1 mM GSSG
0.2 mg/mL refold concentration

TABLE 3

Optimized refold mixture 100 mM Tris pH 8.5 (@ 4° C.)
1.0M arginine
10% glycerol
3 mM L-cysteine
1 mM cystamine-2HCl
>0.1 mg/mL refold concentration The 105 L refold solution was incubated at 4° C. for 16 hours and then filtered through a flow filter (AkroPac® by Pall corporation or Sartopore 2XLG by Sartorius) using a 0.8/0.2 um membrane and Cole-Parmer® peristaltic pump and tubing.

The solubilized protein (SEQ ID NO: 15) (105 g) from EXAMPLE 6 was added to 100 L of an optimized refold solution prechilled to 4° C.

This process was programmed to one hour using a ColeParmer® peristaltic pump set at 73 ml/min. This process took place in a cold room at 4° C.

Figure 19:
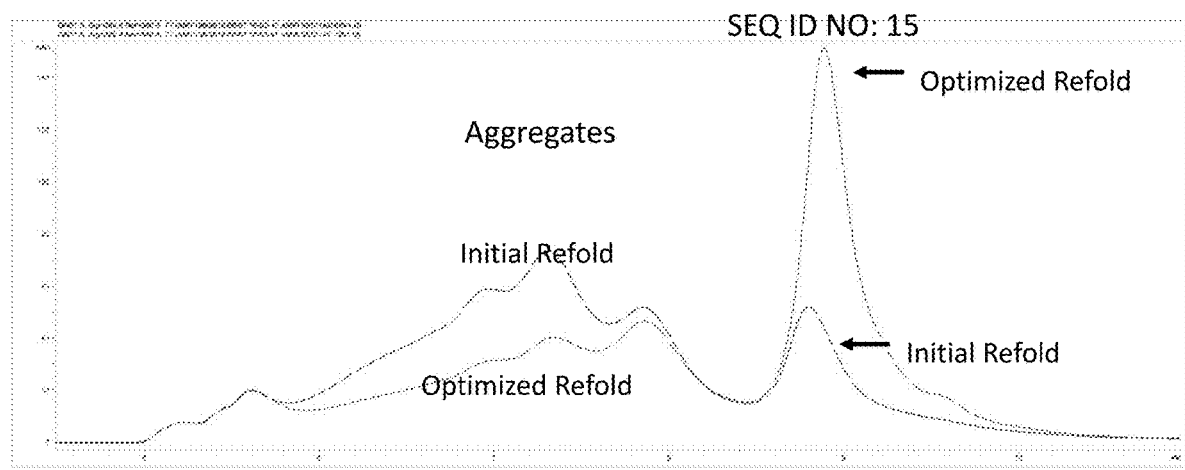
FIG. 19 is a size-exclusion chromatograph (SEC) showing the signal of the optimized refolded protein (SEQ ID NO: 15) and protein aggregates having higher molecular masses and thus lower retention times.
Figure 20:
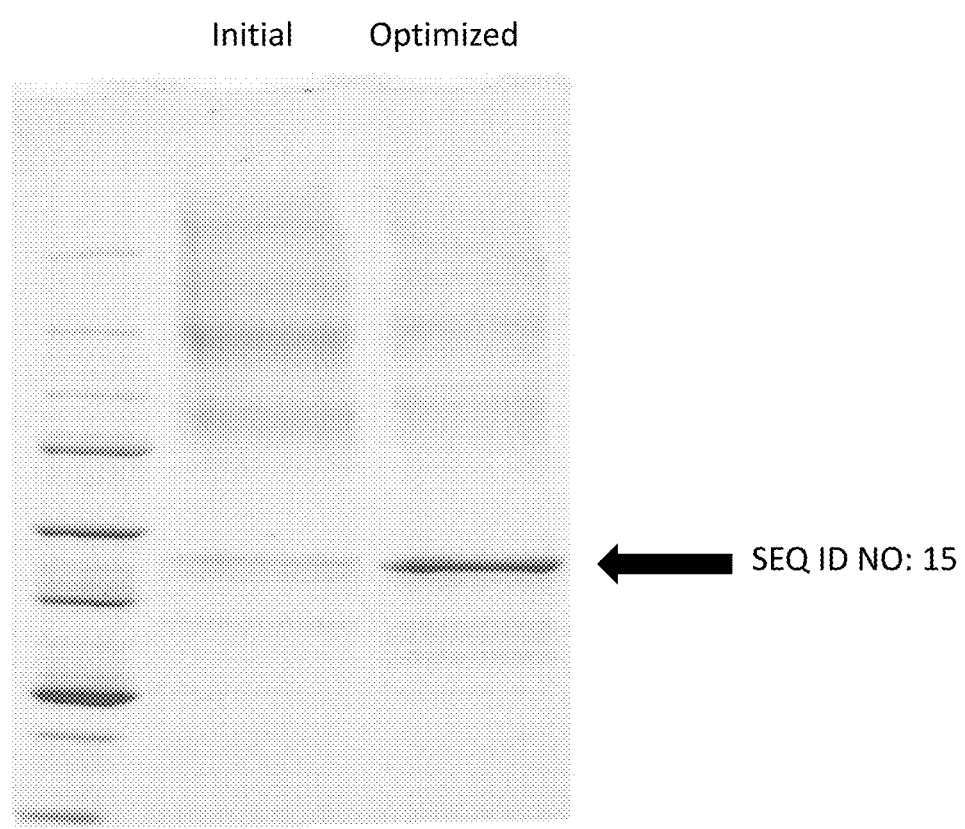
FIG. 20 illustrates an exemplary SDS-PAGE of the initial and optimized refolded protein (SEQ ID NO: 15).

The optimized refold buffer solution produced a larger amount of the SEQ ID NO: 15 relative to aggregates of SEQ ID NO: 15 (FIGS. 19-20). Use of the initial refold solution produced about 10%-15% correctly refolded SEQ ID NO:15. Use of the optimized refold solution produced about 45%-55% correctly refolded SEQ ID NO: 15.

Example 8

Protein Concentration and Buffer Exchange by TFF UF/DF

This example demonstrates protein concentration and buffer exchange using tangential flow filtration (TFF) based on ultrafiltration/diafiltration (UF/DF) principles.

Refolded protein (e.g., of SEQ ID NO: 15) was processed by TFF system (Millipore) to concentrate it 10-fold and buffer exchange 5-fold. The process was performed by ultrafiltration/diafiltration (UF/DF) using four 10 kDa MWCO Millipore Ultracell Pellican3, 1.14 m² TFF flat sheet cassettes. The diafiltration buffer consisted of 20 mM Tris-base pH 7.5 and 100 mM NaCl. The final volume at the end of the UF/DF process was 10 L. This material was subsequently filtered using a flow filtration system employing AkroPac® 0.8/0.2 um filter by Pall corporation and ColeParmer® peristaltic pump and tubing. Bradford assay was performed to determine the protein concentration, yield, and step recovery. At this point, a quantitative SEC-HPLC was performed to determine the amount of the properly folded protein with SEQ ID NO: 15 present in the refold and UF/DF samples. A commercially available BSA of a known concentration was used as a reference standard from which the standard curve was generated for the Bradford assay. The Agilent 1100 HPLC system and the TSKgel SuperSW3000, 4 µm, 4.6 mm ID×30.0 cm L (Tosoh Bioscience, 18675) column were used. Based on this quantitative assay, the refold efficiency was determined.

The data show that protein refolding can be performed using buffer exchange and TFF UF/DF.

Example 9

Protein Chromatography Using the Capture Step NH₂-750F® Resin

This example demonstrates capture steps in protein anion exchange chromatography using the NH₂-750F® resin.

The AKTA Avant 150 or AKTA Pilot FPLC systems from General Electric (GE) were used for protein chromatography. The Tosoh anion exchange resin NH₂-750F® was used to pack a column with a minimum bed-height of at least 20 cm and ensuring a column volume that would facilitate a dynamic binding capacity of 20-25 g/L. A buffer of 20 mM sodium acetate, pH 4.5 or 20 mM sodium citrate, pH 4.5 were used to pack the column. The buffers used were as follow: buffer A: 20 mM Tris pH 7.5, 0.5 M NaCl; buffer B: 20 mM Tris pH 7.5, 2.0 M NaCl. The NH₂-750F column was then cleaned with 0.5 M NaOH solution with a contact time of 30 minutes, and then equilibrated with buffer A for at least 3 column volumes (CV), or until pH and conductivity reach stable lines at the expected values (pH 7.5-pH 7.7, ~49 mS/cm+/−1 mS/cm).

Prior to loading onto the column, the UF/DF protein (SEQ ID NO: 15) solution was supplemented with 0.4 M NaCl by adding a 5 M stock solution and the conductivity was measured to ensure conductivity of 49 mS/cm+/−2 mS/cm. The protein (SEQ ID NO: 15) solution was loaded onto the column with a flow-rate of a minimum of 5 minutes column residence time, and the flow-through was collected. The column was washed with 3 CV of buffer A or until the absorbance at 280 nm returned, and was stable at baseline, near 0.0 mAU at 280 nm. At this point a linear gradient of 20 CV from 0.0-62.5% B, followed by a step gradient to 100% B for additional 5 CV was performed. Fractions were collected throughout and their volumes were no greater than 0.5 of the column volume. Samples from different fractions were analyzed by SDS-PAGE using the Bio-Rad Chemi-Doc™ MP imaging system, and the fractions containing over 90% of SEQ ID NO: 15 were pooled and designated as NH₂-750F-pool. The protein concentration of the NH₂-750F-pool was measured using Thermo Fisher Nanodrop One™, by reading the absorbance at 280 nm (A280) considering extinction coefficient of 1.22 for SEQ ID NO: 15 and a 260/280 nm ratio <0.6. The NH₂-750F-pool contains approximately 1.0 M NaCl.

Figure 21A:
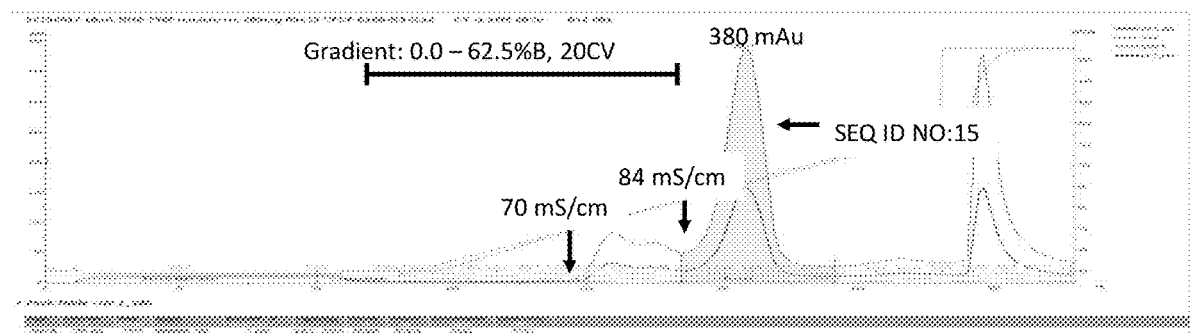
FIGS. 21A-21B illustrates a size-exclusion chromatograph following a first column purification of SEQ ID NO: 15 using anion exchange resin $NH_2$-750F.
Figure 21B:
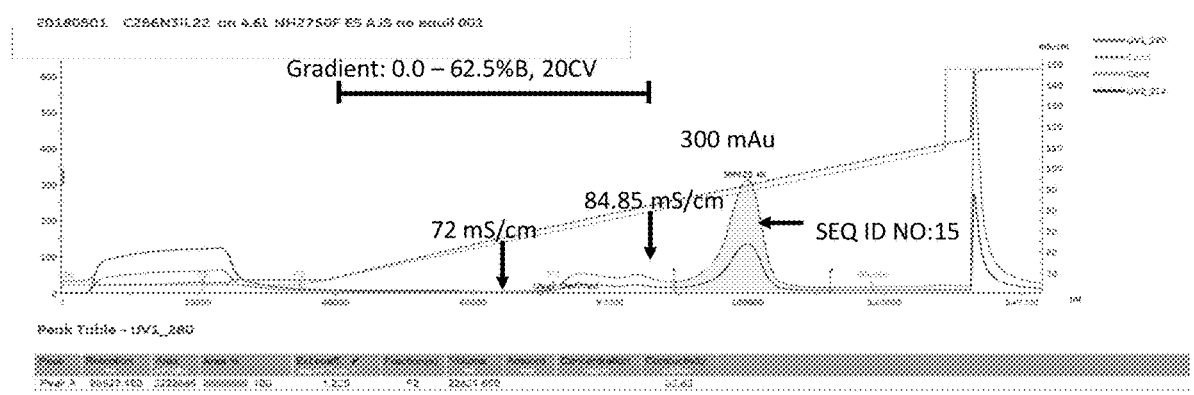

An example chromatogram following NH₂-750F purification of SEQ ID NO: 15 is shown in FIG. 21A for a bed height of 20 cm and a column volume of 10 mL and FIG. 21B for a bed height of 30 cm and a column volume of 4.6 L.

A summary of the NH₂-750F purification is show in TABLE 4 for SEQ ID NO: 15 and TABLE 5 for SEQ ID NO: 14, which was generally produced, refolded, and purified in a manner analogous to SEQ ID NO: 15.

TABLE 4

Summary of SEQ ID NO: 15 NH₂-750F purification
SEQ ID NO: 15

| | |
|---|---|
| Buffer A | 20 mM Tris pH 7.5, 0.5M NaCl |
| Buffer B | 20 mM Tris pH 7.5, 2.0M NaCl |

TABLE 4-continued

Summary of SEQ ID NO: 15 NH$_2$-750F purification
SEQ ID NO: 15

| | |
|---|---|
| Bed Height | Minimum 20 cm |
| Residence Time | 5.0 minutes |
| Gradient | 0.0-62.5% B, 20 CV |
| Binding capacity | 20-25 g/L (Breakthrough at 40 g/L) |
| Purity | 93-96% |
| Recovery | 71-76% |
| Endotoxin | <1.0 EU/mg |

TABLE 5

Summary of SEQ ID NO: 14 NH$_2$-750F purification
SEQ. ID NO: 14

| | |
|---|---|
| Buffer A | 20 mM Tris pH 7.5, 0.7M NaCl, 10% glycerol |
| Buffer B | 20 mM Tris pH 7.5, 2.0M NaCl, 10% glycerol |
| Bed Height | Minimum 20 cm |
| Residence Time | 5.0 minutes |
| Gradient | 0.0-62.5% B, 20 CV |
| Binding capacity | 20-25 g/L |
| Purity | ≥93-96% |
| Recovery | 80-93% |
| Endotoxin | <1.0 EU/mg |

Example 10

Protein Chromatography Using the CaPure®
Procedure

This example demonstrates a polishing purification step in protein chromatography using the CaPure® procedure.

The AKTA Avant 150 or AKTA Pilot FPLC systems from General Electric (GE) were used for protein chromatography of proteins of SEQ ID NO: 15 and SEQ ID NO: 14. The Tosoh hydroxyapatite mixed-mode resin CaPure® was used to pack a column for each of SEQ ID NO: 15 and SEQ ID NO: 14 with a minimum bed-height of at least 10 cm and ensuring a column volume that would facilitate a dynamic binding capacity of maximum 20 g/L. The buffers used were as follows for SEQ ID NO: 15: buffer A: 20 mM Tris pH 7.5, 100 mM NaCl, and 1 mM CaCl$_2$; buffer B: 200 mM sodium phosphate pH 7.0, 100 mM NaCl, and 1 mM CaCl$_2$. The buffers used were as follows for SEQ ID NO: 14: buffer A: 20 mM Tris pH 7.5, 100 mM NaCl, and 1 mM CaCl$_2$; buffer B: 200 mM sodium phosphate pH 7.0, 100 mM NaCl, and 1 mM CaCl$_2$. Each CaPure® column was then cleaned with 0.5 M of NaOH with contact time of 30 minutes or more, and then equilibrated with buffer A for at least 3 column volumes (CV), or until pH and conductivity reach stable lines at the expected values (pH 7.5-pH 7.7, ~11 mS/cm+/−1 mS/cm). There was no need to treat the NH$_2$-750F-pool prior to loading it onto the column. This significantly reduced protein loss, time, and resources. The NH$_2$-750F pool was loaded onto the column with a flow-rate of a minimum of 5 minutes column residence time, and the flow-through was collected. The column was washed with 3 CV of buffer A or until the absorbance at 280 nm returned, and was stable at baseline, near 0.0 mAu. At this point, a linear gradient of 25 CV from 0-25% B, followed by a step gradient to 100% B for additional 5 CV was performed. Fractions were collected throughout and their volumes were ranging from 0.36 to 1.43 of the column volume, depending on the elution profile. Samples from different fractions were analyzed by SDS-PAGE using the ChemiDoc™ MP imaging system, and the fractions containing over 95% of SEQ ID NO: 15 or SEQ ID NO: 14 were pooled and designated as CaPure-pool. The protein concentration of the CaPure-pool was measured using Thermo Fisher Nanodrop One™, by reading the absorbance at 280 nm (A280) considering extinction coefficient of 1.22 for SEQ ID NO: 15 and a 260/280 nm ratio <0.6.

Figure 22A:
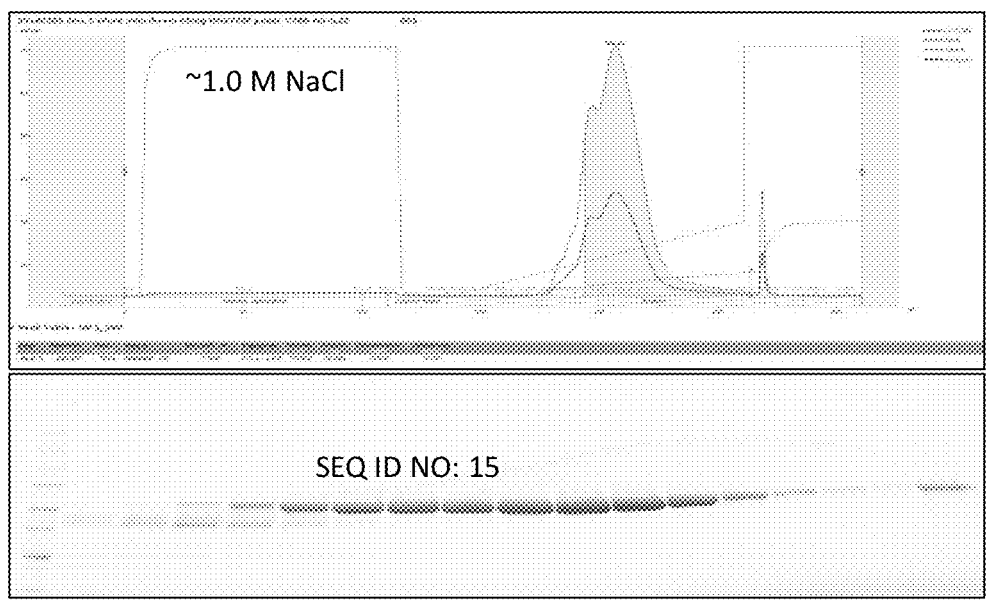
FIGS. 22A-22B illustrate a size exclusion chromatograph following a second column purification of SEQ ID NO: 15 using hydroxyapatite resin CaPure®.
Figure 22B:
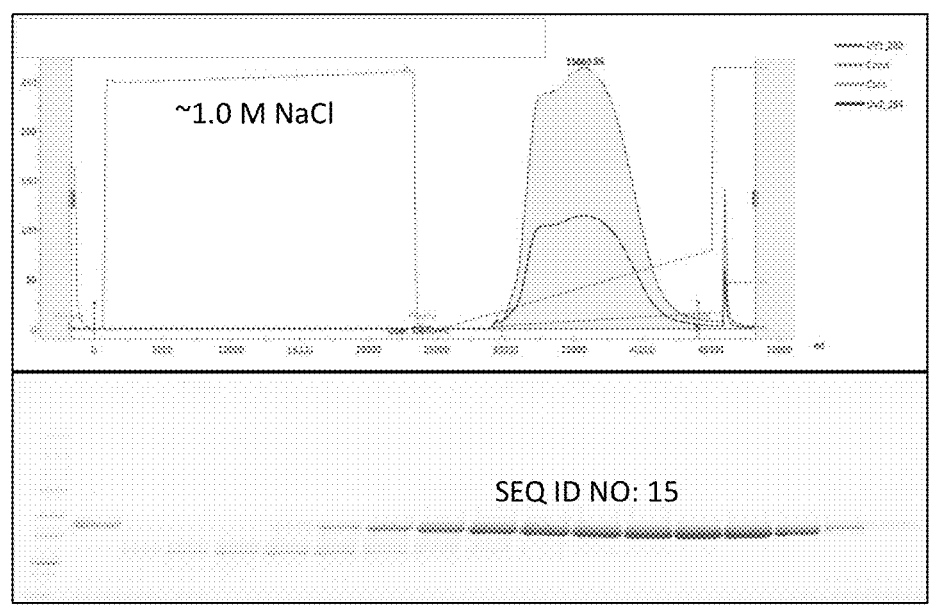

An exemplary chromatogram following CaPure® purification of SEQ ID NO: 15 is shown in FIG. 22A for a bed height of 10 cm and column volume of 5 mL and FIG. 22B for a bed height of 21 cm and column volume of 800 mL.

A summary of the CaPure® purification is show in TABLE 6 for SEQ ID NO: 15 and TABLE 7 for SEQ ID NO: 14.

TABLE 6

Summary of SEQ ID NO: 15 CaPure ® purification
SEQ ID NO: 15

| | |
|---|---|
| Buffer A | 20 mM Tris pH 7.5, 100 mM NaCl, 1 mM CaCl$_2$ |
| Buffer B | 200 mM sodium phosphate pH 7.0, 100 mM NaCl, 1 mM CaCl$_2$ |
| Bed Height | 20 cm |
| Residence Time | 5.0 minutes |
| Gradient | 0.0-25% B, 25 CV |
| Binding capacity | 20 g/L |
| Purity | >98% |
| Recovery | >92% |
| Endotoxin | <1.0 EU/mg |

TABLE 7

Summary of SEQ ID NO: 14 CaPure ® purification
SEQ ID NO: 14

| | |
|---|---|
| Buffer A | 20 mM Tris pH 7.5, 100 mM NaCl, 1 mM CaCl$_2$ |
| Buffer B | 200 mM sodium phosphate pH 7.0, 100 mM NaCl, 1 mM CaCl$_2$ |
| Bed Height | 20 cm |
| Residence Time | 5.0 minutes |
| Gradient | 0.0-25% B, 25 CV |
| Binding capacity | 20 g/L |
| Purity | >98% |
| Recovery | >92% |
| Endotoxin | <1.0 EU/mg |

Example 11

Protein Concentration by TFF UF/DF

This example demonstrates protein formulation by TFF UF/DF procedures.

The CaPure® pool was concentrated by a TFF system (Pall corporation) to a final concentration of 20 mg/mL followed by 5-fold buffer exchange. The process was performed by ultrafiltration/diafiltration (UF/DF) using three 10 kDa MWCO Millipore Pellican3, 0.114 m$^2$ TFF flat sheet cassettes. The diafiltration buffer consisted of 10 mM sodium phosphate pH7.0, 100 mM NaCl. The formulated SEQ ID NO: 15 was subsequently filtered using a flow filtration system employing AkroPac® 0.8/0.2 um filter by Pall corporation and Cole-Parmer® peristaltic pump and tubing. The formulated SEQ ID NO: 15 was then stored in aliquots at −80° C. and the following analyses were performed to ensure its biophysical quality: (1) Protein (e.g., SEQ ID NO: 15) concentration at 20 mg/mL by measuring the absorbance at 280 nm with 260/280 ratio <0.6 using Thermo Fisher Nanodrop One™ and considering protein extinction coefficient of 1.22; (2) LAL endotoxin levels below 1.0 Eu/mg measured by Charles River Laboratories equipment; (3) Purity by SEC-HPLC above 97% purity (typically >98%) using TSKgel GW3000SWXL, 5 µm, 7.8 mm ID×30.0 cm L column (Tosoh Bioscience, 8541) (4) SDS-PAGE analysis using the Bio-Rad gel apparatus and its associated ChemiDoc™ MP imaging system.

Example 12

Evaluation of In Vivo Activity of Purified Fusion Molecules

This example demonstrates methods for verifying the proper folding of the fusion molecules with regard to their ability to carry a biologically active cargo across an intact epithelium.

The fusion protein with SEQ ID NO: 15 is expressed by *E. coli* and collected from inclusion bodies and folded using a shuffle exchange buffer system as described in EXAMPLE 8 above. The resulting material is purified according to the methods described in EXAMPLE 9 and EXAMPLE 10, and as summarized for example in TABLES 4-7, depending on the molecular characteristics of the fusion molecule. The preparation has a protein purity of ~98% based upon SDS PAGE. Epithelial cells are treated with the fusion molecule having SEQ ID NO: 15 at concentrations of 25 nM and 250 nM. Compared to untreated matched cells, SEQ ID NO: 15 treated cells produce a dose-dependent decrease in cell number as assessed by flow cytometry of live/dead cells). Values represent n=4±standard deviation.

Example 13

Scale-Up of Fusion Protein Purification

This example demonstrates a scale-up of a purification method using the fusion protein of SEQ ID NO: 15 (FIGS. 7A and 7B).

The fusion protein with SEQ ID NO: 15 was purified on two different scales.

The first purification was carried out using a chromatography column with a volume of 10 mL packed with NH$_2$-750F® resin and the following parameters: Bed height: 20 cm, Residence time: 5 min (flow rate: 2 mL/min), buffer A: 20 mM Tris pH 7.5, 0.5 M NaCl, buffer B: 20 mM Tris pH 7.5, 2 M NaCl, and using the following gradient: 0.0-62.5% B for 20 column volumes (CVs). The fusion protein with SEQ ID NO: 15 was obtained with a purity of 93-96%, a recovery of >71%, and endotoxin levels <1.0 EU/mg.

The second purification was carried out using a chromatography column with a volume of 4.6 L packed with NH$_2$-750F® resin and the following parameters: Bed height: 30 cm, Residence time: 11.55 min (flow rate: 400 mL/min), buffer A: 20 mM Tris pH 7.5, 0.5 M NaCl, buffer B: 20 mM Tris pH 7.5, 2 M NaCl, and using the following gradient: 0.0-62.5% B for 20 column volumes (CVs). The fusion protein with SEQ ID NO: 15 was obtained with a purity of 93-96%, a recovery of >71%, and endotoxin levels <1.0 EU/mg.

Example 14

Consistency Between Process Step Recoveries

The purification process was carried out to purify the fusion protein of SEQ ID NO: 15 four times (lots 1-4), and the recovery of this fusion protein was assessed after each stage of the purification process (TABLE 8). There was a high degree of consistency in the recovery of the fusion protein between these replicates.

TABLE 8

Recovery of the fusion protein of SEQ ID NO: 15 in 4 replicate purification processes

| Process step | Process description | Lot 1 | Lot 2 | Lot 3 | Lot 4 | Average (%) |
|---|---|---|---|---|---|---|
| 2 | Refold UF/DF | 98.60% | 94% | 92.40% | 85% | 92 |
| 3 | NH$_2$-50F | 68.60% | 66.30% | 76% | 74.50% | 71.35% |
| 4 | CaPure | 99% | 96.40% | 100% | 94.80% | 97.55 |
| 5 | Formulation UF/DF | 97.80% | 100% | 98.75% | 100% | 99.14 |

These data demonstrate that the methods and compositions of the present disclosure allowed the production and purification of therapeutic fusion protein on a large scale, and that the herein disclosed methods and compositions provided high consistency during scale-up.

All of the methods disclosed and claimed herein may be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

Example 15

Comparison of SEQ ID NO: 15 and SEQ ID NO: 17

Figure 23A:
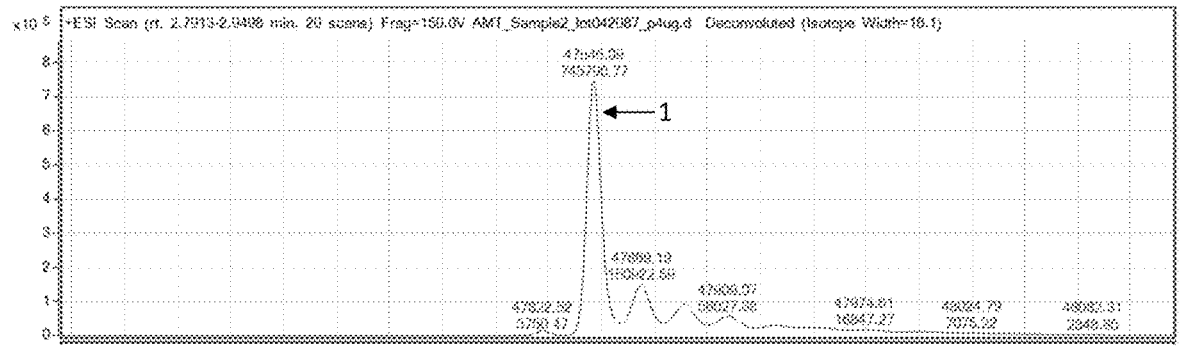
FIGS. 23A-23B illustrate a liquid chromatography-mass spectrophotometry (LC-MS) chromatograph following purification of heterologous fusion proteins.
Figure 23B:
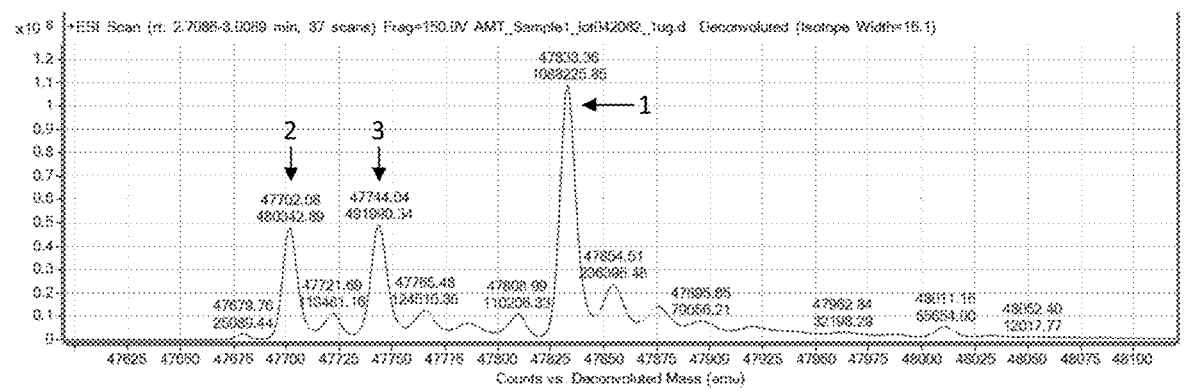

Liquid chromatography-mass spectrophotometry (LC-MS) was performed on purified compositions representing SEQ ID NO: 15 and SEQ ID NO: 17, and the results are represented in FIG. 23B and FIG. 23A, respectively. The composition of SEQ ID NO: 17 was produced, refolded, and purified in a manner analogous to that described above in connection with the composition of SEQ ID NO: 15.

Example 16

In Vivo Assessment of Delivery Constructs

This example describes an in vivo assessment of a delivery construct having the sequence of SEQ ID NO: 15 compared to the vehicle.

Figure 24:
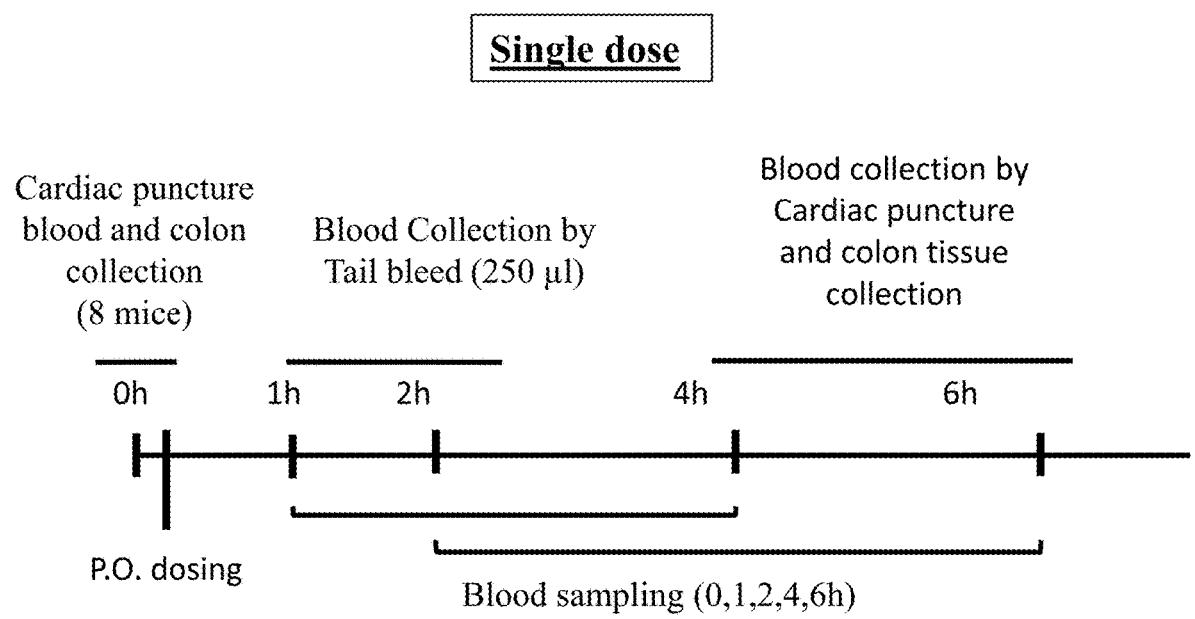
FIG. 24 illustrates the study overview of EXAMPLE 16 for assessing transport of the delivery construct having the sequence of SEQ ID NO: 15 across the gut epithelium and into circulation after oral (abbreviated herein as P.O.) delivery of the construct.

FIG. 24 shows a (single-dose) study overview for assessing transport of the delivery construct having the sequence of SEQ ID NO: 15 across the gut epithelium and into circulation after oral (abbreviated herein as P.O.) delivery of the construct. The animals used in these experiments were CD-1 male mice without fasting. A primary study endpoint was total plasma IL-22 exposure, and a secondary endpoint were plasma biomarkers, including IL-22 binding protein (e.g., IL-22BP).

TABLE 9 provides details regarding the experimental setup, including information regarding the liquid (unformulated) delivery construct and the vehicle.

TABLE 9

Experimental Setup of the In Vivo Study

| Group | Test Article | Vehicle | Formulation | Dose (mpk) | Route | N (4/ two TP) | Timepoints (hours) |
|---|---|---|---|---|---|---|---|
| 1 | Vehicle | PBS, pH 7 | Aq. bolus | na | P.O. | 4 | 1 |
| 2 | SEQ ID NO: 15 (liquid) | PBS, pH 7 | Aq. bolus | 90 | P.O. | 8 (4*2) | 1, 2, 4, 6 |

TABLE 10 summarizes properties of the SEQ ID NO: 15 construct as delivered in this experiment.

TABLE 10

Properties of Delivery Construct as Delivered in Liquid Form

| Groups | Groups | Cmax (pg/mL) | Tmax (hr) | AUC (0-6 hr) |
|---|---|---|---|---|
| SEQ ID NO: 15-Liquid | n/a | 24488 | 2 | 58126 |

Figure 25A:
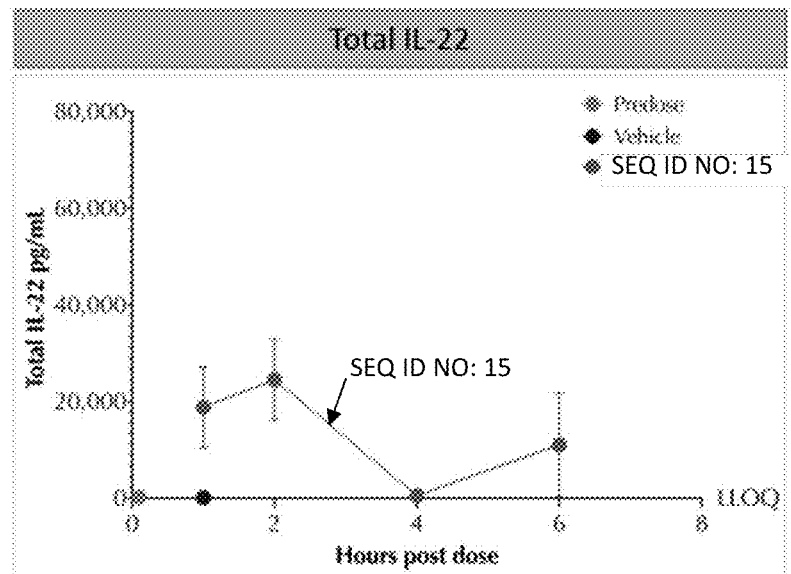
FIGS. 25A-25B illustrate graphs showing IL-22 plasma concentration as a function of time after administration of the delivery construct of SEQ ID NO: 15.
Figure 25B:
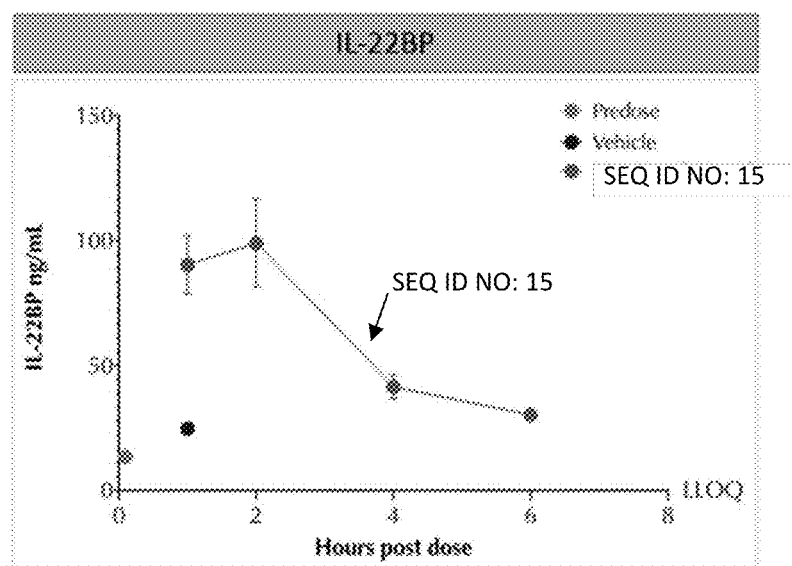
Figure 26A:
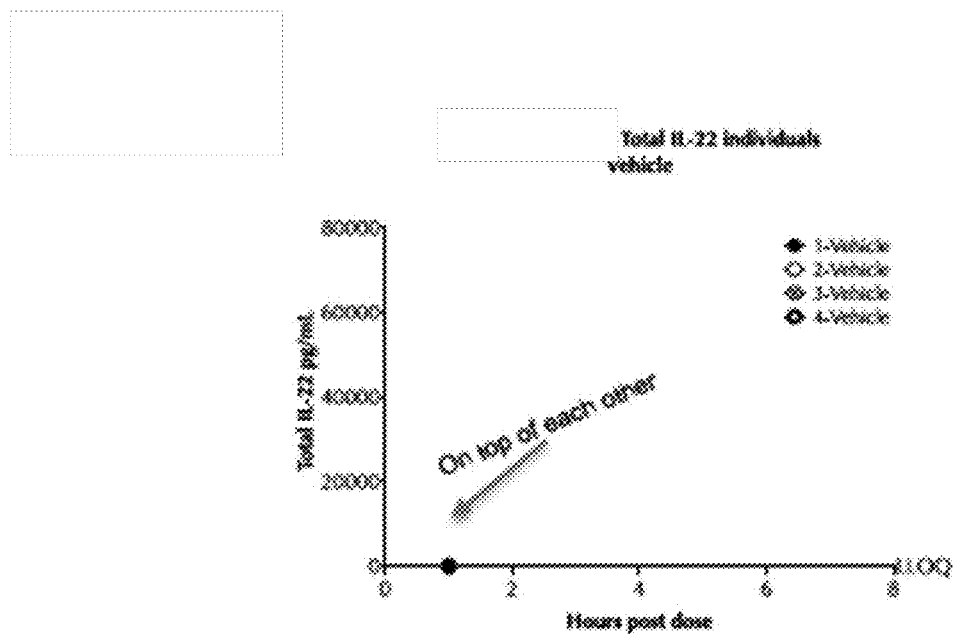
FIG. 26A (vehicle) and FIG. 26B (SEQ ID NO: 15) are graphs showing IL-22 plasma concentration as a function of time for individual mice.
Figure 26B:
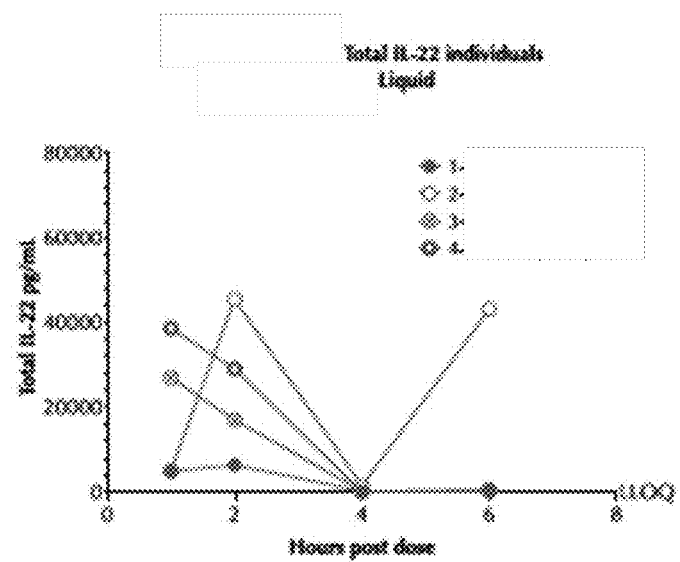

The total plasma IL-22 exposure was measured at the respective time points shown in TABLE 9. FIG. 25A shows total systemic IL-22 exposure (in pg/mL) and FIG. 25B shows IL-22BP exposure (in pg/mL) at the various time points where the blood samples and measurements were taken. FIG. 26A-FIG. 26B show individual measurements and data points for each group tested in this study.

It was observed that orally administered delivery construct having the sequence set forth in SEQ ID NO: 15 provided IL-22 in the plasma.

Example 17

Spacer Length and Coupling of Payload to the N- or C-Terminus of a Carrier does not Significantly Affect a Payload's Biological Activity This example shows that amino acid linkers of various lengths and the coupling of a heterologous payload to the N-terminus of a carrier does not significantly impact the payload's ability to bind its target when included into a delivery construct. The amino acid linkers examined were SEQ ID NO: 13 (GGGGSGGGGSGGGGS), SEQ ID NO: 28 (GGGGS), and SEQ ID NO: 31 (GGGGSGGGGSGGGGSGGGGSGGGGS).

The IL-22 receptor dimerization assay was performed by seeding DiscoverX HEK293 cells and incubating the cells for 16 h (5,000 cells per well) using the shown concentrations of agonist (delivery construct containing the IL-22 payload). The endpoint luminescence was read on a plate reader using PathHunter® eXpress IL22RA1/IL10RB Dimerization Assay.

FIG. 27A shows that the length of amino acid spacers with SEQ ID NOs: 13, 28, and 31 did not impact the ability of IL-22 (SEQ ID NO: 11) when included in the delivery constructs with SEQ ID NOs: 15, 32, and 33 to induce IL-22 receptor dimerization. The induction of receptor dimerization of control recombinant human IL-22 (rhIL-22, SEQ ID NO: 12) is shown by the black curve.

FIG. 27B shows that coupling of the IL-22 payload (SEQ ID NO: 11) to the N- or to the C-terminus of a carrier comprising amino acid residues 1-266 of SEQ ID NO: 1 via the spacer with SEQ ID NO: 28 did not significantly change the ability of the delivery constructs with SEQ ID NOs: 32, 34, and 35 to induce IL-22 receptor dimerization. The induction of receptor dimerization of control recombinant human IL-22 (rhIL-22) is shown by the black curve.

The pSTAT3 activation assay was conducted using Colo205 cells incubated with 10 μL of agonist (the respective delivery construct or IL-22 control) having the various concentrations for 15 min. The extent of pSTAT3 activation was then read using MSD STAT3 plates (Cat. No. N450SMA-1).

FIG. 27C shows that the length of amino acid spacers with SEQ ID NOs: 13, 28, and 31 did not impact the ability of IL-22 (SEQ ID NO: 11) when included in the delivery constructs with SEQ ID NOs: 15, 32, and 33 to induce pSTAT3 activation. The pSTAT3 activation of control recombinant human IL-22 (rhIL-22, SEQ ID NO: 12) is shown by the black curve.

FIG. 27D shows that coupling of the IL-22 payload (SEQ ID NO: 11) to the N- or to the C-terminus of a carrier comprising amino acid residues 1-266 of SEQ ID NO: 1 via the spacer with SEQ ID NO: 28 did not significantly change the ability of the delivery constructs with SEQ ID NOs: 32, 34, and 35 to induce pSTAT3 activation. The pSTAT3 activation of control recombinant human IL-22 (rhIL-22) is shown by the black curve.

What is claimed is:

1. A delivery construct comprising a carrier coupled to a payload, wherein the delivery construct has at least 90% sequence identity to SEQ ID NO: 17, and wherein the carrier consists of the amino acid sequence set forth in SEQ ID NO: 7 or SEQ ID NO: 9, or an amino acid sequence having at least 95% sequence identity thereto.

2. The delivery construct of claim 1, wherein the delivery construct comprises the amino acid sequence set forth in SEQ ID NO: 17.

3. The delivery construct of claim 1, wherein the delivery construct comprises the amino acid sequence set forth in SEQ ID NO: 15.

4. The delivery construct of claim 1, wherein the delivery construct has a glutamic acid at position 3 and an alanine at position 4.

5. The delivery construct of claim 4, wherein the carrier is 266 amino acids in length.

6. The delivery construct of claim 1, wherein the carrier consists of the amino acid sequence set forth in SEQ ID NO: 7.

7. The delivery construct of claim 1, wherein the carrier consists of the amino acid sequence set forth in SEQ ID NO: 9.

8. The delivery construct of claim 1, wherein the payload consists of the amino acid sequence set forth in SEQ ID NO: 11.

9. The delivery construct of claim 8, wherein the carrier is coupled covalently to the payload via a spacer that consists of the amino acid sequence set forth in SEQ ID NO: 13.

10. The delivery construct of claim 1, wherein the delivery construct consists of the amino acid sequence set forth in SEQ ID NO: 15 or SEQ ID NO: 17.

11. A method of treating an inflammatory disease of the gastrointestinal tract in a subject, the method comprising administering to the subject an effective amount of the delivery construct of claim 1.

12. The method of claim 11, wherein the inflammatory disease is Crohn's disease, ulcerative colitis, pouchitis, proctitis, or graft versus host disease.

13. The method of claim 12, wherein the disease is Crohn's disease or ulcerative colitis.

14. The delivery construct of claim 4, wherein the carrier consists of the amino acid sequence set forth in SEQ ID NO: 7 or SEQ ID NO: 9, or an amino acid sequence having at least 95% sequence identity thereto.

15. The delivery construct of claim 4, wherein the carrier consists of the amino acid sequence set forth in SEQ ID NO: 7 or SEQ ID NO: 9, or an amino acid sequence having at least 99% sequence identity thereto.

* * * * *

SEQUENCE LISTING

<160> NUMBER OF SEQ ID NOS: 41

<210> SEQ ID NO 1
<211> LENGTH: 634
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Val Glu Glu Ala Leu Asn Ile Phe Asp Glu Cys Arg Ser Pro Cys Ser
1               5                   10                  15

-continued

```
Leu Thr Pro Glu Pro Gly Lys Pro Ile Gln Ser Lys Leu Ser Ile Pro
             20                  25                  30
Ser Asp Val Val Leu Asp Glu Gly Val Leu Tyr Tyr Ser Met Thr Ile
         35                  40                  45
Asn Asp Glu Gln Asn Asp Ile Lys Asp Glu Asp Lys Gly Glu Ser Ile
     50                  55                  60
Ile Thr Ile Gly Glu Phe Ala Thr Val Arg Ala Thr Arg His Tyr Val
 65                  70                  75                  80
Asn Gln Asp Ala Pro Phe Gly Val Ile His Leu Asp Ile Thr Thr Glu
                 85                  90                  95
Asn Gly Thr Lys Thr Tyr Ser Tyr Asn Arg Lys Glu Gly Glu Phe Ala
            100                 105                 110
Ile Asn Trp Leu Val Pro Ile Gly Glu Asp Ser Pro Ala Ser Ile Lys
        115                 120                 125
Ile Ser Val Asp Glu Leu Asp Gln Gln Arg Asn Ile Ile Glu Val Pro
    130                 135                 140
Lys Leu Tyr Ser Ile Asp Leu Asp Asn Gln Thr Leu Glu Gln Trp Lys
145                 150                 155                 160
Thr Gln Gly Asn Val Ser Phe Ser Val Thr Arg Pro Glu His Asn Ile
                165                 170                 175
Ala Ile Ser Trp Pro Ser Val Ser Tyr Lys Ala Ala Gln Lys Glu Gly
            180                 185                 190
Ser Arg His Lys Arg Trp Ala His Trp His Thr Gly Leu Ala Leu Cys
        195                 200                 205
Trp Leu Val Pro Met Asp Ala Ile Tyr Asn Tyr Ile Thr Gln Gln Asn
    210                 215                 220
Cys Thr Leu Gly Asp Asn Trp Phe Gly Gly Ser Tyr Glu Thr Val Ala
225                 230                 235                 240
Gly Thr Pro Lys Val Ile Thr Val Lys Gln Gly Ile Glu Gln Lys Pro
                245                 250                 255
Val Glu Gln Arg Ile His Phe Ser Lys Gly Asn Ala Met Ser Ala Leu
            260                 265                 270
Ala Ala His Arg Val Cys Gly Val Pro Leu Glu Thr Leu Ala Arg Ser
        275                 280                 285
Arg Lys Pro Arg Asp Leu Thr Asp Leu Ser Cys Ala Tyr Gln Ala
    290                 295                 300
Gln Asn Ile Val Ser Leu Phe Val Ala Thr Arg Ile Leu Phe Ser His
305                 310                 315                 320
Leu Asp Ser Val Phe Thr Leu Asn Leu Asp Glu Gln Glu Pro Glu Val
                325                 330                 335
Ala Glu Arg Leu Ser Asp Leu Arg Arg Ile Asn Glu Asn Asn Pro Gly
            340                 345                 350
Met Val Thr Gln Val Leu Thr Val Ala Arg Gln Ile Tyr Asn Asp Tyr
        355                 360                 365
Val Thr His His Pro Gly Leu Thr Pro Glu Gln Thr Ser Ala Gly Ala
    370                 375                 380
Gln Ala Ala Asp Ile Leu Ser Leu Phe Cys Pro Asp Ala Asp Lys Ser
385                 390                 395                 400
Cys Val Ala Ser Asn Asn Asp Gln Ala Asn Ile Asn Ile Glu Ser Arg
                405                 410                 415
Ser Gly Arg Ser Tyr Leu Pro Glu Asn Arg Ala Val Ile Thr Pro Gln
            420                 425                 430
Gly Val Thr Asn Trp Thr Tyr Gln Glu Leu Glu Ala Thr His Gln Ala
```

```
                    435                 440                 445
Leu Thr Arg Glu Gly Tyr Val Phe Val Gly Tyr His Gly Thr Asn His
    450                 455                 460
Val Ala Ala Gln Thr Ile Val Asn Arg Ile Ala Pro Val Pro Arg Gly
465                 470                 475                 480
Asn Asn Thr Glu Asn Glu Glu Lys Trp Gly Gly Leu Tyr Val Ala Thr
                    485                 490                 495
His Ala Glu Val Ala His Gly Tyr Ala Arg Ile Lys Glu Gly Thr Gly
                500                 505                 510
Glu Tyr Gly Leu Pro Thr Arg Ala Glu Arg Asp Ala Arg Gly Val Met
            515                 520                 525
Leu Arg Val Tyr Ile Pro Arg Ala Ser Leu Glu Arg Phe Tyr Arg Thr
    530                 535                 540
Asn Thr Pro Leu Glu Asn Ala Glu Glu His Ile Thr Gln Val Ile Gly
545                 550                 555                 560
His Ser Leu Pro Leu Arg Asn Glu Ala Phe Thr Gly Pro Glu Ser Ala
                    565                 570                 575
Gly Gly Glu Asp Glu Thr Val Ile Gly Trp Asp Met Ala Ile His Ala
                580                 585                 590
Val Ala Ile Pro Ser Thr Ile Pro Gly Asn Ala Tyr Glu Glu Leu Ala
            595                 600                 605
Ile Asp Glu Glu Ala Val Ala Lys Glu Gln Ser Ile Ser Thr Lys Pro
610                 615                 620
Pro Tyr Lys Glu Arg Lys Asp Glu Leu Lys
625                 630

<210> SEQ ID NO 2
<211> LENGTH: 386
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Val Glu Glu Ala Leu Asn Ile Phe Asp Glu Cys Arg Ser Pro Cys Ser
1               5                   10                  15
Leu Thr Pro Glu Pro Gly Lys Pro Ile Gln Ser Lys Leu Ser Ile Pro
                20                  25                  30
Ser Asp Val Val Leu Asp Glu Gly Val Leu Tyr Tyr Ser Met Thr Ile
            35                  40                  45
Asn Asp Glu Gln Asn Asp Ile Lys Asp Glu Asp Lys Gly Glu Ser Ile
        50                  55                  60
Ile Thr Ile Gly Glu Phe Ala Thr Val Arg Ala Thr Arg His Tyr Val
65                  70                  75                  80
Asn Gln Asp Ala Pro Phe Gly Val Ile His Leu Asp Ile Thr Thr Glu
                85                  90                  95
Asn Gly Thr Lys Thr Tyr Ser Tyr Asn Arg Lys Glu Gly Glu Phe Ala
                100                 105                 110
Ile Asn Trp Leu Val Pro Ile Gly Glu Asp Ser Pro Ala Ser Ile Lys
            115                 120                 125
Ile Ser Val Asp Glu Leu Asp Gln Gln Arg Asn Ile Ile Glu Val Pro
        130                 135                 140
Lys Leu Tyr Ser Ile Asp Leu Asp Asn Gln Thr Leu Glu Gln Trp Lys
145                 150                 155                 160
```

```
Thr Gln Gly Asn Val Ser Phe Ser Val Thr Arg Pro Glu His Asn Ile
            165                 170                 175

Ala Ile Ser Trp Pro Ser Val Ser Tyr Lys Ala Ala Gln Lys Glu Gly
        180                 185                 190

Ser Arg His Lys Arg Trp Ala His Trp His Thr Gly Leu Ala Leu Cys
            195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala
385

<210> SEQ ID NO 3
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125
```

```
Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly
            260                 265

<210> SEQ ID NO 4
<211> LENGTH: 386
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Leu Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
```

```
                    210                 215                 220
Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala
385

<210> SEQ ID NO 5
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Leu Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175
```

```
Ala Ile Ser Trp Pro Ser Val Ser Tyr Lys Ala Ala Gln Lys Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly
            260                 265
```

<210> SEQ ID NO 6
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
            85                  90                  95

Glu Asn Gly Thr Lys Thr Tyr Ser Tyr Asn Arg Lys Glu Gly Glu Phe
        100                 105                 110

Ala Ile Asn Trp Leu Val Pro Ile Gly Glu Asp Ser Pro Ala Ser Ile
    115                 120                 125

Lys Ile Ser Val Asp Glu Leu Asp Gln Gln Arg Asn Ile Ile Glu Val
130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
        195                 200                 205

Cys Trp Leu Val Pro Met Asp Ala Ile Tyr Asn Tyr Ile Thr Gln Gln
    210                 215                 220

Asn Cys Thr Leu Gly Asp Asn Trp Phe Gly Gly Ser Tyr Glu Thr Val
225                 230                 235                 240

Ala Gly Thr Pro Lys Val Ile Thr Val Lys Gln Gly Ile Glu Gln Lys
                245                 250                 255

Pro Val Glu Gln Arg Ile His Phe Ser Lys Gly Asn Ala Met Ser Ala
            260                 265                 270
```

```
Leu Ala Ala His Arg Val Cys Gly Val Pro Leu Glu Thr Leu Ala Arg
            275                 280                 285

Ser Arg Lys Pro Arg Asp Leu Thr Asp Asp Leu Ser Cys Ala Tyr Gln
290                 295                 300

Ala Gln Asn Ile Val Ser Leu Phe Val Ala Thr Arg Ile Leu Phe Ser
305                 310                 315                 320

His Leu Asp Ser Val Phe Thr Leu Asn Leu Asp Glu Gln Gln Pro Glu
            325                 330                 335

Val Ala Glu Arg Leu Ser Asp Leu Arg Arg Ile Asn Glu Asn Asn Pro
            340                 345                 350

Gly Met Val Thr Gln Val Leu Thr Val Ala Arg Gln Ile Tyr Asn Asp
            355                 360                 365

Tyr Val Thr His His Pro Gly Leu Thr Pro Glu Gln Thr Ser Ala Gly
            370                 375                 380

Ala Gln Ala
385

<210> SEQ ID NO 7
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
    50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
    130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp Thr Gly Leu Ala Leu
        195                 200                 205

Cys Trp Leu Val Pro Met Asp Ala Ile Tyr Asn Tyr Ile Thr Gln Gln
    210                 215                 220

Asn Cys Thr Leu Gly Asp Asn Trp Phe Gly Gly Ser Tyr Glu Thr Val
```

```
                225                 230                 235                 240

Ala Gly Thr Pro Lys Val Ile Thr Val Lys Gln Gly Ile Glu Gln Lys
                245                 250                 255

Pro Val Glu Gln Arg Ile His Phe Ser Lys Gly
                260                 265

<210> SEQ ID NO 8
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Leu Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
                20                  25                  30

Pro Ser Asp Val Val Leu Asp Glu Gly Val Leu Tyr Tyr Ser Met Thr
            35                  40                  45

Ile Asn Asp Glu Gln Asn Asp Ile Lys Asp Glu Asp Lys Gly Glu Ser
        50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
                100                 105                 110

Ala Ile Asn Trp Leu Val Pro Ile Gly Glu Asp Ser Pro Ala Ser Ile
            115                 120                 125

Lys Ile Ser Val Asp Glu Leu Asp Gln Gln Arg Asn Ile Ile Glu Val
        130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
                180                 185                 190

Gly Ser Arg His Lys Arg Trp Ala His Trp His Thr Gly Leu Ala Leu
            195                 200                 205

Cys Trp Leu Val Pro Met Asp Ala Ile Tyr Asn Tyr Ile Thr Gln Gln
        210                 215                 220

Asn Cys Thr Leu Gly Asp Asn Trp Phe Gly Gly Ser Tyr Glu Thr Val
225                 230                 235                 240

Ala Gly Thr Pro Lys Val Ile Thr Val Lys Gln Gly Ile Glu Gln Lys
                245                 250                 255

Pro Val Glu Gln Arg Ile His Phe Ser Lys Gly Asn Ala Met Ser Ala
                260                 265                 270

Leu Ala Ala His Arg Val Cys Gly Val Pro Leu Glu Thr Leu Ala Arg
            275                 280                 285

Ser Arg Lys Pro Arg Asp Leu Thr Asp Leu Ser Cys Ala Tyr Gln
        290                 295                 300

Ala Gln Asn Ile Val Ser Leu Phe Val Ala Thr Arg Ile Leu Phe Ser
305                 310                 315                 320
```

His Leu Asp Ser Val Phe Thr Leu Asn Leu Asp Glu Gln Glu Pro Glu
            325                 330                 335

Val Ala Glu Arg Leu Ser Asp Leu Arg Arg Ile Asn Glu Asn Asn Pro
        340                 345                 350

Gly Met Val Thr Gln Val Leu Thr Val Ala Arg Gln Ile Tyr Asn Asp
    355                 360                 365

Tyr Val Thr His His Pro Gly Leu Thr Pro Glu Gln Thr Ser Ala Gly
370                 375                 380

Ala Gln Ala
385

<210> SEQ ID NO 9
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Leu Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
    50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
    130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
        195                 200                 205

Cys Trp Leu Val Pro Met Asp Ala Ile Tyr Asn Tyr Ile Thr Gln Gln
    210                 215                 220

Asn Cys Thr Leu Gly Asp Asn Trp Phe Gly Gly Ser Tyr Glu Thr Val
225                 230                 235                 240

Ala Gly Thr Pro Lys Val Ile Thr Val Lys Gln Gly Ile Glu Gln Lys
                245                 250                 255

Pro Val Glu Gln Arg Ile His Phe Ser Lys Gly
            260                 265

<210> SEQ ID NO 10

<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ala Ala Leu Gln Lys Ser Val Ser Ser Phe Leu Met Gly Thr Leu
1               5                   10                  15

Ala Thr Ser Cys Leu Leu Leu Ala Leu Leu Val Gln Gly Gly Ala
            20                  25                  30

Ala Ala Pro Ile Ser Ser His Cys Arg Leu Asp Lys Ser Asn Phe Gln
        35                  40                  45

Gln Pro Tyr Ile Thr Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
        115                 120                 125

Leu Ser Thr Cys His Ile Glu Gly Asp Asp Leu His Ile Gln Arg Asn
    130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile

<210> SEQ ID NO 11
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

```
Lys Ala Ile Gly Glu Leu Asp Leu Leu Phe Met Ser Leu Arg Asn Ala
    130                 135                 140

Cys Ile
145

<210> SEQ ID NO 12
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Ala Pro Ile Ser Ser His Cys Arg Leu Asp Lys Ser Asn Phe Gln
1               5                   10                  15

Gln Pro Tyr Ile Thr Asn Arg Thr Phe Met Leu Ala Lys Glu Ala Ser
            20                  25                  30

Leu Ala Asp Asn Asn Thr Asp Val Arg Leu Ile Gly Glu Lys Leu Phe
        35                  40                  45

His Gly Val Ser Met Ser Glu Arg Cys Tyr Leu Met Lys Gln Val Leu
    50                  55                  60

Asn Phe Thr Leu Glu Glu Val Leu Phe Pro Gln Ser Asp Arg Phe Gln
65                  70                  75                  80

Pro Tyr Met Gln Glu Val Val Pro Phe Leu Ala Arg Leu Ser Asn Arg
                85                  90                  95

Leu Ser Thr Cys His Ile Glu Gly Asp Asp Leu His Ile Gln Arg Asn
            100                 105                 110

Val Gln Lys Leu Lys Asp Thr Val Lys Lys Leu Gly Glu Ser Gly Glu
        115                 120                 125

Ile Lys Ala Ile Gly Glu Leu Asp Leu Leu Phe Met Ser Leu Arg Asn
    130                 135                 140

Ala Cys Ile
145

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Gly Ser Gly Gly Gly Ser Gly Gly Gly Gly Ser
1               5                   10                  15

<210> SEQ ID NO 14
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Leu Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
```

```
                35                  40                  45
Ile Asn Asp Glu Gln Asn Asp Ile Lys Asp Glu Asp Lys Gly Glu Ser
 50                  55                  60

Ile Ile Thr Ile Gly Glu Phe Ala Thr Val Arg Ala Thr Arg His Tyr
 65                  70                  75                  80

Val Asn Gln Asp Ala Pro Phe Gly Val Ile His Leu Asp Ile Thr Thr
                 85                  90                  95

Glu Asn Gly Thr Lys Thr Tyr Ser Tyr Asn Arg Lys Glu Gly Glu Phe
                100                 105                 110

Ala Ile Asn Trp Leu Val Pro Ile Gly Glu Asp Ser Pro Ala Ser Ile
                115                 120                 125

Lys Ile Ser Val Asp Glu Leu Asp Gln Gln Arg Asn Ile Ile Glu Val
                130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
                180                 185                 190

Gly Ser Arg His Lys Arg Trp Ala His Trp His Thr Gly Leu Ala Leu
                195                 200                 205

Cys Trp Leu Val Pro Met Asp Ala Ile Tyr Asn Tyr Ile Thr Gln Gln
210                 215                 220

Asn Cys Thr Leu Gly Asp Asn Trp Phe Gly Gly Ser Tyr Glu Thr Val
225                 230                 235                 240

Ala Gly Thr Pro Lys Val Ile Thr Val Lys Gln Gly Ile Glu Gln Lys
                245                 250                 255

Pro Val Glu Gln Arg Ile His Phe Ser Lys Gly Asn Ala Met Ser Ala
                260                 265                 270

Leu Ala Ala His Arg Val Cys Gly Val Pro Leu Glu Thr Leu Ala Arg
                275                 280                 285

Ser Arg Lys Pro Arg Asp Leu Thr Asp Asp Leu Ser Cys Ala Tyr Gln
290                 295                 300

Ala Gln Asn Ile Val Ser Leu Phe Val Ala Thr Arg Ile Leu Phe Ser
305                 310                 315                 320

His Leu Asp Ser Val Phe Thr Leu Asn Leu Asp Glu Gln Glu Pro Glu
                325                 330                 335

Val Ala Glu Arg Leu Ser Asp Leu Arg Arg Ile Asn Glu Asn Asn Pro
                340                 345                 350

Gly Met Val Thr Gln Val Leu Thr Val Ala Arg Gln Ile Tyr Asn Asp
                355                 360                 365

Tyr Val Thr His His Pro Gly Leu Thr Pro Glu Gln Thr Ser Ala Gly
                370                 375                 380

Ala Gln Ala Gly Gly Gly Ser Gly Gly Gly Ser Gly Gly Gly
385                 390                 395                 400

Gly Ser Ala Pro Ile Ser Ser His Cys Arg Leu Asp Lys Ser Asn Phe
                405                 410                 415

Gln Gln Pro Tyr Ile Thr Asn Arg Thr Phe Met Leu Ala Lys Glu Ala
                420                 425                 430

Ser Leu Ala Asp Asn Asn Thr Asp Val Arg Leu Ile Gly Glu Lys Leu
                435                 440                 445

Phe His Gly Val Ser Met Ser Glu Arg Cys Tyr Leu Met Lys Gln Val
450                 455                 460
```

Leu Asn Phe Thr Leu Glu Glu Val Leu Phe Pro Gln Ser Asp Arg Phe
465                 470                 475                 480

Gln Pro Tyr Met Gln Glu Val Val Pro Phe Leu Ala Arg Leu Ser Asn
                485                 490                 495

Arg Leu Ser Thr Cys His Ile Glu Gly Asp Asp Leu His Ile Gln Arg
            500                 505                 510

Asn Val Gln Lys Leu Lys Asp Thr Val Lys Lys Leu Gly Glu Ser Gly
        515                 520                 525

Glu Ile Lys Ala Ile Gly Glu Leu Asp Leu Leu Phe Met Ser Leu Arg
    530                 535                 540

Asn Ala Cys Ile
545

<210> SEQ ID NO 15
<211> LENGTH: 428
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
    50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
    130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
        195                 200                 205

Cys Trp Leu Val Pro Met Asp Ala Ile Tyr Asn Tyr Ile Thr Gln Gln
    210                 215                 220

Asn Cys Thr Leu Gly Asp Asn Trp Phe Gly Ser Tyr Glu Thr Val
225                 230                 235                 240

Ala Gly Thr Pro Lys Val Ile Thr Val Lys Gln Gly Ile Glu Gln Lys
                245                 250                 255

Pro Val Glu Gln Arg Ile His Phe Ser Lys Gly Gly Gly Gly Gly Ser

```
                        260                 265                 270
Gly Gly Gly Gly Ser Gly Gly Gly Ser Ala Pro Ile Ser Ser His
            275                 280                 285

Cys Arg Leu Asp Lys Ser Asn Phe Gln Gln Pro Tyr Ile Thr Asn Arg
        290                 295                 300

Thr Phe Met Leu Ala Lys Glu Ala Ser Leu Ala Asp Asn Asn Thr Asp
305                 310                 315                 320

Val Arg Leu Ile Gly Glu Lys Leu Phe His Gly Val Ser Met Ser Glu
                325                 330                 335

Arg Cys Tyr Leu Met Lys Gln Val Leu Asn Phe Thr Leu Glu Glu Val
            340                 345                 350

Leu Phe Pro Gln Ser Asp Arg Phe Gln Pro Tyr Met Gln Glu Val Val
        355                 360                 365

Pro Phe Leu Ala Arg Leu Ser Asn Arg Leu Ser Thr Cys His Ile Glu
    370                 375                 380

Gly Asp Asp Leu His Ile Gln Arg Asn Val Gln Lys Leu Lys Asp Thr
385                 390                 395                 400

Val Lys Lys Leu Gly Glu Ser Gly Glu Ile Lys Ala Ile Gly Glu Leu
                405                 410                 415

Asp Leu Leu Phe Met Ser Leu Arg Asn Ala Cys Ile
            420                 425

<210> SEQ ID NO 16
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
    50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
    130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190
```

Gly Ser Arg His Lys Arg Trp Ala His Trp His Thr Gly Leu Ala Leu
            195                 200                 205

Cys Trp Leu Val Pro Met Asp Ala Ile Tyr Asn Tyr Ile Thr Gln Gln
210                 215                 220

Asn Cys Thr Leu Gly Asp Asn Trp Phe Gly Gly Ser Tyr Glu Thr Val
225                 230                 235                 240

Ala Gly Thr Pro Lys Val Ile Thr Val Lys Gln Gly Ile Glu Gln Lys
            245                 250                 255

Pro Val Glu Gln Arg Ile His Phe Ser Lys Gly Asn Ala Met Ser Ala
            260                 265                 270

Leu Ala Ala His Arg Val Cys Gly Val Pro Leu Glu Thr Leu Ala Arg
            275                 280                 285

Ser Arg Lys Pro Arg Asp Leu Thr Asp Asp Leu Ser Cys Ala Tyr Gln
            290                 295                 300

Ala Gln Asn Ile Val Ser Leu Phe Val Ala Thr Arg Ile Leu Phe Ser
305                 310                 315                 320

His Leu Asp Ser Val Phe Thr Leu Asn Leu Asp Glu Gln Glu Pro Glu
                325                 330                 335

Val Ala Glu Arg Leu Ser Asp Leu Arg Arg Ile Asn Glu Asn Asn Pro
            340                 345                 350

Gly Met Val Thr Gln Val Leu Thr Val Ala Arg Gln Ile Tyr Asn Asp
            355                 360                 365

Tyr Val Thr His His Pro Gly Leu Thr Pro Glu Gln Thr Ser Ala Gly
            370                 375                 380

Ala Gln Ala Gly Gly Gly Ser Gly Gly Gly Ser Gly Gly Gly
385                 390                 395                 400

Gly Ser Ala Pro Ile Ser Ser His Cys Arg Leu Asp Lys Ser Asn Phe
            405                 410                 415

Gln Gln Pro Tyr Ile Thr Asn Arg Thr Phe Met Leu Ala Lys Glu Ala
            420                 425                 430

Ser Leu Ala Asp Asn Asn Thr Asp Val Arg Leu Ile Gly Glu Lys Leu
            435                 440                 445

Phe His Gly Val Ser Met Ser Glu Arg Cys Tyr Leu Met Lys Gln Val
450                 455                 460

Leu Asn Phe Thr Leu Glu Glu Val Leu Phe Pro Gln Ser Asp Arg Phe
465                 470                 475                 480

Gln Pro Tyr Met Gln Glu Val Val Pro Phe Leu Ala Arg Leu Ser Asn
            485                 490                 495

Arg Leu Ser Thr Cys His Ile Glu Gly Asp Asp Leu His Ile Gln Arg
            500                 505                 510

Asn Val Gln Lys Leu Lys Asp Thr Val Lys Lys Leu Gly Glu Ser Gly
            515                 520                 525

Glu Ile Lys Ala Ile Gly Glu Leu Asp Leu Leu Phe Met Ser Leu Arg
530                 535                 540

Asn Ala Cys Ile
545

<210> SEQ ID NO 17
<211> LENGTH: 428
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Met Leu Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
            85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
            115                 120                 125

Lys Ile Ser Val Asp Glu Leu Asp Gln Gln Arg Asn Ile Ile Glu Val
            130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
                180                 185                 190

Gly Ser Arg His Lys Arg Trp Ala His Trp His Thr Gly Leu Ala Leu
                195                 200                 205

Cys Trp Leu Val Pro Met Asp Ala Ile Tyr Asn Tyr Ile Thr Gln Gln
210                 215                 220

Asn Cys Thr Leu Gly Asp Asn Trp Phe Gly Gly Ser Tyr Glu Thr Val
225                 230                 235                 240

Ala Gly Thr Pro Lys Val Ile Thr Val Lys Gln Gly Ile Glu Gln Lys
                245                 250                 255

Pro Val Glu Gln Arg Ile His Phe Ser Lys Gly Gly Gly Gly Gly Ser
            260                 265                 270

Gly Gly Gly Gly Ser Gly Gly Gly Ser Ala Pro Ile Ser Ser His
            275                 280                 285

Cys Arg Leu Asp Lys Ser Asn Phe Gln Gln Pro Tyr Ile Thr Asn Arg
            290                 295                 300

Thr Phe Met Leu Ala Lys Glu Ala Ser Leu Ala Asp Asn Asn Thr Asp
305                 310                 315                 320

Val Arg Leu Ile Gly Glu Lys Leu Phe His Gly Val Ser Met Ser Glu
                325                 330                 335

Arg Cys Tyr Leu Met Lys Gln Val Leu Asn Phe Thr Leu Glu Glu Val
            340                 345                 350

Leu Phe Pro Gln Ser Asp Arg Phe Gln Pro Tyr Met Gln Glu Val Val
            355                 360                 365

Pro Phe Leu Ala Arg Leu Ser Asn Arg Leu Ser Thr Cys His Ile Glu
            370                 375                 380

Gly Asp Asp Leu His Ile Gln Arg Asn Val Gln Lys Leu Lys Asp Thr
385                 390                 395                 400

Val Lys Lys Leu Gly Glu Ser Gly Glu Ile Lys Ala Ile Gly Glu Leu
                405                 410                 415
```

Asp Leu Leu Phe Met Ser Leu Arg Asn Ala Cys Ile
            420                 425

<210> SEQ ID NO 18
<211> LENGTH: 547
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

```
Met Val Thr Gln Val Leu Thr Val Ala Arg Gln Ile Tyr Asn Asp Tyr
            355                 360                 365

Val Thr His His Pro Gly Leu Thr Pro Glu Gln Thr Ser Ala Gly Ala
    370                 375                 380

Gln Ala Gly Gly Gly Ser Gly Gly Gly Ser Gly Gly Gly Gly
385                 390                 395                 400

Ser Ala Pro Ile Ser Ser His Cys Arg Leu Asp Lys Ser Asn Phe Gln
                405                 410                 415

Gln Pro Tyr Ile Thr Asn Arg Thr Phe Met Leu Ala Lys Glu Ala Ser
            420                 425                 430

Leu Ala Asp Asn Asn Thr Asp Val Arg Leu Ile Gly Glu Lys Leu Phe
            435                 440                 445

His Gly Val Ser Met Ser Glu Arg Cys Tyr Leu Met Lys Gln Val Leu
    450                 455                 460

Asn Phe Thr Leu Glu Glu Val Leu Phe Pro Gln Ser Asp Arg Phe Gln
465                 470                 475                 480

Pro Tyr Met Gln Glu Val Val Pro Phe Leu Ala Arg Leu Ser Asn Arg
                485                 490                 495

Leu Ser Thr Cys His Ile Glu Gly Asp Asp Leu His Ile Gln Arg Asn
                500                 505                 510

Val Gln Lys Leu Lys Asp Thr Val Lys Lys Leu Gly Glu Ser Gly Glu
            515                 520                 525

Ile Lys Ala Ile Gly Glu Leu Asp Leu Leu Phe Met Ser Leu Arg Asn
530                 535                 540

Ala Cys Ile
545

<210> SEQ ID NO 19
<211> LENGTH: 547
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Leu Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
        130                 135                 140

Lys Leu Tyr Ser Ile Asp Leu Asp Asn Gln Thr Leu Glu Gln Trp Lys
```

-continued

```
            145                 150                 155                 160
        Thr Gln Gly Asn Val Ser Phe Ser Val Thr Arg Pro Glu His Asn Ile
                        165                 170                 175
        Ala Ile Ser Trp Pro Ser Val Ser Tyr Lys Ala Ala Gln Lys Glu Gly
                        180                 185                 190
        Ser Arg His Lys Arg Trp Ala Trp His Thr Gly Leu Ala Leu Cys
                        195                 200                 205
        Trp Leu Val Pro Met Asp Ala Ile Tyr Asn Tyr Ile Thr Gln Gln Asn
            210                 215                 220
        Cys Thr Leu Gly Asp Asn Trp Phe Gly Gly Ser Tyr Glu Thr Val Ala
        225                 230                 235                 240
        Gly Thr Pro Lys Val Ile Thr Val Lys Gln Gly Ile Glu Gln Lys Pro
                        245                 250                 255
        Val Glu Gln Arg Ile His Phe Ser Lys Gly Asn Ala Met Ser Ala Leu
                        260                 265                 270
        Ala Ala His Arg Val Cys Gly Val Pro Leu Glu Thr Leu Ala Arg Ser
                        275                 280                 285
        Arg Lys Pro Arg Asp Leu Thr Asp Asp Leu Ser Cys Ala Tyr Gln Ala
                        290                 295                 300
        Gln Asn Ile Val Ser Leu Phe Val Ala Thr Arg Ile Leu Phe Ser His
        305                 310                 315                 320
        Leu Asp Ser Val Phe Thr Leu Asn Leu Asp Glu Gln Glu Pro Glu Val
                        325                 330                 335
        Ala Glu Arg Leu Ser Asp Leu Arg Arg Ile Asn Glu Asn Asn Pro Gly
                        340                 345                 350
        Met Val Thr Gln Val Leu Thr Val Ala Arg Gln Ile Tyr Asn Asp Tyr
                        355                 360                 365
        Val Thr His His Pro Gly Leu Thr Pro Glu Gln Thr Ser Ala Gly Ala
                        370                 375                 380
        Gln Ala Gly Gly Gly Ser Gly Gly Gly Ser Gly Gly Gly Gly
        385                 390                 395                 400
        Ser Ala Pro Ile Ser Ser His Cys Arg Leu Asp Lys Ser Asn Phe Gln
                        405                 410                 415
        Gln Pro Tyr Ile Thr Asn Arg Thr Phe Met Leu Ala Lys Glu Ala Ser
                        420                 425                 430
        Leu Ala Asp Asn Asn Thr Asp Val Arg Leu Ile Gly Glu Lys Leu Phe
                        435                 440                 445
        His Gly Val Ser Met Ser Glu Arg Cys Tyr Leu Met Lys Gln Val Leu
            450                 455                 460
        Asn Phe Thr Leu Glu Glu Val Leu Phe Pro Gln Ser Asp Arg Phe Gln
        465                 470                 475                 480
        Pro Tyr Met Gln Glu Val Val Pro Phe Leu Ala Arg Leu Ser Asn Arg
                        485                 490                 495
        Leu Ser Thr Cys His Ile Glu Gly Asp Asp Leu His Ile Gln Arg Asn
                        500                 505                 510
        Val Gln Lys Leu Lys Asp Thr Val Lys Lys Leu Gly Glu Ser Gly Glu
                        515                 520                 525
        Ile Lys Ala Ile Gly Glu Leu Asp Leu Leu Phe Met Ser Leu Arg Asn
                        530                 535                 540
        Ala Cys Ile
        545

<210> SEQ ID NO 20
```

```
<211> LENGTH: 427
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Gly Gly Gly Ser Gly
            260                 265                 270

Gly Gly Gly Ser Gly Gly Gly Ser Ala Pro Ile Ser Ser His Cys
        275                 280                 285

Arg Leu Asp Lys Ser Asn Phe Gln Gln Pro Tyr Ile Thr Asn Arg Thr
290                 295                 300

Phe Met Leu Ala Lys Glu Ala Ser Leu Ala Asp Asn Asn Thr Asp Val
305                 310                 315                 320

Arg Leu Ile Gly Glu Lys Leu Phe His Gly Val Ser Met Ser Glu Arg
                325                 330                 335

Cys Tyr Leu Met Lys Gln Val Leu Asn Phe Thr Leu Glu Glu Val Leu
            340                 345                 350

Phe Pro Gln Ser Asp Arg Phe Gln Pro Tyr Met Gln Glu Val Val Pro
        355                 360                 365

Phe Leu Ala Arg Leu Ser Asn Arg Leu Ser Thr Cys His Ile Glu Gly
```

```
                370             375             380
Asp Asp Leu His Ile Gln Arg Asn Val Gln Lys Leu Lys Asp Thr Val
385                 390             395                 400

Lys Lys Leu Gly Glu Ser Gly Glu Ile Lys Ala Ile Gly Glu Leu Asp
                405             410             415

Leu Leu Phe Met Ser Leu Arg Asn Ala Cys Ile
            420             425

<210> SEQ ID NO 21
<211> LENGTH: 427
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Leu Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Gly Gly Gly Ser Gly
            260                 265                 270

Gly Gly Gly Ser Gly Gly Gly Gly Ser Ala Pro Ile Ser Ser His Cys
        275                 280                 285

Arg Leu Asp Lys Ser Asn Phe Gln Gln Pro Tyr Ile Thr Asn Arg Thr
        290                 295                 300
```

```
Phe Met Leu Ala Lys Glu Ala Ser Leu Ala Asp Asn Thr Asp Val
305                 310                 315                 320

Arg Leu Ile Gly Glu Lys Leu Phe His Gly Val Ser Met Ser Glu Arg
            325                 330                 335

Cys Tyr Leu Met Lys Gln Val Leu Asn Phe Thr Leu Glu Glu Val Leu
            340                 345                 350

Phe Pro Gln Ser Asp Arg Phe Gln Pro Tyr Met Gln Glu Val Val Pro
            355                 360                 365

Phe Leu Ala Arg Leu Ser Asn Arg Leu Ser Thr Cys His Ile Glu Gly
            370                 375                 380

Asp Asp Leu His Ile Gln Arg Asn Val Gln Lys Leu Lys Asp Thr Val
385                 390                 395                 400

Lys Lys Leu Gly Glu Ser Gly Glu Ile Lys Ala Ile Gly Glu Leu Asp
                405                 410                 415

Leu Leu Phe Met Ser Leu Arg Asn Ala Cys Ile
            420                 425

<210> SEQ ID NO 22
<211> LENGTH: 634
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Leu Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240
```

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile Glu Ser Arg
                405                 410                 415

Ser Gly Arg Ser Tyr Leu Pro Glu Asn Arg Ala Val Ile Thr Pro Gln
            420                 425                 430

Gly Val Thr Asn Trp Thr Tyr Gln Glu Leu Glu Ala Thr His Gln Ala
        435                 440                 445

Leu Thr Arg Glu Gly Tyr Val Phe Val Gly Tyr His Gly Thr Asn His
    450                 455                 460

Val Ala Ala Gln Thr Ile Val Asn Arg Ile Ala Pro Val Pro Arg Gly
465                 470                 475                 480

Asn Asn Thr Glu Asn Glu Glu Lys Trp Gly Gly Leu Tyr Val Ala Thr
                485                 490                 495

His Ala Glu Val Ala His Gly Tyr Ala Arg Ile Lys Gly Gly Thr Gly
            500                 505                 510

Glu Tyr Gly Leu Pro Thr Arg Ala Glu Arg Asp Ala Arg Gly Val Met
        515                 520                 525

Leu Arg Val Tyr Ile Pro Arg Ala Ser Leu Glu Arg Phe Tyr Arg Thr
    530                 535                 540

Asn Thr Pro Leu Glu Asn Ala Glu Glu His Ile Thr Gln Val Ile Gly
545                 550                 555                 560

His Ser Leu Pro Leu Arg Asn Glu Ala Phe Thr Gly Pro Glu Ser Ala
                565                 570                 575

Gly Gly Glu Asp Glu Thr Val Ile Gly Trp Asp Met Ala Ile His Ala
            580                 585                 590

Val Ala Ile Pro Ser Thr Ile Pro Gly Asn Ala Tyr Glu Glu Leu Ala
        595                 600                 605

Ile Asp Glu Glu Ala Val Ala Lys Glu Gln Ser Ile Ser Thr Lys Pro
    610                 615                 620

Pro Tyr Lys Glu Arg Lys Asp Glu Leu Lys
625                 630

<210> SEQ ID NO 23
<211> LENGTH: 635

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Met Leu Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
            85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
            115                 120                 125

Lys Ile Ser Val Asp Glu Leu Asp Gln Gln Arg Asn Ile Ile Glu Val
130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
            195                 200                 205

Cys Trp Leu Val Pro Met Asp Ala Ile Tyr Asn Tyr Ile Thr Gln Gln
210                 215                 220

Asn Cys Thr Leu Gly Asp Asn Trp Phe Gly Gly Ser Tyr Glu Thr Val
225                 230                 235                 240

Ala Gly Thr Pro Lys Val Ile Thr Val Lys Gln Gly Ile Glu Gln Lys
                245                 250                 255

Pro Val Glu Gln Arg Ile His Phe Ser Lys Gly Asn Ala Met Ser Ala
            260                 265                 270

Leu Ala Ala His Arg Val Cys Gly Val Pro Leu Glu Thr Leu Ala Arg
            275                 280                 285

Ser Arg Lys Pro Arg Asp Leu Thr Asp Leu Ser Cys Ala Tyr Gln
            290                 295                 300

Ala Gln Asn Ile Val Ser Leu Phe Val Ala Thr Arg Ile Leu Phe Ser
305                 310                 315                 320

His Leu Asp Ser Val Phe Thr Leu Asn Leu Asp Glu Gln Glu Pro Glu
                325                 330                 335

Val Ala Glu Arg Leu Ser Asp Leu Arg Arg Ile Asn Glu Asn Asn Pro
            340                 345                 350

Gly Met Val Thr Gln Val Leu Thr Val Ala Arg Gln Ile Tyr Asn Asp
            355                 360                 365

Tyr Val Thr His His Pro Gly Leu Thr Pro Glu Gln Thr Ser Ala Gly
            370                 375                 380
```

Ala Gln Ala Ala Asp Ile Leu Ser Leu Phe Cys Pro Asp Ala Asp Lys
385                 390                 395                 400

Ser Cys Val Ala Ser Asn Asn Asp Gln Ala Asn Ile Asn Ile Glu Ser
            405                 410                 415

Arg Ser Gly Arg Ser Tyr Leu Pro Glu Asn Arg Ala Val Ile Thr Pro
        420                 425                 430

Gln Gly Val Thr Asn Trp Thr Tyr Gln Glu Leu Glu Ala Thr His Gln
    435                 440                 445

Ala Leu Thr Arg Glu Gly Tyr Val Phe Val Gly Tyr His Gly Thr Asn
450                 455                 460

His Val Ala Ala Gln Thr Ile Val Asn Arg Ile Ala Pro Val Pro Arg
465                 470                 475                 480

Gly Asn Asn Thr Glu Asn Glu Glu Lys Trp Gly Gly Leu Tyr Val Ala
            485                 490                 495

Thr His Ala Glu Val Ala His Gly Tyr Ala Arg Ile Lys Glu Gly Thr
        500                 505                 510

Gly Glu Tyr Gly Leu Pro Thr Arg Ala Glu Arg Asp Ala Arg Gly Val
    515                 520                 525

Met Leu Arg Val Tyr Ile Pro Arg Ala Ser Leu Glu Arg Phe Tyr Arg
530                 535                 540

Thr Asn Thr Pro Leu Glu Asn Ala Glu His Ile Thr Gln Val Ile
545                 550                 555                 560

Gly His Ser Leu Pro Leu Arg Asn Glu Ala Phe Thr Gly Pro Glu Ser
            565                 570                 575

Ala Gly Gly Glu Asp Glu Thr Val Ile Gly Trp Asp Met Ala Ile His
        580                 585                 590

Ala Val Ala Ile Pro Ser Thr Ile Pro Gly Asn Ala Tyr Glu Glu Leu
    595                 600                 605

Ala Ile Asp Glu Glu Ala Val Ala Lys Glu Gln Ser Ile Ser Thr Lys
610                 615                 620

Pro Pro Tyr Lys Glu Arg Lys Asp Glu Leu Lys
625                 630                 635

<210> SEQ ID NO 24
<211> LENGTH: 427
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Val Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala

```
            100                 105                 110
Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
                180                 185                 190

Ser Arg His Lys Arg Trp Ala His Trp His Thr Gly Leu Ala Leu Cys
                195                 200                 205

Trp Leu Val Pro Met Asp Ala Ile Tyr Asn Tyr Ile Thr Gln Gln Asn
        210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Gly Gly Gly Ser Gly
                260                 265                 270

Gly Gly Gly Ser Gly Gly Gly Ser Ala Pro Ile Ser Ser His Cys
        275                 280                 285

Arg Leu Asp Lys Ser Asn Phe Gln Gln Pro Tyr Ile Thr Asn Arg Thr
        290                 295                 300

Phe Met Leu Ala Lys Glu Ala Ser Leu Ala Asp Asn Asn Thr Asp Val
305                 310                 315                 320

Arg Leu Ile Gly Glu Lys Leu Phe His Gly Val Ser Met Ser Glu Arg
                325                 330                 335

Cys Tyr Leu Met Lys Gln Val Leu Asn Phe Thr Leu Glu Glu Val Leu
                340                 345                 350

Phe Pro Gln Ser Asp Arg Phe Gln Pro Tyr Met Gln Glu Val Val Pro
                355                 360                 365

Phe Leu Ala Arg Leu Ser Asn Arg Leu Ser Thr Cys His Ile Glu Gly
        370                 375                 380

Asp Asp Leu His Ile Gln Arg Asn Val Gln Lys Leu Lys Asp Thr Val
385                 390                 395                 400

Lys Lys Leu Gly Glu Ser Gly Glu Ile Lys Ala Ile Gly Glu Leu Asp
                405                 410                 415

Leu Leu Phe Met Ser Leu Arg Asn Ala Cys Ile
                420                 425

<210> SEQ ID NO 25
<211> LENGTH: 427
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Leu Glu Glu Ala Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30
```

-continued

```
Ser Asp Val Leu Asp Glu Gly Val Leu Tyr Tyr Ser Met Thr Ile
         35                  40                  45
Asn Asp Glu Gln Asn Asp Ile Lys Asp Glu Asp Lys Gly Glu Ser Ile
 50                  55                  60
Ile Thr Ile Gly Glu Phe Ala Thr Val Arg Ala Thr Arg His Tyr Val
 65                  70                  75                  80
Asn Gln Asp Ala Pro Phe Gly Val Ile His Leu Asp Ile Thr Thr Glu
                 85                  90                  95
Asn Gly Thr Lys Thr Tyr Ser Tyr Asn Arg Lys Glu Gly Glu Phe Ala
            100                 105                 110
Ile Asn Trp Leu Val Pro Ile Gly Glu Asp Ser Pro Ala Ser Ile Lys
        115                 120                 125
Ile Ser Val Asp Glu Leu Asp Gln Gln Arg Asn Ile Ile Glu Val Pro
    130                 135                 140
Lys Leu Tyr Ser Ile Asp Leu Asp Asn Gln Thr Leu Glu Gln Trp Lys
145                 150                 155                 160
Thr Gln Gly Asn Val Ser Phe Ser Val Thr Arg Pro Glu His Asn Ile
                165                 170                 175
Ala Ile Ser Trp Pro Ser Val Ser Tyr Lys Ala Ala Gln Lys Glu Gly
            180                 185                 190
Ser Arg His Lys Arg Trp Ala His Trp His Thr Gly Leu Ala Leu Cys
        195                 200                 205
Trp Leu Val Pro Met Asp Ala Ile Tyr Asn Tyr Ile Thr Gln Gln Asn
    210                 215                 220
Cys Thr Leu Gly Asp Asn Trp Phe Gly Gly Ser Tyr Glu Thr Val Ala
225                 230                 235                 240
Gly Thr Pro Lys Val Ile Thr Val Lys Gln Gly Ile Glu Gln Lys Pro
                245                 250                 255
Val Glu Gln Arg Ile His Phe Ser Lys Gly Gly Gly Gly Ser Gly
            260                 265                 270
Gly Gly Gly Ser Gly Gly Gly Ser Ala Pro Ile Ser Ser His Cys
        275                 280                 285
Arg Leu Asp Lys Ser Asn Phe Gln Gln Pro Tyr Ile Thr Asn Arg Thr
    290                 295                 300
Phe Met Leu Ala Lys Glu Ala Ser Leu Ala Asp Asn Asn Thr Asp Val
305                 310                 315                 320
Arg Leu Ile Gly Glu Lys Leu Phe His Gly Val Ser Met Ser Glu Arg
                325                 330                 335
Cys Tyr Leu Met Lys Gln Val Leu Asn Phe Thr Leu Glu Glu Val Leu
            340                 345                 350
Phe Pro Gln Ser Asp Arg Phe Gln Pro Tyr Met Gln Glu Val Val Pro
        355                 360                 365
Phe Leu Ala Arg Leu Ser Asn Arg Leu Ser Thr Cys His Ile Glu Gly
    370                 375                 380
Asp Asp Leu His Ile Gln Arg Asn Val Gln Lys Leu Lys Asp Thr Val
385                 390                 395                 400
Lys Lys Leu Gly Glu Ser Gly Glu Ile Lys Ala Ile Gly Glu Leu Asp
                405                 410                 415
Leu Leu Phe Met Ser Leu Arg Asn Ala Cys Ile
            420                 425
```

<210> SEQ ID NO 26
<211> LENGTH: 649
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: V or L
<220> FEATURE:
<221> NAME/KEY: MOD_RES
<222> LOCATION: (3)..(3)
<223> OTHER INFORMATION: E or D
<220> FEATURE:
<221> NAME/KEY: MOD_RES
<222> LOCATION: (4)..(4)
<223> OTHER INFORMATION: A or E
<220> FEATURE:
<221> NAME/KEY: MOD_RES
<222> LOCATION: (6)..(6)
<223> OTHER INFORMATION: N or K
<220> FEATURE:
<221> NAME/KEY: MOD_RES
<222> LOCATION: (16)..(16)
<223> OTHER INFORMATION: S or L
<220> FEATURE:
<221> NAME/KEY: MOD_RES
<222> LOCATION: (21)..(21)
<223> OTHER INFORMATION: P or L
<220> FEATURE:
<221> NAME/KEY: MOD_RES
<222> LOCATION: (24)..(24)
<223> OTHER INFORMATION: P or Q
<220> FEATURE:
<221> NAME/KEY: MOD_RES
<222> LOCATION: (30)..(30)
<223> OTHER INFORMATION: S or F
<220> FEATURE:
<221> NAME/KEY: MOD_RES
<222> LOCATION: (33)..(33)
<223> OTHER INFORMATION: S or G
<220> FEATURE:
<221> NAME/KEY: MOD_RES
<222> LOCATION: (56)..(56)
<223> OTHER INFORMATION: K or M
<220> FEATURE:
<221> NAME/KEY: MOD_RES
<222> LOCATION: (59)..(59)
<223> OTHER INFORMATION: D or G
<220> FEATURE:
<221> NAME/KEY: MOD_RES
<222> LOCATION: (67)..(67)
<223> OTHER INFORMATION: I or F
<220> FEATURE:
<221> NAME/KEY: MOD_RES
<222> LOCATION: (73)..(73)
<223> OTHER INFORMATION: V or I
<220> FEATURE:
<221> NAME/KEY: MOD_RES
<222> LOCATION: (81)..(81)
<223> OTHER INFORMATION: N or S
<220> FEATURE:
<221> NAME/KEY: MOD_RES
<222> LOCATION: (90)..(90)
<223> OTHER INFORMATION: H or N
<220> FEATURE:
<221> NAME/KEY: MOD_RES
<222> LOCATION: (101)..(101)
<223> OTHER INFORMATION: T or M
<220> FEATURE:
<221> NAME/KEY: MOD_RES
<222> LOCATION: (104)..(104)
<223> OTHER INFORMATION: Y or F
<220> FEATURE:
<221> NAME/KEY: MOD_RES
<222> LOCATION: (108)..(108)
<223> OTHER INFORMATION: E or D
<220> FEATURE:
<221> NAME/KEY: MOD_RES
<222> LOCATION: (109)..(109)
```

```
<223> OTHER INFORMATION: G or S
<220> FEATURE:
<221> NAME/KEY: MOD_RES
<222> LOCATION: (112)..(112)
<223> OTHER INFORMATION: A or T
<220> FEATURE:
<221> NAME/KEY: MOD_RES
<222> LOCATION: (114)..(114)
<223> OTHER INFORMATION: N or H
<220> FEATURE:
<221> NAME/KEY: MOD_RES
<222> LOCATION: (118)..(118)
<223> OTHER INFORMATION: P or I
<220> FEATURE:
<221> NAME/KEY: MOD_RES
<222> LOCATION: (119)..(119)
<223> OTHER INFORMATION: I or P
<220> FEATURE:
<221> NAME/KEY: MOD_RES
<222> LOCATION: (131)..(131)
<223> OTHER INFORMATION: V or I
<220> FEATURE:
<221> NAME/KEY: MOD_RES
<222> LOCATION: (134)..(134)
<223> OTHER INFORMATION: L or I
<220> FEATURE:
<221> NAME/KEY: MOD_RES
<222> LOCATION: (137)..(137)
<223> OTHER INFORMATION: Q or K
<220> FEATURE:
<221> NAME/KEY: MOD_RES
<222> LOCATION: (160)..(160)
<223> OTHER INFORMATION: K or E
<220> FEATURE:
<221> NAME/KEY: MOD_RES
<222> LOCATION: (161)..(161)
<223> OTHER INFORMATION: T or N
<220> FEATURE:
<221> NAME/KEY: MOD_RES
<222> LOCATION: (166)..(166)
<223> OTHER INFORMATION: S or F
<220> FEATURE:
<221> NAME/KEY: MOD_RES
<222> LOCATION: (168)..(168)
<223> OTHER INFORMATION: S or A
<220> FEATURE:
<221> NAME/KEY: MOD_RES
<222> LOCATION: (174)..(174)
<223> OTHER INFORMATION: H or Q
<220> FEATURE:
<221> NAME/KEY: MOD_RES
<222> LOCATION: (175)..(185)
<223> OTHER INFORMATION: This region may encompass one of the following
      sequences: "N", "S", "SIAKQS", or "SIAKQSIAKQS"
<220> FEATURE:
<221> NAME/KEY: MOD_RES
<222> LOCATION: (196)..(196)
<223> OTHER INFORMATION: K or N
<220> FEATURE:
<221> NAME/KEY: MOD_RES
<222> LOCATION: (199)..(199)
<223> OTHER INFORMATION: Q, E, or H
<220> FEATURE:
<221> NAME/KEY: MOD_RES
<222> LOCATION: (201)..(201)
<223> OTHER INFORMATION: E, N, or D
<220> FEATURE:
<221> NAME/KEY: MOD_RES
<222> LOCATION: (203)..(203)
<223> OTHER INFORMATION: S or A
<220> FEATURE:
<221> NAME/KEY: MOD_RES
<222> LOCATION: (210)..(210)
<223> OTHER INFORMATION: H or N
<220> FEATURE:
<221> NAME/KEY: MOD_RES
<222> LOCATION: (212)..(212)
<223> OTHER INFORMATION: H, L, F, or R
<220> FEATURE:
```

```
<221> NAME/KEY: MOD_RES
<222> LOCATION: (214)..(214)
<223> OTHER INFORMATION: G or T
<220> FEATURE:
<221> NAME/KEY: MOD_RES
<222> LOCATION: (215)..(215)
<223> OTHER INFORMATION: L or S
<220> FEATURE:
<221> NAME/KEY: MOD_RES
<222> LOCATION: (216)..(216)
<223> OTHER INFORMATION: A or P
<220> FEATURE:
<221> NAME/KEY: MOD_RES
<222> LOCATION: (217)..(217)
<223> OTHER INFORMATION: L, E, or K
<220> FEATURE:
<221> NAME/KEY: MOD_RES
<222> LOCATION: (218)..(218)
<223> OTHER INFORMATION: C or V
<220> FEATURE:
<221> NAME/KEY: MOD_RES
<222> LOCATION: (219)..(219)
<223> OTHER INFORMATION: W, V, or T
<220> FEATURE:
<221> NAME/KEY: MOD_RES
<222> LOCATION: (221)..(221)
<223> OTHER INFORMATION: V or absent
<220> FEATURE:
<221> NAME/KEY: MOD_RES
<222> LOCATION: (222)..(222)
<223> OTHER INFORMATION: P or absent
<220> FEATURE:
<221> NAME/KEY: MOD_RES
<222> LOCATION: (223)..(223)
<223> OTHER INFORMATION: M, I, L, or absent
<220> FEATURE:
<221> NAME/KEY: MOD_RES
<222> LOCATION: (224)..(224)
<223> OTHER INFORMATION: D or absent
<220> FEATURE:
<221> NAME/KEY: MOD_RES
<222> LOCATION: (225)..(225)
<223> OTHER INFORMATION: A or absent
<220> FEATURE:
<221> NAME/KEY: MOD_RES
<222> LOCATION: (226)..(226)
<223> OTHER INFORMATION: I or absent
<220> FEATURE:
<221> NAME/KEY: MOD_RES
<222> LOCATION: (227)..(227)
<223> OTHER INFORMATION: Y or C
<220> FEATURE:
<221> NAME/KEY: MOD_RES
<222> LOCATION: (228)..(228)
<223> OTHER INFORMATION: N or F
<220> FEATURE:
<221> NAME/KEY: MOD_RES
<222> LOCATION: (229)..(229)
<223> OTHER INFORMATION: Y or F
<220> FEATURE:
<221> NAME/KEY: MOD_RES
<222> LOCATION: (230)..(230)
<223> OTHER INFORMATION: I or E
<220> FEATURE:
<221> NAME/KEY: MOD_RES
<222> LOCATION: (231)..(231)
<223> OTHER INFORMATION: T or D
<220> FEATURE:
<221> NAME/KEY: MOD_RES
<222> LOCATION: (232)..(232)
<223> OTHER INFORMATION: Q or P
<220> FEATURE:
<221> NAME/KEY: MOD_RES
<222> LOCATION: (233)..(233)
<223> OTHER INFORMATION: Q, E, or A
<220> FEATURE:
<221> NAME/KEY: MOD_RES
<222> LOCATION: (234)..(234)
<223> OTHER INFORMATION: N, L, or Q
```

```
<220> FEATURE:
<221> NAME/KEY: MOD_RES
<222> LOCATION: (237)..(237)
<223> OTHER INFORMATION: L or Y
<220> FEATURE:
<221> NAME/KEY: MOD_RES
<222> LOCATION: (239)..(239)
<223> OTHER INFORMATION: D or E
<220> FEATURE:
<221> NAME/KEY: MOD_RES
<222> LOCATION: (240)..(240)
<223> OTHER INFORMATION: N or D
<220> FEATURE:
<221> NAME/KEY: MOD_RES
<222> LOCATION: (242)..(242)
<223> OTHER INFORMATION: F, H, or Y
<220> FEATURE:
<221> NAME/KEY: MOD_RES
<222> LOCATION: (245)..(245)
<223> OTHER INFORMATION: S or A
<220> FEATURE:
<221> NAME/KEY: MOD_RES
<222> LOCATION: (247)..(247)
<223> OTHER INFORMATION: E or K
<220> FEATURE:
<221> NAME/KEY: MOD_RES
<222> LOCATION: (252)..(252)
<223> OTHER INFORMATION: T or I
<220> FEATURE:
<221> NAME/KEY: MOD_RES
<222> LOCATION: (254)..(254)
<223> OTHER INFORMATION: K, E, or G
<220> FEATURE:
<221> NAME/KEY: MOD_RES
<222> LOCATION: (255)..(255)
<223> OTHER INFORMATION: V or A
<220> FEATURE:
<221> NAME/KEY: MOD_RES
<222> LOCATION: (257)..(257)
<223> OTHER INFORMATION: T or M
<220> FEATURE:
<221> NAME/KEY: MOD_RES
<222> LOCATION: (262)..(262)
<223> OTHER INFORMATION: I or M
<220> FEATURE:
<221> NAME/KEY: MOD_RES
<222> LOCATION: (266)..(266)
<223> OTHER INFORMATION: P, T, or A
<220> FEATURE:
<221> NAME/KEY: MOD_RES
<222> LOCATION: (275)..(275)
<223> OTHER INFORMATION: K, Q, or N
<220> FEATURE:
<221> NAME/KEY: MOD_RES
<222> LOCATION: (276)..(276)
<223> OTHER INFORMATION: G or K
<220> FEATURE:
<221> NAME/KEY: MOD_RES
<222> LOCATION: (279)..(279)
<223> OTHER INFORMATION: M or I
<220> FEATURE:
<221> NAME/KEY: MOD_RES
<222> LOCATION: (280)..(280)
<223> OTHER INFORMATION: S or E
<220> FEATURE:
<221> NAME/KEY: MOD_RES
<222> LOCATION: (281)..(281)
<223> OTHER INFORMATION: A or T
<220> FEATURE:
<221> NAME/KEY: MOD_RES
<222> LOCATION: (298)..(298)
<223> OTHER INFORMATION: S or G
<220> FEATURE:
<221> NAME/KEY: MOD_RES
<222> LOCATION: (303)..(303)
<223> OTHER INFORMATION: D or Y
<220> FEATURE:
<221> NAME/KEY: MOD_RES
<222> LOCATION: (305)..(305)
```

```
<223> OTHER INFORMATION: T, P, or Q
<220> FEATURE:
<221> NAME/KEY: MOD_RES
<222> LOCATION: (309)..(309)
<223> OTHER INFORMATION: S or Q
<220> FEATURE:
<221> NAME/KEY: MOD_RES
<222> LOCATION: (311)..(311)
<223> OTHER INFORMATION: A or V
<220> FEATURE:
<221> NAME/KEY: MOD_RES
<222> LOCATION: (313)..(313)
<223> OTHER INFORMATION: Q or N
<220> FEATURE:
<221> NAME/KEY: MOD_RES
<222> LOCATION: (316)..(316)
<223> OTHER INFORMATION: N or Q
<220> FEATURE:
<221> NAME/KEY: MOD_RES
<222> LOCATION: (322)..(322)
<223> OTHER INFORMATION: V or L
<220> FEATURE:
<221> NAME/KEY: MOD_RES
<222> LOCATION: (326)..(326)
<223> OTHER INFORMATION: I or M
<220> FEATURE:
<221> NAME/KEY: MOD_RES
<222> LOCATION: (329)..(329)
<223> OTHER INFORMATION: S or T
<220> FEATURE:
<221> NAME/KEY: MOD_RES
<222> LOCATION: (331)..(331)
<223> OTHER INFORMATION: L or I
<220> FEATURE:
<221> NAME/KEY: MOD_RES
<222> LOCATION: (334)..(334)
<223> OTHER INFORMATION: V or I
<220> FEATURE:
<221> NAME/KEY: MOD_RES
<222> LOCATION: (340)..(340)
<223> OTHER INFORMATION: D, E, or H
<220> FEATURE:
<221> NAME/KEY: MOD_RES
<222> LOCATION: (341)..(341)
<223> OTHER INFORMATION: E or G
<220> FEATURE:
<221> NAME/KEY: MOD_RES
<222> LOCATION: (343)..(343)
<223> OTHER INFORMATION: E or A
<220> FEATURE:
<221> NAME/KEY: MOD_RES
<222> LOCATION: (345)..(345)
<223> OTHER INFORMATION: E or A
<220> FEATURE:
<221> NAME/KEY: MOD_RES
<222> LOCATION: (347)..(347)
<223> OTHER INFORMATION: A or T
<220> FEATURE:
<221> NAME/KEY: MOD_RES
<222> LOCATION: (351)..(351)
<223> OTHER INFORMATION: S, D, or T
<220> FEATURE:
<221> NAME/KEY: MOD_RES
<222> LOCATION: (352)..(352)
<223> OTHER INFORMATION: D or A
<220> FEATURE:
<221> NAME/KEY: MOD_RES
<222> LOCATION: (353)..(353)
<223> OTHER INFORMATION: L or I
<220> FEATURE:
<221> NAME/KEY: MOD_RES
<222> LOCATION: (355)..(355)
<223> OTHER INFORMATION: R or Q
<220> FEATURE:
<221> NAME/KEY: MOD_RES
<222> LOCATION: (359)..(359)
<223> OTHER INFORMATION: N or D
<220> FEATURE:
<221> NAME/KEY: MOD_RES
```

```
<222> LOCATION: (363)..(363)
<223> OTHER INFORMATION: M or V
<220> FEATURE:
<221> NAME/KEY: MOD_RES
<222> LOCATION: (365)..(365)
<223> OTHER INFORMATION: T or I
<220> FEATURE:
<221> NAME/KEY: MOD_RES
<222> LOCATION: (370)..(370)
<223> OTHER INFORMATION: V or I
<220> FEATURE:
<221> NAME/KEY: MOD_RES
<222> LOCATION: (381)..(381)
<223> OTHER INFORMATION: H or E
<220> FEATURE:
<221> NAME/KEY: MOD_RES
<222> LOCATION: (384)..(384)
<223> OTHER INFORMATION: G or L
<220> FEATURE:
<221> NAME/KEY: MOD_RES
<222> LOCATION: (386)..(386)
<223> OTHER INFORMATION: T or I
<220> FEATURE:
<221> NAME/KEY: MOD_RES
<222> LOCATION: (393)..(393)
<223> OTHER INFORMATION: G or S
<220> FEATURE:
<221> NAME/KEY: MOD_RES
<222> LOCATION: (403)..(403)
<223> OTHER INFORMATION: F or L
<220> FEATURE:
<221> NAME/KEY: MOD_RES
<222> LOCATION: (404)..(404)
<223> OTHER INFORMATION: C or Y
<220> FEATURE:
<221> NAME/KEY: MOD_RES
<222> LOCATION: (407)..(407)
<223> OTHER INFORMATION: A or T
<220> FEATURE:
<221> NAME/KEY: MOD_RES
<222> LOCATION: (409)..(409)
<223> OTHER INFORMATION: K, E, or G
<220> FEATURE:
<221> NAME/KEY: MOD_RES
<222> LOCATION: (410)..(410)
<223> OTHER INFORMATION: S, P, or H
<220> FEATURE:
<221> NAME/KEY: MOD_RES
<222> LOCATION: (414)..(414)
<223> OTHER INFORMATION: S or L
<220> FEATURE:
<221> NAME/KEY: MOD_RES
<222> LOCATION: (415)..(415)
<223> OTHER INFORMATION: N or D
<220> FEATURE:
<221> NAME/KEY: MOD_RES
<222> LOCATION: (416)..(416)
<223> OTHER INFORMATION: N or S
<220> FEATURE:
<221> NAME/KEY: MOD_RES
<222> LOCATION: (423)..(423)
<223> OTHER INFORMATION: I or V
<220> FEATURE:
<221> NAME/KEY: MOD_RES
<222> LOCATION: (433)..(433)
<223> OTHER INFORMATION: P or L
<220> FEATURE:
<221> NAME/KEY: MOD_RES
<222> LOCATION: (441)..(441)
<223> OTHER INFORMATION: P or Q
<220> FEATURE:
<221> NAME/KEY: MOD_RES
<222> LOCATION: (453)..(453)
<223> OTHER INFORMATION: E or D
<220> FEATURE:
<221> NAME/KEY: MOD_RES
<222> LOCATION: (454)..(454)
<223> OTHER INFORMATION: A or T
<220> FEATURE:
```

```
<221> NAME/KEY: MOD_RES
<222> LOCATION: (455)..(455)
<223> OTHER INFORMATION: T or K
<220> FEATURE:
<221> NAME/KEY: MOD_RES
<222> LOCATION: (458)..(458)
<223> OTHER INFORMATION: A or T
<220> FEATURE:
<221> NAME/KEY: MOD_RES
<222> LOCATION: (461)..(461)
<223> OTHER INFORMATION: R or Q
<220> FEATURE:
<221> NAME/KEY: MOD_RES
<222> LOCATION: (463)..(463)
<223> OTHER INFORMATION: G or D
<220> FEATURE:
<221> NAME/KEY: MOD_RES
<222> LOCATION: (475)..(475)
<223> OTHER INFORMATION: V or A
<220> FEATURE:
<221> NAME/KEY: MOD_RES
<222> LOCATION: (479)..(479)
<223> OTHER INFORMATION: T, S, or N
<220> FEATURE:
<221> NAME/KEY: MOD_RES
<222> LOCATION: (485)..(485)
<223> OTHER INFORMATION: A, S, or T
<220> FEATURE:
<221> NAME/KEY: MOD_RES
<222> LOCATION: (491)..(491)
<223> OTHER INFORMATION: N or S
<220> FEATURE:
<221> NAME/KEY: MOD_RES
<222> LOCATION: (492)..(492)
<223> OTHER INFORMATION: N or D
<220> FEATURE:
<221> NAME/KEY: MOD_RES
<222> LOCATION: (495)..(495)
<223> OTHER INFORMATION: N, S, or K
<220> FEATURE:
<221> NAME/KEY: MOD_RES
<222> LOCATION: (497)..(497)
<223> OTHER INFORMATION: E, R, or K
<220> FEATURE:
<221> NAME/KEY: MOD_RES
<222> LOCATION: (498)..(498)
<223> OTHER INFORMATION: K, A, or E
<220> FEATURE:
<221> NAME/KEY: MOD_RES
<222> LOCATION: (502)..(502)
<223> OTHER INFORMATION: L or V
<220> FEATURE:
<221> NAME/KEY: MOD_RES
<222> LOCATION: (505)..(505)
<223> OTHER INFORMATION: A or S
<220> FEATURE:
<221> NAME/KEY: MOD_RES
<222> LOCATION: (507)..(507)
<223> OTHER INFORMATION: H or D
<220> FEATURE:
<221> NAME/KEY: MOD_RES
<222> LOCATION: (509)..(509)
<223> OTHER INFORMATION: E or S
<220> FEATURE:
<221> NAME/KEY: MOD_RES
<222> LOCATION: (510)..(510)
<223> OTHER INFORMATION: V or L
<220> FEATURE:
<221> NAME/KEY: MOD_RES
<222> LOCATION: (511)..(511)
<223> OTHER INFORMATION: A or N
<220> FEATURE:
<221> NAME/KEY: MOD_RES
<222> LOCATION: (512)..(512)
<223> OTHER INFORMATION: H or Y
<220> FEATURE:
<221> NAME/KEY: MOD_RES
<222> LOCATION: (513)..(513)
<223> OTHER INFORMATION: G or R
```

-continued

```
<220> FEATURE:
<221> NAME/KEY: MOD_RES
<222> LOCATION: (515)..(515)
<223> OTHER INFORMATION: A or T
<220> FEATURE:
<221> NAME/KEY: MOD_RES
<222> LOCATION: (517)..(517)
<223> OTHER INFORMATION: I or L
<220> FEATURE:
<221> NAME/KEY: MOD_RES
<222> LOCATION: (518)..(518)
<223> OTHER INFORMATION: K or Q
<220> FEATURE:
<221> NAME/KEY: MOD_RES
<222> LOCATION: (519)..(519)
<223> OTHER INFORMATION: E or K
<220> FEATURE:
<221> NAME/KEY: MOD_RES
<222> LOCATION: (522)..(522)
<223> OTHER INFORMATION: G or A
<220> FEATURE:
<221> NAME/KEY: MOD_RES
<222> LOCATION: (523)..(523)
<223> OTHER INFORMATION: E, D, or N
<220> FEATURE:
<221> NAME/KEY: MOD_RES
<222> LOCATION: (524)..(524)
<223> OTHER INFORMATION: Y, G, A, or N
<220> FEATURE:
<221> NAME/KEY: MOD_RES
<222> LOCATION: (525)..(525)
<223> OTHER INFORMATION: G or E
<220> FEATURE:
<221> NAME/KEY: MOD_RES
<222> LOCATION: (526)..(526)
<223> OTHER INFORMATION: L or G
<220> FEATURE:
<221> NAME/KEY: MOD_RES
<222> LOCATION: (527)..(527)
<223> OTHER INFORMATION: P or L
<220> FEATURE:
<221> NAME/KEY: MOD_RES
<222> LOCATION: (529)..(529)
<223> OTHER INFORMATION: R, P, or T
<220> FEATURE:
<221> NAME/KEY: MOD_RES
<222> LOCATION: (530)..(530)
<223> OTHER INFORMATION: A or E
<220> FEATURE:
<221> NAME/KEY: MOD_RES
<222> LOCATION: (531)..(531)
<223> OTHER INFORMATION: E or K
<220> FEATURE:
<221> NAME/KEY: MOD_RES
<222> LOCATION: (532)..(532)
<223> OTHER INFORMATION: R, Q, or K
<220> FEATURE:
<221> NAME/KEY: MOD_RES
<222> LOCATION: (533)..(533)
<223> OTHER INFORMATION: D, K, or E
<220> FEATURE:
<221> NAME/KEY: MOD_RES
<222> LOCATION: (534)..(534)
<223> OTHER INFORMATION: A, T, or S
<220> FEATURE:
<221> NAME/KEY: MOD_RES
<222> LOCATION: (540)..(540)
<223> OTHER INFORMATION: R or K
<220> FEATURE:
<221> NAME/KEY: MOD_RES
<222> LOCATION: (543)..(543)
<223> OTHER INFORMATION: I or L
<220> FEATURE:
<221> NAME/KEY: MOD_RES
<222> LOCATION: (544)..(544)
<223> OTHER INFORMATION: P or H
<220> FEATURE:
<221> NAME/KEY: MOD_RES
<222> LOCATION: (545)..(545)
```

```
<223> OTHER INFORMATION: R or Q
<220> FEATURE:
<221> NAME/KEY: MOD_RES
<222> LOCATION: (554)..(554)
<223> OTHER INFORMATION: T or I
<220> FEATURE:
<221> NAME/KEY: MOD_RES
<222> LOCATION: (556)..(556)
<223> OTHER INFORMATION: T, A, or I
<220> FEATURE:
<221> NAME/KEY: MOD_RES
<222> LOCATION: (557)..(557)
<223> OTHER INFORMATION: P or D
<220> FEATURE:
<221> NAME/KEY: MOD_RES
<222> LOCATION: (560)..(560)
<223> OTHER INFORMATION: N or K
<220> FEATURE:
<221> NAME/KEY: MOD_RES
<222> LOCATION: (561)..(561)
<223> OTHER INFORMATION: A or E
<220> FEATURE:
<221> NAME/KEY: MOD_RES
<222> LOCATION: (562)..(562)
<223> OTHER INFORMATION: E, R, or D
<220> FEATURE:
<221> NAME/KEY: MOD_RES
<222> LOCATION: (563)..(563)
<223> OTHER INFORMATION: E, N, or R
<220> FEATURE:
<221> NAME/KEY: MOD_RES
<222> LOCATION: (564)..(564)
<223> OTHER INFORMATION: H or L
<220> FEATURE:
<221> NAME/KEY: MOD_RES
<222> LOCATION: (565)..(565)
<223> OTHER INFORMATION: I or V
<220> FEATURE:
<221> NAME/KEY: MOD_RES
<222> LOCATION: (566)..(566)
<223> OTHER INFORMATION: T or E
<220> FEATURE:
<221> NAME/KEY: MOD_RES
<222> LOCATION: (567)..(567)
<223> OTHER INFORMATION: Q, R, H, or D
<220> FEATURE:
<221> NAME/KEY: MOD_RES
<222> LOCATION: (572)..(572)
<223> OTHER INFORMATION: S or P
<220> FEATURE:
<221> NAME/KEY: MOD_RES
<222> LOCATION: (583)..(583)
<223> OTHER INFORMATION: P or T
<220> FEATURE:
<221> NAME/KEY: MOD_RES
<222> LOCATION: (584)..(584)
<223> OTHER INFORMATION: E or D
<220> FEATURE:
<221> NAME/KEY: MOD_RES
<222> LOCATION: (585)..(585)
<223> OTHER INFORMATION: S, A, or R
<220> FEATURE:
<221> NAME/KEY: MOD_RES
<222> LOCATION: (586)..(586)
<223> OTHER INFORMATION: A, E, or V
<220> FEATURE:
<221> NAME/KEY: MOD_RES
<222> LOCATION: (587)..(587)
<223> OTHER INFORMATION: G, E, or D
<220> FEATURE:
<221> NAME/KEY: MOD_RES
<222> LOCATION: (589)..(589)
<223> OTHER INFORMATION: E or S
<220> FEATURE:
<221> NAME/KEY: MOD_RES
<222> LOCATION: (590)..(590)
<223> OTHER INFORMATION: D or N
<220> FEATURE:
<221> NAME/KEY: MOD_RES
```

```
<222> LOCATION: (593)..(593)
<223> OTHER INFORMATION: V or A
<220> FEATURE:
<221> NAME/KEY: MOD_RES
<222> LOCATION: (598)..(598)
<223> OTHER INFORMATION: M or I
<220> FEATURE:
<221> NAME/KEY: MOD_RES
<222> LOCATION: (601)..(601)
<223> OTHER INFORMATION: H or Y
<220> FEATURE:
<221> NAME/KEY: MOD_RES
<222> LOCATION: (602)..(602)
<223> OTHER INFORMATION: A or G
<220> FEATURE:
<221> NAME/KEY: MOD_RES
<222> LOCATION: (613)..(613)
<223> OTHER INFORMATION: A or S
<220> FEATURE:
<221> NAME/KEY: MOD_RES
<222> LOCATION: (615)..(615)
<223> OTHER INFORMATION: E or A
<220> FEATURE:
<221> NAME/KEY: MOD_RES
<222> LOCATION: (616)..(616)
<223> OTHER INFORMATION: E, A, Q, G, V, or R
<220> FEATURE:
<221> NAME/KEY: MOD_RES
<222> LOCATION: (618)..(618)
<223> OTHER INFORMATION: A, P, or T
<220> FEATURE:
<221> NAME/KEY: MOD_RES
<222> LOCATION: (619)..(619)
<223> OTHER INFORMATION: I, T, or P
<220> FEATURE:
<221> NAME/KEY: MOD_RES
<222> LOCATION: (620)..(620)
<223> OTHER INFORMATION: D or A
<220> FEATURE:
<221> NAME/KEY: MOD_RES
<222> LOCATION: (624)..(629)
<223> OTHER INFORMATION: This region may encompass one of the following
      sequences: "V" or "VVKEAI"
<220> FEATURE:
<221> NAME/KEY: MOD_RES
<222> LOCATION: (631)..(631)
<223> OTHER INFORMATION: K or E
<220> FEATURE:
<221> NAME/KEY: MOD_RES
<222> LOCATION: (637)..(637)
<223> OTHER INFORMATION: T, A, or P
<220> FEATURE:
<221> NAME/KEY: MOD_RES
<222> LOCATION: (644)..(644)
<223> OTHER INFORMATION: R, Q, or H
<220> FEATURE:
<221> NAME/KEY: MOD_RES
<222> LOCATION: (645)..(645)
<223> OTHER INFORMATION: K or absent
<220> FEATURE:
<223> OTHER INFORMATION: See specification as filed for detailed
      description of substitutions and preferred embodiments

<400> SEQUENCE: 26

Xaa Glu Xaa Xaa Leu Xaa Ile Phe Asp Glu Cys Arg Ser Pro Cys Xaa
1               5                   10                  15

Leu Thr Pro Glu Xaa Gly Lys Xaa Ile Gln Ser Lys Leu Xaa Ile Pro
            20                  25                  30

Xaa Asp Val Val Leu Asp Glu Gly Val Leu Tyr Tyr Ser Met Thr Ile
        35                  40                  45

Asn Asp Glu Gln Asn Asp Ile Xaa Asp Glu Xaa Lys Gly Glu Ser Ile
    50                  55                  60

Ile Thr Xaa Gly Glu Phe Ala Thr Xaa Arg Ala Thr Arg His Tyr Val
65                  70                  75                  80
```

```
Xaa Gln Asp Ala Pro Phe Gly Val Ile Xaa Leu Asp Ile Thr Thr Glu
             85                  90                  95

Asn Gly Thr Lys Xaa Tyr Ser Xaa Asn Arg Lys Xaa Xaa Glu Phe Xaa
            100                 105                 110

Ile Xaa Trp Leu Val Xaa Xaa Gly Glu Asp Ser Pro Ala Ser Ile Lys
            115                 120                 125

Ile Ser Xaa Asp Glu Xaa Asp Gln Xaa Arg Asn Ile Ile Glu Val Pro
130                 135                 140

Lys Leu Tyr Ser Ile Asp Leu Asp Asn Gln Thr Leu Glu Gln Trp Xaa
145                 150                 155                 160

Xaa Gln Gly Asn Val Xaa Phe Xaa Val Thr Arg Pro Glu Xaa Xaa Xaa
            165                 170                 175

Xaa Xaa Xaa Xaa Xaa Xaa Xaa Xaa Ile Ala Ile Ser Trp Pro Ser
            180                 185                 190       Ser

Val Ser Tyr Xaa Ala Ala Xaa Lys Xaa Gly Xaa Arg His Lys Arg Trp
            195                 200                 205

Ala Xaa Trp Xaa Thr Xaa Xaa Xaa Xaa Xaa Xaa Leu Xaa Xaa Xaa Xaa
            210                 215                 220

Xaa Xaa Xaa Xaa Xaa Xaa Xaa Xaa Xaa Cys Thr Xaa Gly Xaa Xaa
225                 230                 235                 240

Trp Xaa Gly Gly Xaa Tyr Xaa Thr Val Ala Gly Xaa Pro Xaa Xaa Ile
            245                 250                 255

Xaa Val Lys Gln Gly Xaa Glu Gln Lys Xaa Val Glu Gln Arg Ile His
            260                 265                 270

Phe Ser Xaa Xaa Asn Ala Xaa Xaa Xaa Leu Ala Ala His Arg Val Cys
            275                 280                 285

Gly Val Pro Leu Glu Thr Leu Ala Arg Xaa Arg Lys Pro Arg Xaa Leu
            290                 295                 300

Xaa Asp Asp Leu Xaa Cys Xaa Tyr Xaa Ala Gln Xaa Ile Val Ser Leu
305                 310                 315                 320

Phe Xaa Ala Thr Arg Xaa Leu Phe Xaa His Xaa Asp Ser Xaa Phe Thr
            325                 330                 335

Leu Asn Leu Xaa Xaa Gln Xaa Pro Xaa Val Xaa Glu Arg Leu Xaa Xaa
            340                 345                 350

Xaa Arg Xaa Ile Asn Glu Xaa Asn Pro Gly Xaa Val Xaa Gln Val Leu
            355                 360                 365

Thr Xaa Ala Arg Gln Ile Tyr Asn Asp Tyr Val Thr Xaa His Pro Xaa
            370                 375                 380

Leu Xaa Pro Glu Gln Thr Ser Ala Xaa Ala Gln Ala Ala Asp Ile Leu
385                 390                 395                 400

Ser Leu Xaa Xaa Pro Asp Xaa Asp Xaa Xaa Cys Val Ala Xaa Xaa Xaa
            405                 410                 415

Asp Gln Ala Asn Ile Asn Xaa Glu Ser Arg Ser Gly Arg Ser Tyr Leu
            420                 425                 430

Xaa Glu Asn Arg Ala Val Ile Thr Xaa Gln Gly Val Thr Asn Trp Thr
            435                 440                 445

Tyr Gln Glu Leu Xaa Xaa Xaa His Gln Xaa Leu Thr Xaa Glu Xaa Tyr
            450                 455                 460

Val Phe Val Gly Tyr His Gly Thr Asn His Xaa Ala Ala Gln Xaa Ile
465                 470                 475                 480

Val Asn Arg Ile Xaa Pro Val Pro Arg Gly Xaa Xaa Thr Glu Xaa Glu
            485                 490                 495
```

```
Xaa Xaa Trp Gly Gly Xaa Tyr Val Xaa Thr Xaa Ala Xaa Xaa Xaa Xaa
            500                 505                 510

Xaa Tyr Xaa Arg Xaa Xaa Xaa Gly Thr Xaa Xaa Xaa Xaa Xaa Xaa Thr
        515                 520                 525

Xaa Xaa Xaa Xaa Xaa Xaa Arg Gly Val Met Leu Xaa Val Tyr Xaa Xaa
            530                 535                 540

Xaa Ala Ser Leu Glu Arg Phe Tyr Arg Xaa Asn Xaa Xaa Leu Glu Xaa
545                 550                 555                 560

Xaa Xaa Xaa Xaa Xaa Xaa Xaa Val Ile Gly His Xaa Leu Pro Leu Arg
            565                 570                 575

Asn Glu Ala Phe Thr Gly Xaa Xaa Xaa Xaa Gly Xaa Xaa Glu Thr
            580                 585                 590

Xaa Ile Gly Trp Asp Xaa Ala Ile Xaa Xaa Val Ala Ile Pro Ser Thr
            595                 600                 605

Ile Pro Gly Asn Xaa Tyr Xaa Xaa Leu Xaa Xaa Xaa Glu Glu Ala Xaa
            610                 615                 620

Xaa Xaa Xaa Xaa Xaa Ala Xaa Glu Gln Ser Ile Ser Xaa Lys Pro Pro
625                 630                 635                 640

Tyr Lys Glu Xaa Xaa Asp Glu Leu Lys
            645
```

<210> SEQ ID NO 27
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(60)
<223> OTHER INFORMATION: This sequence may encompass 1-15 "Gly Gly Gly
      Ser" repeating units

<400> SEQUENCE: 27

```
Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

Gly Gly Gly Ser Gly Gly Gly Ser Gly Gly Gly Ser
    50                  55                  60
```

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Gly Gly Gly Gly Ser
1               5
```

<210> SEQ ID NO 29
<211> LENGTH: 90
<212> TYPE: PRT
<213> ORGANISM: Artificial Sequence
<220> FEATURE:
<223> OTHER INFORMATION: Description of Artificial Sequence: Synthetic

```
                                 polypeptide
<220> FEATURE:
<221> NAME/KEY: MISC_FEATURE
<222> LOCATION: (1)..(90)
<223> OTHER INFORMATION: This sequence may encompass 1-15 "Gly Gly Gly
      Gly Gly Ser" repeating units

<400> SEQUENCE: 29

Gly Gly Gly Gly Gly Ser Gly Gly Gly Gly Ser Gly Gly Gly Gly
1               5                   10                  15

Gly Ser Gly Gly Gly Gly Ser Gly Gly Gly Gly Ser Gly Gly Gly Gly
            20                  25                  30

Gly Gly Gly Ser Gly Gly Gly Gly Ser Gly Gly Gly Gly Ser
            35                  40                  45

Gly Gly Gly Gly Gly Ser Gly Gly Gly Gly Ser Gly Gly Gly Gly
            50                  55                  60

Gly Ser Gly Gly Gly Gly Ser Gly Gly Gly Gly Ser Gly Gly
65                  70                  75                  80

Gly Gly Gly Ser Gly Gly Gly Gly Gly Ser
                85                  90

<210> SEQ ID NO 30
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Ala Val Leu Gln Lys Ser Met Ser Phe Ser Leu Met Gly Thr Leu
1               5                   10                  15

Ala Ala Ser Cys Leu Leu Leu Ile Ala Leu Trp Ala Gln Glu Ala Asn
            20                  25                  30

Ala Leu Pro Val Asn Thr Arg Cys Lys Leu Glu Val Ser Asn Phe Gln
            35                  40                  45

Gln Pro Tyr Ile Val Asn Arg Thr Phe Met Leu Ala Lys Glu Ala Ser
        50                  55                  60

Leu Ala Asp Asn Asn Thr Asp Val Arg Leu Ile Gly Glu Lys Leu Phe
65                  70                  75                  80

Arg Gly Val Ser Ala Lys Asp Gln Cys Tyr Leu Met Lys Gln Val Leu
                85                  90                  95

Asn Phe Thr Leu Glu Asp Val Leu Leu Pro Gln Ser Asp Arg Phe Gln
            100                 105                 110

Pro Tyr Met Gln Glu Val Val Pro Phe Leu Thr Lys Leu Ser Asn Gln
            115                 120                 125

Leu Ser Ser Cys His Ile Ser Gly Asp Asp Gln Asn Ile Gln Lys Asn
        130                 135                 140

Val Arg Arg Leu Lys Glu Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Val

<210> SEQ ID NO 31
<211> LENGTH: 25
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 31

Gly Gly Gly Gly Ser Gly Gly Gly Ser Gly Gly Gly Ser Gly
1               5                   10                  15

Gly Gly Gly Ser Gly Gly Gly Ser
            20                  25

<210> SEQ ID NO 32
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
    50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
    130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
        195                 200                 205

Cys Trp Leu Val Pro Met Asp Ala Ile Tyr Asn Tyr Ile Thr Gln Gln
    210                 215                 220

Asn Cys Thr Leu Gly Asp Asn Trp Phe Gly Gly Ser Tyr Glu Thr Val
225                 230                 235                 240

Ala Gly Thr Pro Lys Val Ile Thr Val Lys Gln Gly Ile Glu Gln Lys
                245                 250                 255

Pro Val Glu Gln Arg Ile His Phe Ser Lys Gly Gly Gly Gly Ser
            260                 265                 270

Ala Pro Ile Ser Ser His Cys Arg Leu Asp Lys Ser Asn Phe Gln Gln
        275                 280                 285

Pro Tyr Ile Thr Asn Arg Thr Phe Met Leu Ala Lys Glu Ala Ser Leu
    290                 295                 300

Ala Asp Asn Asn Thr Asp Val Arg Leu Ile Gly Glu Lys Leu Phe His
305                 310                 315                 320

Gly Val Ser Met Ser Glu Arg Cys Tyr Leu Met Lys Gln Val Leu Asn
            325                 330                 335

Phe Thr Leu Glu Glu Val Leu Phe Pro Gln Ser Asp Arg Phe Gln Pro
        340                 345                 350

Tyr Met Gln Glu Val Val Pro Phe Leu Ala Arg Leu Ser Asn Arg Leu
    355                 360                 365

Ser Thr Cys His Ile Glu Gly Asp Asp Leu His Ile Gln Arg Asn Val
370                 375                 380

Gln Lys Leu Lys Asp Thr Val Lys Lys Leu Gly Glu Ser Gly Glu Ile
385                 390                 395                 400

Lys Ala Ile Gly Glu Leu Asp Leu Leu Phe Met Ser Leu Arg Asn Ala
            405                 410                 415

Cys Ile

<210> SEQ ID NO 33
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
    50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
        115                 120                 125

Lys Ile Ser Val Asp Glu Leu Asp Gln Gln Arg Asn Ile Ile Glu Val
    130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
        195                 200                 205

Cys Trp Leu Val Pro Met Asp Ala Ile Tyr Asn Tyr Ile Thr Gln Gln
    210                 215                 220

Asn Cys Thr Leu Gly Asp Asn Trp Phe Gly Gly Ser Tyr Glu Thr Val
225                 230                 235                 240

```
Ala Gly Thr Pro Lys Val Ile Thr Val Lys Gln Gly Ile Glu Gln Lys
            245                 250                 255

Pro Val Glu Gln Arg Ile His Phe Ser Lys Gly Gly Gly Gly Ser
        260                 265                 270

Gly Gly Gly Gly Ser Gly Gly Gly Ser Gly Gly Gly Ser Gly
        275                 280                 285

Gly Gly Gly Ser Ala Pro Ile Ser Ser His Cys Arg Leu Asp Lys Ser
        290                 295                 300

Asn Phe Gln Gln Pro Tyr Ile Thr Asn Arg Thr Phe Met Leu Ala Lys
305                 310                 315                 320

Glu Ala Ser Leu Ala Asp Asn Asn Thr Asp Val Arg Leu Ile Gly Glu
                325                 330                 335

Lys Leu Phe His Gly Val Ser Met Ser Glu Arg Cys Tyr Leu Met Lys
                340                 345                 350

Gln Val Leu Asn Phe Thr Leu Glu Glu Val Leu Phe Pro Gln Ser Asp
                355                 360                 365

Arg Phe Gln Pro Tyr Met Gln Glu Val Val Pro Phe Leu Ala Arg Leu
370                 375                 380

Ser Asn Arg Leu Ser Thr Cys His Ile Glu Gly Asp Asp Leu His Ile
385                 390                 395                 400

Gln Arg Asn Val Gln Lys Leu Lys Asp Thr Val Lys Lys Leu Gly Glu
                405                 410                 415

Ser Gly Glu Ile Lys Ala Ile Gly Glu Leu Asp Leu Leu Phe Met Ser
                420                 425                 430

Leu Arg Asn Ala Cys Ile
            435

<210> SEQ ID NO 34
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Ala Pro Ile Ser Ser His Cys Arg Leu Asp Lys Ser Asn Phe Gln
1               5                   10                  15

Gln Pro Tyr Ile Thr Asn Arg Thr Phe Met Leu Ala Lys Glu Ala Ser
            20                  25                  30

Leu Ala Asp Asn Asn Thr Asp Val Arg Leu Ile Gly Glu Lys Leu Phe
        35                  40                  45

His Gly Val Ser Met Ser Glu Arg Cys Tyr Leu Met Lys Gln Val Leu
    50                  55                  60

Asn Phe Thr Leu Glu Glu Val Leu Phe Pro Gln Ser Asp Arg Phe Gln
65                  70                  75                  80

Pro Tyr Met Gln Glu Val Val Pro Phe Leu Ala Arg Leu Ser Asn Arg
                85                  90                  95

Leu Ser Thr Cys His Ile Glu Gly Asp Asp Leu His Ile Gln Arg Asn
            100                 105                 110

Val Gln Lys Leu Lys Asp Thr Val Lys Lys Leu Gly Glu Ser Gly Glu
        115                 120                 125

Ile Lys Ala Ile Gly Glu Leu Asp Leu Leu Phe Met Ser Leu Arg Asn
    130                 135                 140

Ala Cys Ile Gly Gly Gly Gly Ser Val Glu Glu Ala Leu Asn Ile Phe
145                 150                 155                 160
```

```
Asp Glu Cys Arg Ser Pro Cys Ser Leu Thr Pro Glu Pro Gly Lys Pro
            165                 170                 175

Ile Gln Ser Lys Leu Ser Ile Pro Ser Asp Val Val Leu Asp Glu Gly
        180                 185                 190

Val Leu Tyr Tyr Ser Met Thr Ile Asn Asp Glu Gln Asn Asp Ile Lys
        195                 200                 205

Asp Glu Asp Lys Gly Glu Ser Ile Ile Thr Ile Gly Glu Phe Ala Thr
    210                 215                 220

Val Arg Ala Thr Arg His Tyr Val Asn Gln Asp Ala Pro Phe Gly Val
225                 230                 235                 240

Ile His Leu Asp Ile Thr Thr Glu Asn Gly Thr Lys Thr Tyr Ser Tyr
                245                 250                 255

Asn Arg Lys Glu Gly Glu Phe Ala Ile Asn Trp Leu Val Pro Ile Gly
            260                 265                 270

Glu Asp Ser Pro Ala Ser Ile Lys Ile Ser Val Asp Glu Leu Asp Gln
        275                 280                 285

Gln Arg Asn Ile Ile Glu Val Pro Lys Leu Tyr Ser Ile Asp Leu Asp
    290                 295                 300

Asn Gln Thr Leu Glu Gln Trp Lys Thr Gln Gly Asn Val Ser Phe Ser
305                 310                 315                 320

Val Thr Arg Pro Glu His Asn Ile Ala Ile Ser Trp Pro Ser Val Ser
                325                 330                 335

Tyr Lys Ala Ala Gln Lys Glu Gly Ser Arg His Lys Arg Trp Ala His
            340                 345                 350

Trp His Thr Gly Leu Ala Leu Cys Trp Leu Val Pro Met Asp Ala Ile
        355                 360                 365

Tyr Asn Tyr Ile Thr Gln Gln Asn Cys Thr Leu Gly Asp Asn Trp Phe
    370                 375                 380

Gly Gly Ser Tyr Glu Thr Val Ala Gly Thr Pro Lys Val Ile Thr Val
385                 390                 395                 400

Lys Gln Gly Ile Glu Gln Lys Pro Val Glu Gln Arg Ile His Phe Ser
                405                 410                 415

Lys Gly

<210> SEQ ID NO 35
<211> LENGTH: 538
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Ser Asp Val Val Leu Asp Glu Gly Val Leu Tyr Tyr Ser Met Thr
        35                  40                  45

Ile Asn Asp Glu Gln Asn Asp Ile Lys Asp Glu Asp Lys Gly Glu Ser
    50                  55                  60

Ile Ile Thr Ile Gly Glu Phe Ala Thr Val Arg Ala Thr Arg His Tyr
65                  70                  75                  80

Val Asn Gln Asp Ala Pro Phe Gly Val Ile His Leu Asp Ile Thr Thr
                85                  90                  95
```

-continued

Glu Asn Gly Thr Lys Thr Tyr Ser Tyr Asn Arg Lys Glu Gly Glu Phe
            100                 105                 110

Ala Ile Asn Trp Leu Val Pro Ile Gly Glu Asp Ser Pro Ala Ser Ile
            115                 120                 125

Lys Ile Ser Val Asp Glu Leu Asp Gln Gln Arg Asn Ile Ile Glu Val
            130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
            195                 200                 205

Cys Trp Leu Val Pro Met Asp Ala Ile Tyr Asn Tyr Ile Thr Gln Gln
            210                 215                 220

Asn Cys Thr Leu Gly Asp Asn Trp Phe Gly Gly Ser Tyr Glu Thr Val
225                 230                 235                 240

Ala Gly Thr Pro Lys Val Ile Thr Val Lys Gln Gly Ile Glu Gln Lys
                245                 250                 255

Pro Val Glu Gln Arg Ile His Phe Ser Lys Gly Asn Ala Met Ser Ala
            260                 265                 270

Leu Ala Ala His Arg Val Cys Gly Val Pro Leu Glu Thr Leu Ala Arg
            275                 280                 285

Ser Arg Lys Pro Arg Asp Leu Thr Asp Asp Leu Ser Cys Ala Tyr Gln
            290                 295                 300

Ala Gln Asn Ile Val Ser Leu Phe Val Ala Thr Arg Ile Leu Phe Ser
305                 310                 315                 320

His Leu Asp Ser Val Phe Thr Leu Asn Leu Asp Glu Gln Glu Pro Glu
                325                 330                 335

Val Ala Glu Arg Leu Ser Asp Leu Arg Arg Ile Asn Glu Asn Asn Pro
            340                 345                 350

Gly Met Val Thr Gln Val Leu Thr Val Ala Arg Gln Ile Tyr Asn Asp
            355                 360                 365

Tyr Val Thr His His Pro Gly Leu Thr Pro Glu Gln Thr Ser Ala Gly
            370                 375                 380

Ala Gln Ala Gly Gly Gly Ser Ala Pro Ile Ser Ser His Cys Arg
385                 390                 395                 400

Leu Asp Lys Ser Asn Phe Gln Gln Pro Tyr Ile Thr Asn Arg Thr Phe
                405                 410                 415

Met Leu Ala Lys Glu Ala Ser Leu Ala Asp Asn Asn Thr Asp Val Arg
            420                 425                 430

Leu Ile Gly Glu Lys Leu Phe His Gly Val Ser Met Ser Glu Arg Cys
            435                 440                 445

Tyr Leu Met Lys Gln Val Leu Asn Phe Thr Leu Glu Glu Val Leu Phe
            450                 455                 460

Pro Gln Ser Asp Arg Phe Gln Pro Tyr Met Gln Glu Val Val Pro Phe
465                 470                 475                 480

Leu Ala Arg Leu Ser Asn Arg Leu Ser Thr Cys His Ile Glu Gly Asp
                485                 490                 495

Asp Leu His Ile Gln Arg Asn Val Gln Lys Leu Lys Asp Thr Val Lys
            500                 505                 510

Lys Leu Gly Glu Ser Gly Glu Ile Lys Ala Ile Gly Glu Leu Asp Leu
            515                 520                 525

Leu Phe Met Ser Leu Arg Asn Ala Cys Ile
        530                 535

<210> SEQ ID NO 36
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(75)
<223> OTHER INFORMATION: This sequence may encompass 1-15 "Gly Gly Gly
      Gly Ser" repeating units

<400> SEQUENCE: 36

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Ser Gly Gly Gly Ser Gly Gly Gly
            35                  40                  45

Gly Ser Gly Gly Gly Ser Gly Gly Gly Ser Gly Gly Gly Gly
        50                  55                  60

Ser Gly Gly Gly Gly Ser Gly Gly Gly Gly Ser
65                  70                  75

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Ile Ala Lys Gln Ser
1               5

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Ile Ala Lys Gln Ser Ile Ala Lys Gln Ser
1               5                   10

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Val Lys Glu Ala Ile
1               5

```
<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1-15 "Gly Ser"
      repeating units

<400> SEQUENCE: 40

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser
            20                  25                  30

<210> SEQ ID NO 41
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(45)
<223> OTHER INFORMATION: This sequence may encompass 1-15 "Gly Gly Ser"
      repeating units

<400> SEQUENCE: 41

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser
            35                  40                  45
```